(12) United States Patent
Reif et al.

(10) Patent No.: US 12,662,693 B2
(45) Date of Patent: Jun. 23, 2026

(54) ANALYTICAL EVALUATION OF AQUEOUS LIQUID MEDIA WITH SAMPLE MONITORING STRUCTURE HAVING SIZE-SENSITIVE FLUORESCENT HYDROGEL

(71) Applicant: Sartorius BioAnalytical Instruments, Inc., Bohemia, NY (US)

(72) Inventors: Oscar-Werner Reif, Hannover (DE); Michael W Olszowy, Erie, CO (US); Jan Schwellenbach, Dransfeld (DE)

( * ) Notice: Subject to any disclaimer, the term of this patent is extended or adjusted under 35 U.S.C. 154(b) by 408 days.

(21) Appl. No.: 18/546,419

(22) PCT Filed: Feb. 18, 2022

(86) PCT No.: PCT/US2022/017040
§ 371 (c)(1),
(2) Date: Aug. 14, 2023

(87) PCT Pub. No.: WO2022/178290
PCT Pub. Date: Aug. 25, 2022

(65) Prior Publication Data
US 2025/0019738 A1 Jan. 16, 2025

Related U.S. Application Data

(60) Provisional application No. 63/151,252, filed on Feb. 19, 2021.

(30) Foreign Application Priority Data

Feb. 19, 2021 (EP) ..................................... 21158037

(51) Int. Cl.
$C12Q\ 1/04$ (2006.01)
$C12M\ 1/12$ (2006.01)
$G01N\ 15/14$ (2024.01)

(52) U.S. Cl.
CPC ............... *C12Q 1/04* (2013.01); *C12M 25/04* (2013.01); *C12Q 1/045* (2013.01); *G01N 15/1425* (2013.01); *G01N 15/1456* (2013.01)

(58) Field of Classification Search
CPC .......... C12Q 1/04; C12Q 1/045; C12M 25/04; G01N 15/1425; G01N 15/1456;
(Continued)

(56) References Cited

U.S. PATENT DOCUMENTS

| | | | |
|---|---|---|---|
| 5,747,349 A | 5/1998 | Van et al. | |
| 9,506,029 B2 | 11/2016 | Schmidt et al. | |

(Continued)

FOREIGN PATENT DOCUMENTS

| | | |
|---|---|---|
| WO | 2010132829 A2 | 11/2010 |
| WO | 2019246033 A1 | 12/2019 |
| WO | 2020139844 A1 | 7/2020 |

OTHER PUBLICATIONS

Ge, Minghao et al., "A hyaluronic acid fluorescent hydrogel based on fluorescence resonance energy transfer for sensitive detection of hyaluronidase", Analytical and Bioanalytical Chemistry, vol. 412, No. 8, Feb. 7, 2020, pp. 1915-1923 (Year: 2020).*

(Continued)

*Primary Examiner* — Dennis White
(74) *Attorney, Agent, or Firm* — Holzer Patel Drennan

(57) ABSTRACT

A sample monitoring structure includes fluorescently-labeled hydrogel that is size-responsive to changes in one or more properties of aqueous liquid medium contacted with the sample monitoring structure. An intensity of a fluorescent emission from the sample monitoring structure changes with changes in the size of the fluorescently-labeled hydrogel. The sample monitoring structure is advantageously used in automated processing and analytical evaluation of large numbers of fluid samples over extended periods of time (Continued)

analytical evaluation systems, including flow cytometry systems, live cell imaging and analysis systems and parallel bioreactor system. The sample monitoring structure may be in a form of sample monitoring beads for addition to liquid media of fluid samples subjected to analytical evaluation.

24 Claims, 13 Drawing Sheets

(58) Field of Classification Search
CPC ........... G01N 15/01; G01N 2015/1006; G01N 2015/1438; G01N 15/1459
See application file for complete search history.

(56) References Cited

U.S. PATENT DOCUMENTS

| | | | |
|---|---|---|---|
| 9,976,974 | B2 | 5/2018 | Nguyen et al. |
| 10,888,829 | B2 | 1/2021 | Sarma et al. |
| 2005/0008828 | A1* | 1/2005 | Libera .................... B82Y 30/00 |
| | | | 427/551 |
| 2005/0112655 | A1 | 5/2005 | Banerjee et al. |
| 2005/0239210 | A1 | 10/2005 | Iida |
| 2009/0190135 | A1 | 7/2009 | Clarizia et al. |
| 2010/0318070 | A1 | 12/2010 | Mitra et al. |
| 2012/0070818 | A1 | 3/2012 | Rowlen et al. |
| 2013/0316442 | A1* | 11/2013 | Meurville .......... G06K 7/10366 |
| | | | 435/287.5 |
| 2017/0219601 | A1* | 8/2017 | Bergo .............. G01N 33/54373 |
| 2018/0052163 | A1 | 2/2018 | Artinger et al. |
| 2018/0087021 | A1 | 3/2018 | Blanchard |
| 2020/0140690 | A1* | 5/2020 | Gamsey .............. C09B 23/0066 |
| 2021/0065362 | A1 | 3/2021 | Appledorn et al. |
| 2021/0325309 | A1 | 10/2021 | Neagle et al. |

OTHER PUBLICATIONS

Ge, Minghao et al., "A hyaluronic acid fluorescent hydrogel based on fluorescence resonance energy transfer for sensitive detection of hyaluronidase", Analytical and Bioanalytical Chemistry, vol. 412, No. 8, Feb. 7, 2020, pp. 1915-1923 (9 pages).
Caliari , et al., "A practical guide to hydrogels for cell culture", Nature Methods, vol. 13, No. 5, May 2016, pp. 405-414, 10 pages.
Esibio , "Fluorescent Labeling Hydrogels", downloaded Sep. 30, 2020 at https://esibio.com/support/product-documentation/protocols/fluorescent-labeling-hydrogels, 2 pages.

Essen Bioscience, Inc., "Incucyt® Empower Live-Cell Analysis Inside Your Incubator", www.Sartorius.com/Incucyte, Brochure, 2020, 7 pages.
Essen Bioscience, Inc., "Incucyt® Reagents, Consumables and Software", www.Sartorius.com/Incucyte, Brochure, 2021, 20 pages.
Essen Bioscience, Inc., "iQue®3 Faster, Smarter Flow Cytometry", Version Jul. 2020, www.sartorius.com/intellicyt, Brochure, 2020, 12 pages.
Gun'ko , et al., "Properties of Water Bound in Hydrogels", Gels, 3, 37, MDPI, www.mdpi.com/journal/gels, Oct. 19, 2017, 30 pages.
Himedia Laboratories Pvt. Ltd. , "Dulbecco's Modified Eagle Medium (DMEM)", www.higmedialabs.com, Product Code: AT068, Literature, 2011, 2 pages.
Horkay , et al., "Separation of the effects of pH and polymer concentration on the swelling pressure and elastic modulus of a pH-responsive hydrogel", NIH Public Access, 47(21), Oct. 4, 2006, pp. 7335-7338, 10 pages.
McKenzie , et al., "Core (Polystyrene)-Shell [Poly(glycerol monomethacrylate)] Particles", ACS Appl. Mater. Interfaces, 9, 2017, pp. 7577-7590, 14 pages.
Ozturk, et al., "Effect of Medium Osmolarity on Hybridoma Growth, Metabolism, and Antibody Production", Biotechnology and Bioengineering, vol. 37, 1991, pp. 989-993, 5 pages.
Rees-Manley , et al., "Evaluating Integrated Analytics for Single-use Mini Bioreactors", Whitepaper, American Pharmaceutical Review, www.americanpharmaceuticalreview.com, 2019, 4 pages.
Richter , et al., "Review on Hydrogel-based pH Sensors and Microsensors", Sensors 2008, 8, MDPI, www.mdpi.org/sensors, 2008, pp. 561-581, 21 pages.
Sartorius , "Ambr®15 Cell Culture Generation 2 Advanced Microbioreactor System", Version Mar. 2020, www.Sartorius.com, Brochure, 2020, 16 pages.
Sartorius , "Ambr®250 High Throughput Fully Automated for Accelerated Process Development", Version Apr. 2020, www.Sartorius.com, Brochure,, 2020, 12 pages.
Sigma-Aldrich , "DMEM, w/o phenol red, w/o L-glutamine, w/sodium pyruvate", (Dulbecco's Modified Eagle's Medium), Media Lab Product #: 21-500, Product Literature, www.sigma-aldrich.com, 2013, 3 pages.
Wang , et al., "Quantitating Fluorescence Intensity From Fluorophores: Practical Use of MESF Values", J. Res. Natl. Inst. Stand. Technol., vol. 107, No. 4, 2002, pp. 339-353, 15 pages.
Wolfbeis, Otto S., "An overview of nanoparticles commonly used in fluorescent bioimaging", Chem. Soc. Rev., 44, Royal Society of Chemistry, 2015, pp. 4743-4769, 26 pages.
Zhang, et al., "Novel Flow Cytometry Compensation Standards: Internally Stained Fluorescent Microspheres With Matched Emission Spectra and Long-Term Stability", Cytometry 33, 1998 Wiley-Liss, Inc., 1998, pp. 244-248, 5 pages.

* cited by examiner

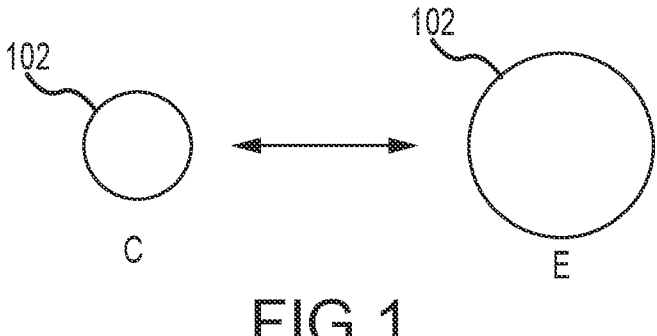
FIG.1
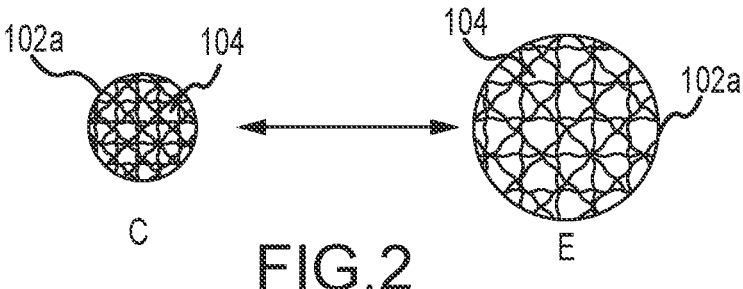
FIG.2
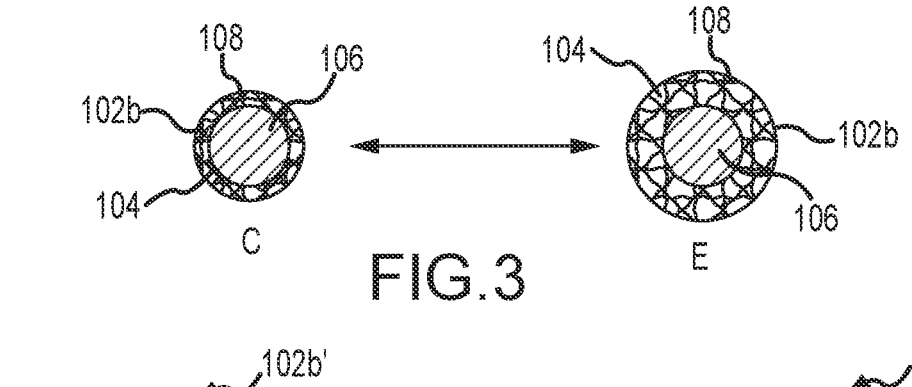
FIG.3
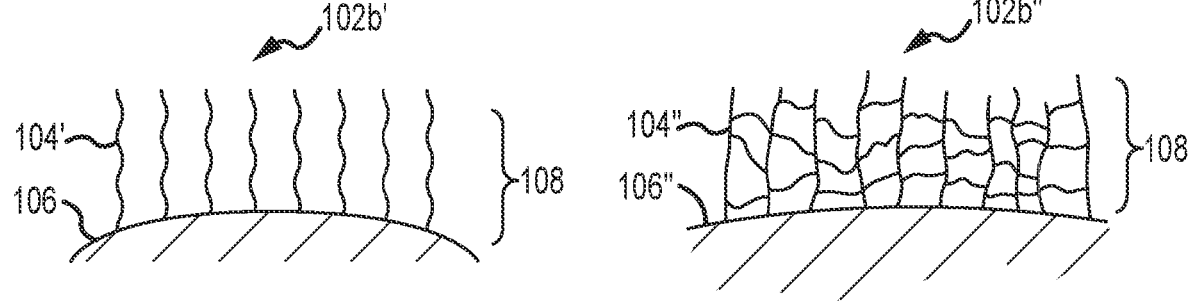
FIG.4                    FIG.5

ANALYTICAL EVALUATION OF AQUEOUS LIQUID MEDIA WITH SAMPLE MONITORING STRUCTURE HAVING SIZE-SENSITIVE FLUORESCENT HYDROGEL

CROSS-REFERENCE TO RELATED APPLICATIONS

This application claims the benefit of U.S. provisional patent application No. 63/151,252 entitled "FLOW CYTOMETRY EVALUATION WITH FLUID SAMPLE MONITORING BEADS HAVING SIZE-SENSITIVE FLUORESCENT HYDROGEL" filed Feb. 19, 2021, the contents of which are incorporated by reference herein for all purposes. This application claims the benefit of European patent application no. 21158037.8 entitled "FLOW CYTOMETRY EVALUATION WITH FLUID SAMPLE MONITORING BEADS HAVING SIZE-SENSITIVE FLUORESCENT HYDROGEL" filed with the European Patent Office on Feb. 19, 2021, the contents of which are incorporated by reference herein for all purposes.

FIELD

The invention relates to analytical evaluation of properties of aqueous liquid media with a sample monitoring structure having size-sensitive fluorescent hydrogel, including use in flow cytometry and other analytical evaluations in which the sample monitoring structure is in the form of sample monitoring beads mixed with an aqueous liquid medium.

BACKGROUND

High throughput flow cytometry is a technique in which a large number of fluid samples are prepared and subjected to flow cytometry evaluation sequentially in an automated flow cytometry system until all of the samples have been processed. Such automated flow cytometry systems may run for several hours or even multiple days, processing hundreds or thousands of fluid samples in an uninterrupted operation of the automated flow cytometry system. Examples of high throughput, automated flow cytometry systems include the iQue® flow cytometry screening systems. For example, the iQue® 3 flow cytometry screening system includes a flow cytometer with an integral autosampler capable of processing 96, 384 or 1536-well plates, and the system may be operated continuously for up to 48 hours and can process a 96-well plate in approximately 5 minutes and a 384-well plate in approximately 20 minutes.

Such high throughput, automated flow cytometry techniques are especially valuable for rapid screening of fluid samples. For example, many fluid samples may be rapidly screened to identify fluid samples that contain target particles of interest, or to identify fluid samples that contain at least a threshold amount of the target particles, for example for further investigation, or to compare concentrations of target particles between fluid samples. One example is for rapid pharmacological screening in antibody discovery and development, adoptive cell therapy or immune-oncology and small molecule discovery. As another example, rapid screening of many fluid samples may be performed to evaluate the effects of different manufacturing conditions for preparation of biologics (e.g., different processing conditions during cell culturing, harvesting and/or handling operations). For example, many fluid samples derived from different processing conditions may be rapidly screened for optimization of manufacturing variables for enhanced yield, cost reduction, enhanced product grade and/or other purposes.

Although the use of such high throughput, automated flow cytometry techniques have achieved significant success, especially for rapid screening applications, such techniques have some limitations. One problem with such techniques is that fluid samples may sit and wait for several hours or even days in a storage system awaiting flow cytometry processing in a screening sequence. During that time the fluid samples may be susceptible to chemical changes that can negatively affect flow cytometry results and can lead to misleading comparisons between flow cytometry results of fluid samples run at different times during a long duration of continuous operation. For example, salt concentrations and osmolarity of fluid samples may increase over time due to evaporation of water from fluid samples during long storage periods. As another example, the pH of fluid samples may decrease over time due to a build-up of acidic metabolites generated by biological material in the fluid samples. Even relatively small changes in such variables may detrimentally impact flow cytometry performance and the validity of screening comparisons between fluid samples run at different times during a high throughput screening run and may lead to incorrect conclusions concerning desirable biological manufacturing conditions. Current trends are toward development of high throughput, automated flow cytometry systems that can run for even longer continuous periods of operation to process even larger numbers of fluid samples, and problems with fluid sample degradation may be expected to become even more pronounced.

Similar trends are also occurring in other areas of analytical evaluation with movement toward automated processing and analytical evaluation of increasingly large numbers of fluid samples over extended periods of time, and similar fluid sample degradation issues also apply. Some examples of such other systems include parallel bioreactor systems designed to automatically operate many experimental bioreactors simultaneously over an extended time to simultaneously test and evaluate different bioreaction operating conditions. Some other examples of such other systems include live cell imaging and evaluation systems designed to incubate with automated evaluation over an extended time a large number of cell cultures to simultaneously test and evaluate different cell culture conditions.

SUMMARY

Disclosed herein are sample monitoring structures, and methods of analytical evaluation and analytical evaluation systems employing such sample monitoring structures. The sample monitoring structure comprises a fluorescently-labeled hydrogel that changes in size in response to a change of one or more properties of an aqueous liquid medium contacted with the fluorescently-labeled hydrogel. The fluorescently labeled hydrogel exhibits a fluorescent emission in response to a stimulation radiation and the intensity of the fluorescent response changes with changes in the size of the fluorescently-labeled hydrogel. The sample monitoring structure may be in any convenient form for a particular analytical evaluation application, but in some preferred implementations, the sample monitoring structure is in the form of sample monitoring beads including the fluorescently-labeled hydrogel, which sample monitoring beads can advantageously be dispersed in a liquid medium to be analytically evaluated. In some implementations the sample monitoring beads can be added to a liquid medium to monitor the properties and integrity of the liquid medium over time and to identify changes in properties that may raise an issue of sample integrity with the aqueous liquid medium.

In some preferred implementations, such sample monitoring beads can be included in flow cytometry fluid samples to monitor fluid sample integrity during flow cytometry evaluation, which are especially useful for identifying changes in aqueous fluid sample properties over extended timeframes that can be encountered during high throughput, automated flow cytometry screening operations. The sample monitoring beads include fluorescently-labeled hydrogel that is size-responsive to changes in one or more properties of the fluid samples, wherein the size of the fluorescently-labeled hydrogel, and consequently of the sample monitoring beads, changes in response to a change in one or more properties of the fluid sample, and wherein an intensity of a fluorescent emission from the sample monitoring beads during flow cytometry changes with changes in size of the fluorescently-labeled hydrogel. As a consequence, detected intensity of the fluorescent emission from the sample monitoring beads may be evaluated during flow cytometry to assess whether the properties of the fluid sample as subjected to flow cytometry are different from expected properties for the fluid sample. For example, an assessment may be made as to whether the fluid sample has degraded since the fluid sample was initially prepared, and whether the degradation is to an extent to call into question the integrity of the fluid sample and the validity of flow cytometry results for the fluid sample. A fluid sample integrity issue may, for example, result from a change over time in the chemical properties of the fluid sample, such as changes in salt concentration, osmolarity and/or pH of the fluid sample to an extent that may negatively affect the accuracy of flow cytometry results for the fluid sample and therefore the validity of those flow cytometry results for consideration as part of a screening evaluation.

Although flow cytometry is one important objective for advantageous use of the sample monitoring structures, and especially in the form of the sample monitoring beads, the sample monitoring structures may be used in other analytical applications in which the sample monitoring structures are mixed with, or otherwise contacted with or sequestered within, an aqueous liquid medium to monitor the aqueous liquid medium over time. Some other example applications for use of the sample monitoring structures include to monitor properties of growth media in biological processes (e.g., cell culture media or fermentation media), with two preferred such implementations comprising monitoring of growth media in live cell imaging and analysis systems and parallel bioreactor systems.

Also, except in analytical situations requiring a particulate form, such as for flow cytometry applications when the sample monitoring structure is to be detected in a fluid sample flow, the sample monitoring structure can be in a different form than the particulate form of the sample monitoring beads. For example, the sample monitoring structure can be in a monolithic form or in the form of a layer covering a surface of a fixed substrate. However, even in analytical situations not requiring the sample monitoring structure to be in the form of the sample monitoring beads, using the sample monitoring beads can be advantageous due to the high surface area of the sample monitoring beads leading to a quick response time to changes in an aqueous liquid medium. A significant advantage of the sample monitoring beads is that they can be dispersed a fluid sample of interest to provide a more representative analysis throughout a volume of fluid sample and/or while also permitting contemporaneous evaluation of other properties or components of the fluid sample. In some situations, however, it may be desirable to immobilize the sample monitoring structure when dispersion of sample monitoring beads in a liquid medium may be incompatible with a desired chemical or physical environment of a particular situation, for example when dispersed sample monitoring beads would interfere with desired chemical reactions or rheological properties of a fluid system. In such situations, the sample monitoring beads may be immobilized or sequestered in an investigation zone by attaching or otherwise retaining the sample monitoring beads adjacent to a fixed substrate surface contacted by the fluid of interest, thereby benefiting from the high surface area of the bead form, or the sample monitoring structure may be provided in an immobilized monolithic structure or as a surface layer on a fixed substrate.

One aspect of this disclosure is directed to a method for evaluation of at least one property of an aqueous liquid medium, the method comprising analytical evaluation of an aqueous liquid medium, wherein the analytical evaluation comprises:

contacting the aqueous liquid medium in an investigation zone with a sample monitoring structure comprising a fluorescently-labeled hydrogel that changes in size in response to a change in at least one property of the liquid medium, and in response to a stimulation radiation the sample monitoring structure has a fluorescent emission that changes in intensity with changes in the size of the fluorescently-labeled hydrogel; and with the liquid medium in the investigation zone in contact with the fluorescent hydrogel, subjecting the fluorescent hydrogel to the stimulation radiation and detecting the intensity of the fluorescent emission from the sample monitoring structure.

Some example analytical applications for the method of this aspect of the disclosure include use of the sample monitoring structure to evaluate properties of an aqueous liquid medium in connection with flow cytometry applications, live cell imaging applications and parallel reactor systems, although use of the sample monitoring structure is not limited to those exemplified analytical applications.

In another aspect, this disclosure is directed to an analytical system for analytical evaluation of at least one property of an aqueous liquid medium, the analytical system comprising:

a sample monitoring structure comprising a fluorescently-labeled hydrogel that changes in size in response to a change in at least one property of an aqueous liquid medium in contact with the fluorescently-labeled hydrogel, and in response to stimulation radiation the sample monitoring structure has a fluorescent emission that changes in intensity with changes in the size of the fluorescently-labeled hydrogel;

an investigation zone configured to receive the liquid medium in contact with the sample monitoring structure for analytical evaluation of the liquid medium;

a radiation delivery system configured to provide the stimulation radiation to impinge on the sample monitoring structure for investigation of the liquid medium in the investigation zone; and a radiation detection system configured to detect response radiation for the fluorescent emission from the sample monitoring structure.

Some example analytical systems for this aspect of the disclosure include flow cytometry evaluation systems, live cell imaging and analysis systems and parallel bioreactor systems, although the analytical systems with which the sample monitoring structure can be use is not limited to those exemplified analytical systems.

In some preferred implementations, this disclosure is directed more particularly to use of the sample monitoring structure in the form of sample monitoring beads in flow cytometry evaluations.

Another aspect of this disclosure is directed to a method for flow cytometry evaluation of an aqueous fluid sample, with the method comprising:

subjecting an aqueous fluid sample to flow cytometry evaluation, wherein:

the fluid sample comprises a plurality of beads disposed in an aqueous liquid medium, the beads comprising a fluorescently-labeled hydrogel that changes in size in response to a change in at least one property of the fluid sample, and in response to stimulation radiation, the beads have a fluorescent emission that changes in intensity with changes in the size of the fluorescently-labeled hydrogel; and detecting the intensity of the fluorescent emission from the bead;

and optionally the flow cytometry evaluation may also comprise flowing the fluid sample through an investigation zone and in the investigation zone subjecting a flow of the fluid sample to stimulation radiation and detecting for response radiation from the investigation zone; and optionally the flowing may comprise passing at least 100 of the beads through the investigation zone in the fluid sample.

Another aspect of this disclosure is directed to a flow cytometry system for flow cytometry evaluation of a fluid sample, wherein the flow cytometry system comprises:

a flow cytometry investigation system, comprising:

an investigation zone configured to receive during a flow cytometry evaluation a flow of a fluid sample comprising a plurality of beads disposed in an aqueous liquid medium;

a radiation delivery system configured to provide stimulation radiation to the investigation zone for investigation of the fluid sample in the investigation zone; and a radiation detection system configured to detect response radiation from the fluid sample in the investigation zone in response to the stimulation radiation;

a sample delivery system configured to interface with a sample container containing the fluid sample and to withdraw from the sample container and transfer to the investigation zone an evaluation volume of the fluid sample for the flow cytometry evaluation;

a data evaluation and control system in communication with the radiation detection system, the data evaluation and control system comprising a computer processor and computer memory with stored instructions executable by the computer processor to evaluate detected radiation information from the radiation detection system during the flow cytometry evaluation;

and wherein:

the beads comprise a fluorescently-labeled hydrogel that changes in size in response to a change in at least one property of the fluid sample;

an intensity of a fluorescent emission from each said bead in the fluid sample in response to the stimulation radiation changes with changes in the size of the fluorescently-labeled hydrogel;

the radiation detection system is configured to detect a range of fluorescent emission intensities corresponding to a range of sizes of the beads in the fluid sample; and the data evaluation and control system is configured to evaluate an integrity of the fluid sample, including evaluating the detected response radiation from the beads in the fluid sample.

Another aspect of this disclosure is directed to a flow cytometry system, wherein the flow cytometry system comprises:

a flow cytometry investigation system;

a sample container;

an aqueous fluid sample contained in the sample container; and a sample delivery system configured to interface with the sample container and to withdraw from the sample container and transfer to the flow cytometry investigation system an evaluation volume of the fluid sample for flow cytometry evaluation;

and wherein:

the fluid sample comprises a plurality of beads disposed in an aqueous liquid medium;

each said bead comprises a fluorescently-labeled hydrogel that changes in size in response to a change in at least one property of the fluid sample; and in response to stimulation radiation, an intensity of a fluorescent emission from a said bead changes with changes in the size of the fluorescently-labeled hydrogel;

and optionally the flow cytometry system may include:

an investigation zone to receive the flow of the fluid sample during the flow cytometry evaluation;

a radiation delivery system configured to provide stimulation radiation to the investigation zone for investigation of the fluid sample in the investigation zone; and a radiation detection system configured to detect a response radiation from the fluid sample in the investigation zone in response to the stimulation radiation.

Another aspect of this disclosure is directed to an aqueous fluid sample for flow cytometry evaluation or for other analytical evaluation, wherein the fluid sample comprises:

an aqueous liquid medium, including a plurality of beads and other particles dispersed therein for flow cytometry or other analytical evaluation for a presence of target particles, the other particles being different than the beads;

the beads comprising a fluorescently-labeled hydrogel, wherein the beads have a fluorescent emission when subjected to a stimulation radiation, and the fluorescently-labeled hydrogel changes in size in response to a change in at least one property of the fluid sample; and in response to the stimulation radiation, the beads have a fluorescent emission that changes in intensity with changes in the size of the fluorescently-labeled hydrogel.

Another aspect of this disclosure is directed to a product for use in monitoring an aqueous fluid sample during flow cytometry evaluation or other analytical evaluation of the fluid sample, wherein the product comprises:

a plurality of beads for inclusion in an aqueous liquid medium of an aqueous fluid sample to monitor the fluid sample during flow cytometry or other analytical evaluation, the beads having a fluorescent emission when subjected to a stimulation radiation during flow cytometry or other analytical evaluation, and each said bead comprising:

a non-hydrogel core and a shell layer of fluorescently-labeled hydrogel surrounding the core;

wherein the fluorescently-labeled hydrogel changes in size in response to a change in at least one property of the aqueous fluid sample; and wherein an intensity of the fluorescent emission from the bead changes with changes in the size of the fluorescently-labeled hydrogel.

Another aspect of this disclosure is directed to a product for use in monitoring an aqueous fluid sample during flow cytometry evaluation or other analytical evaluation of the fluid sample, wherein the product comprises:

a plurality of beads for inclusion in an aqueous liquid medium of an aqueous fluid sample to monitor the fluid sample during flow cytometry or other analytical evaluation, the beads having a fluorescent emission when subjected to a stimulation radiation during flow cytometry or other analytical evaluation;

each said bead comprising a fluorescently-labeled hydrogel that is size-responsive in the aqueous liquid medium, wherein an intensity of the fluorescent emission from the bead changes with changes in the size of the fluorescently-labeled hydrogel; and the beads having reference-state properties in a reference-state aqueous composition, wherein the reference-state aqueous composition comprises the beads dispersed in the aqueous liquid medium and the reference-state properties comprise a reference-state particle size of the beads in a range of from 2 microns to 25 microns, and preferably in a range of from 3 microns to 15 microns.

Another aspect of this disclosure is directed to a product for use in monitoring an aqueous fluid sample during flow cytometry evaluation or other analytical evaluation of the fluid sample, wherein the product comprises:

a plurality of beads in an aqueous liquid medium of an aqueous fluid sample to monitor the fluid sample during the flow cytometry or other analytical evaluation, the beads having a fluorescent emission when subjected to a stimulation radiation during flow cytometry or other analytical evaluation;

each said bead comprising a fluorescently-labeled hydrogel that is size-responsive in the aqueous liquid medium, wherein an intensity of the fluorescent emission from the bead changes with changes in the size of the fluorescently-labeled hydrogel;

the fluorescently-labeled hydrogel comprises a plurality of a first fluorochrome moieties and a plurality of a second fluorochrome moieties;

the first fluorochrome moiety has a first fluorescent emission in response to the stimulation radiation and the second fluorochrome moiety has a second fluorescent emission, different than the first fluorescent emission, in response to stimulation by the first fluorescent emission; and the fluorescent emission of the beads comprises the second fluorescent emission, and the second fluorescent emission decreases as the size of the hydrogel increases with a corresponding increase in spacing between occurrences of the first fluorochrome moiety and occurrences of the second fluorochrome moiety. The second fluorescent emission may be a consequence of Forster Resonance Energy Transfer (FRET) between the first and second fluorochrome moieties.

The description herein is provided primarily with reference to the preferred flow cytometry applications, but the principles apply as well to use of the sample monitoring structure in other analytical evaluation applications, adapted as appropriate for the particular requirements of such other analytical evaluation applications. For example, properties and implementation alternatives for the sample monitoring beads disclosed herein with reference to flow cytometry applications apply as well to the sample monitoring beads as they may be used in other analytical evaluation applications, such as live cell imaging and parallel bioreactor systems. Likewise, manufacture of fluorescent hydrogel for inclusion in sample monitoring beads apply also for the sample monitoring structure prepared in a different physical form. For example, techniques disclosed herein for preparing fluorescently-labeled hydrogels on non-hydrogel cores for some forms of the sample monitoring beads apply also to preparing layers of fluorescently-labeled hydrogels on substrate surfaces of other forms, for example on a surface of an immobilized substrate.

Various other feature refinements and additional features are applicable to each of these and other aspects of this disclosure, as disclosed in the description below, the figures and the appended claims. These feature refinements and additional features may be used individually or in any combination within the subject matter any of the aspects summarized above or other aspects disclosed herein. Any such feature refinement or additional feature may be, but is not required to be, used with any other feature or a combination of features disclosed herein.

BRIEF DESCRIPTION OF THE DRAWINGS

FIG. 1 is an illustration of a sample monitoring bead including a size-responsive, fluorescent hydrogel, shown both in a more contracted state and in a more expanded state as a consequence of changes to aqueous liquid environment.

FIG. 2 is an illustration of an example of a sample monitoring bead comprised essentially of only size-responsive, fluorescent hydrogel, shown both in a more contracted state and in a more expanded state as a consequence of changes to aqueous liquid environment.

FIG. 3 is an illustration of a sample monitoring bead having a non-hydrogel core and a size-responsive, fluorescent hydrogel shell layer, shown both in a more contracted state and in a more expanded state as a consequence of changes to aqueous liquid environment.

FIG. 4 is an illustration of a surface portion of one example variation of a sample monitoring bead having a non-hydrogel core and a size-responsive, fluorescent hydrogel shell layer in which the hydrogel is not cross-linked.

FIG. 5 is an illustration of a surface portion of another example variation of a sample monitoring bead having a non-hydrogel core and a size-responsive, fluorescent hydrogel shell layer in which the hydrogel is cross-linked.

FIG. 12 is an illustration of steps I-II of an example method of making sample monitoring beads with size-responsive, fluorescent hydrogel in a shell layer around a non-hydrogel core.

FIG. 13 is an illustration of steps III-V of an example method of making sample monitoring beads with size-responsive, fluorescent hydrogel in a shell layer around a non-hydrogel core.

FIG. 14 is an illustration of step VI of an example method of making sample monitoring beads with size-responsive, fluorescent hydrogel in a shell layer around a non-hydrogel core.

DETAILED DESCRIPTION

Figure 6:
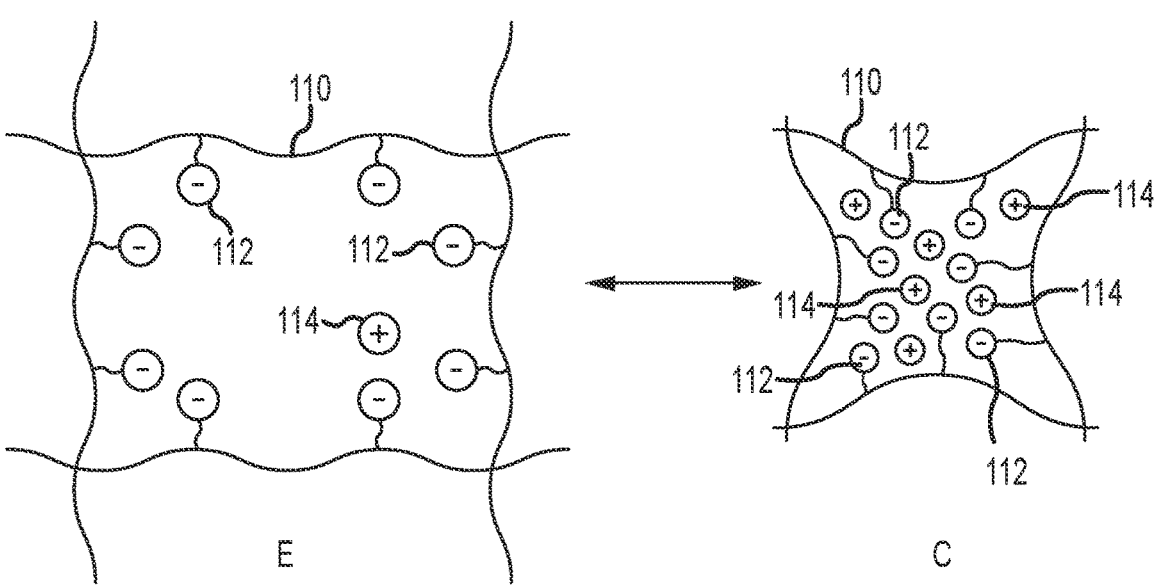
FIG. 6 is an illustration of a portion of an example size-responsive hydrogel including anionic functional groups, shown both in a more contracted state and in a more expanded state as a consequence of changes to aqueous liquid environment.

FIG. 1 shows an example flow cytometry sample monitoring bead 102 in which the size of the sample monitoring bead 102 is able to expand and contract in response to changes in one or more properties of an aqueous liquid medium of a fluid sample in which the sample monitoring bead 102 may be disposed for monitoring integrity of the fluid sample for flow cytometry evaluation. FIG. 1 shows the sample monitoring bead 102 in a more contracted state (C) and a more expanded state (E), which result from changes in particle size as a consequence of changes in one or more properties of the aqueous liquid medium. In the more expanded state (E), the sample monitoring bead 102 has an increased size as a consequence of greater swelling of the fluorescent hydrogel as the fluorescent hydrogel becomes hydrated to a larger degree. Conversely, in the more contracted state (C) the sample monitoring bead 102 has a smaller size as a consequence of a lower degree of hydration of the fluorescent hydrogel. The sample monitoring bead 102 illustrated in FIG. 1 may be a single-phase particle that consists essentially of only a hydrogel structure, or the sample monitoring bead 102 may be a multi-phase (composite) particle with multiple different material phases, one of which has a hydrogel structure and another one of which is comprised of a non-hydrogel material.

FIG. 2 illustrates one example variation of the sample monitoring bead 102 of FIG. 1, having a single-phase particle structure. As shown in FIG. 2, the example sample monitoring bead 102a consists essentially of only a single hydrogel material phase 104, and preferably with uniform properties throughout the sample monitoring bead 102a. As illustrated in FIG. 2, the hydrogel material phase 104 is in the form of a polymer network functionalized with fluorochrome and other functional groups as appropriate to provide the desired type and degree of size-responsiveness to changes in aqueous liquid medium for which the sample monitoring bead 102a is to be used, and with desired accompanying changes to fluorescent response intensity from the fluorochrome included in the hydrogel material phase 104. Because the example sample monitoring bead 102a of FIG. 2 is constructed of a single uniform hydrogel material phase, all portions of the sample monitoring bead exhibit uniform expansion and contraction with changes in aqueous liquid properties, as illustrated in the more contracted state (C) and the more expanded state (E) shown in FIG. 2.

When reference is made to the size of a bead, the reference is to a maximum cross-dimension of the bead. As illustrated in FIGS. 1 and 2, the example beads are generally of spherical shape, in which the size of the beads are the diameter of the sphere of the beads. However, the beads are not limited to spherical shape, and may be of any desired shape. Such shapes may for example be spherical, spheroidal, oblong, cubical, rod-shaped or any other shape.

FIG. 3 illustrates another example variation of the sample monitoring bead 102, having a multi-phase, composite particle structure. As illustrated in FIG. 3, the example sample monitoring bead 102b includes a core 106 of non-hydrogel material surrounded by a shell layer 108 consisting essentially of a hydrogel material phase 104. The core 106 may be porous or nonporous, and preferably does not substantially expand or contract with changes in the properties of aqueous liquid medium, in which case expansions and contractions in the size of the sample monitoring bead 102b are due substantially primarily to expansions and contractions of the hydrogel material phase 104 of the shell layer 108. As illustrated in FIG. 3, the shell layer 108 changes size between the more contracted state (C) and the more expanded state (E) while the core 106 remains essentially the same size or has only a very small amount of change in size.

Referring again to FIG. 2, the hydrogel material phase 104 of the sample monitoring bead 102a will typically be in the form of a cross-linked polymer network. The cross-linking in the polymer network maintains the hydrogel structure in a particle form and prevents the material of the hydrogel from dissipating from the particle structure in aqueous liquid medium. However, in the multi-phase particle structure of the example sample monitoring bead 102b illustrated in FIG. 3, the hydrogel material phase 104 of the shell layer 108 will typically be attached to the core 106, which will retain the hydrogel material phase in the particle structure and prevent the material of the hydrogel dissipating from the particle structure in aqueous liquid medium. Consequently, the material of the hydrogel material phase 104 in the shell layer 108 need not be cross-linked, other than through the attachment to the core 106, to retain the hydrogel material in the multi-phase particle structure.

FIGS. 4 and 5 illustrate two different example structures for the hydrogel material phase 104 in the multi-phase particle structure of FIG. 3. Referring first to FIG. 4, the shell layer 108 of an example sample monitoring bead 102b' includes a hydrogel material phase 104' in the form of a brush-like covering of the core 106 with polymer strands attached to the core 106, but otherwise not cross-linked. In contrast, the shell layer 108 of the example sample monitoring bead 102b" shown in FIG. 5 includes a hydrogel material phase 104" in the form of a cross-linked polymer network. The polymer of the hydrogel is attached to the core 106, similar to the embodiment illustrated in FIG. 4, but the polymer of the hydrogel is also cross-linked in the shell layer 108. For equivalent hydrogel compositions, other than the presence or absence of cross-linking, the lack of cross-linking in the shell layer in FIG. 4 generally permits a greater degree of expansion and contraction of the hydrogel material phase 104' in response to changes in properties of aqueous liquid medium than the hydrogel material phase 104" of FIG. 5, as a consequence of the shape-retaining influence of cross-linking in the hydrogel material phase 104" of FIG. 5. A greater degree of cross-linking will impart greater resistance to hydrogel size changes and a smaller degree of cross-linking will impart lesser resistance to hydrogel size changes.

Changes in size of the hydrogel of the sample monitoring beads of this disclosure may be a consequence of a change in one or more properties of the aqueous liquid medium. FIG. 6 shows a portion of an example hydrogel 110, illustrated in both a more expanded state (E) and a more contracted state (C), in which hydrogel 110 includes negatively charged ionic functional groups 112 (anionic groups) in a cross-linked polymer network. The negatively charged ionic functional groups 112 contribute to size-change responsiveness of the hydrogel 110 in response to changes in salt concentration and changes in osmolarity in an aqueous liquid medium. As will be appreciated, an increase in salt concentration generally also leads to an increase in osmolarity. In the more expanded state (E) of the hydrogel 110 illustrated in FIG. 6, the hydrogel is in the presence of an aqueous liquid medium with a smaller salt concentration than the more contracted state (C), represented by the presence of only a single positively charged ion 114 (cation) in the more expanded state (E) and a larger number of the positively charged ions 114 in the more contracted state (C). In the more expanded state (E), the repulsion of the negatively charged ionic groups 112 contributes to a relative swelling of the hydrogel 110. In the more contracted state, the repulsive force of a greater number of the negatively charged ionic groups is shielded through the presence of ion pairing with the more positively charged ions 114 as a consequence of the increased salt concentration (or increased osmolarity), contributing to a relative contraction of the hydrogel 110.

Figure 7:
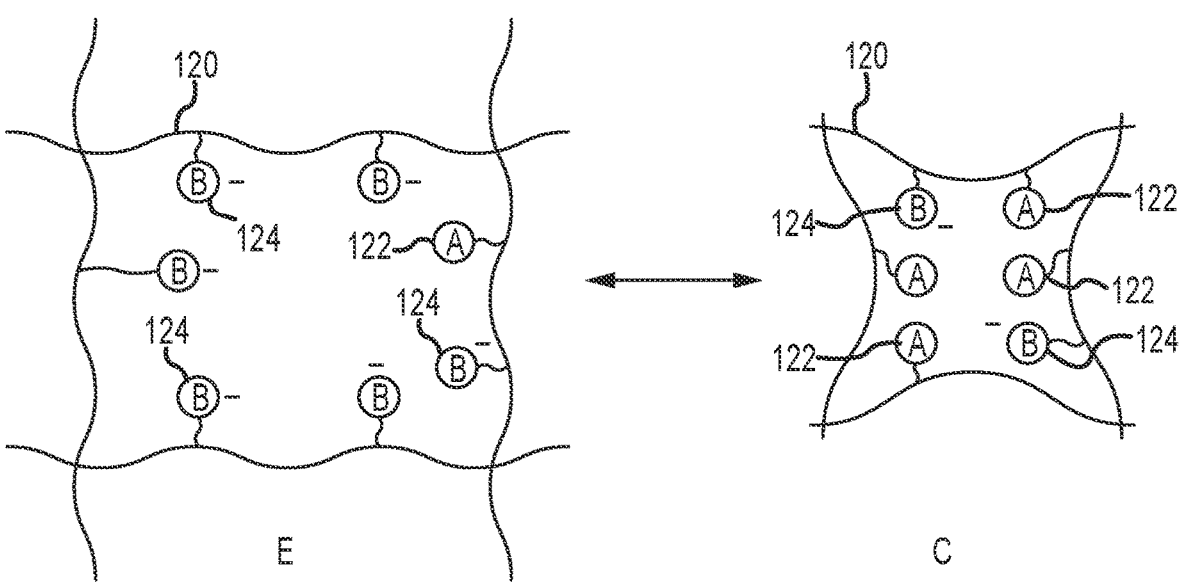
FIG. 7 is an illustration of a portion of an example size-responsive hydrogel including functional groups that are convertible from acid groups to conjugate base groups, shown both in a more contracted state and in a more expanded state as a consequence of changes to aqueous liquid environment.

FIG. 7 shows a portion of an example hydrogel 120, illustrated in both a more expanded state (E) and a more contracted state (C), in which the hydrogel 120 includes acid functional groups 122 and conjugate base functional groups 124. A conjugate base functional group 124 is a negatively charged ionic group that is a conjugate base of an acid functional group 122, formed by dissociation of a proton ($H^+$) from the acid functional group 122. One example of such an acid functional group is a carboxylic acid group (—C(O)OH) with the conjugate base functional group being a carboxylate ionic group (—C(O)O$^-$). In the more expanded state (E) illustrated in FIG. 7, the aqueous liquid is at a higher pH with most of the acid/base functional groups in the form of the conjugate base functional groups 124, in which the negatively charged conjugate base functional groups 124 are repelled from each other and contribute to relative swelling of the hydrogel 120 with increasing pH. In the more contracted state (C) the aqueous liquid is at a lower pH, where most of the acid/base functional groups are in the protonated form of the acid functional groups 122, reducing the relative repulsive forces of negatively charged conjugate base functional groups 124 and contributing to relative expansion of the hydrogel 120 with increasing pH.

Figures 8, 11:
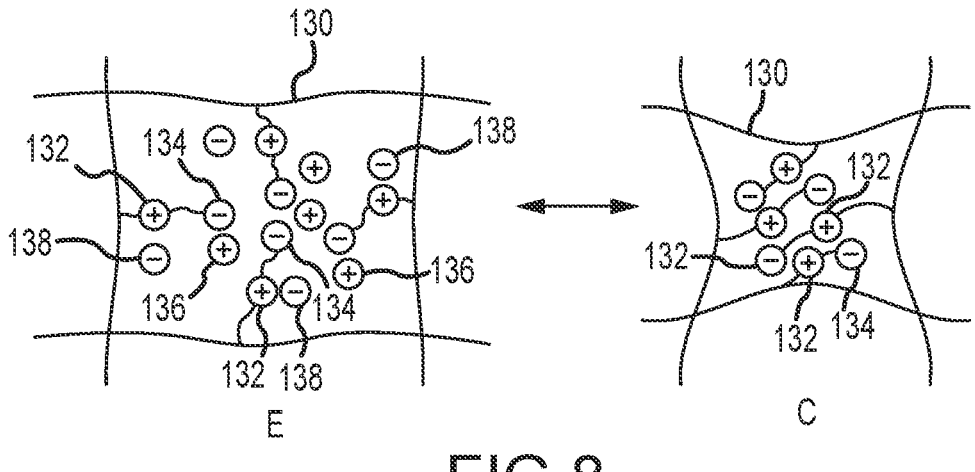
FIG. 8 is an illustration of a portion of an example size-responsive hydrogel including zwitterionic functional groups, shown both in a more contracted state and in a more expanded state as a consequence of changes to aqueous liquid environment.
FIG. 11 is an illustration of the chemical formula of the repeating unit of poly(glycidyl methacrylate).

FIG. 8 shows a portion of an example hydrogel 130, illustrated in both a more expanded state (E) and more contracted state (C), in which the hydrogel 130 includes zwitterionic functionality, with both positively charged functional groups 132 and negatively charged functional groups 134 in a cross-linked polymer network. The zwitterionic functionality contributes to size-change responsiveness of the hydrogel 130 in response to changes in salt concentration and changes in osmolarity in aqueous liquid medium. In the more expanded state (E), the hydrogel 130 is in the presence of an aqueous liquid medium with a higher salt concentration than in the more contracted state (C), as represented by the presence of several cations 136 and anions 138 of dissociated salt in the hydrogel 130. In particular, the association of the positively charged functional groups 132 and the negatively charged functional groups 134 of the hydrogel 130 is interrupted and reduced by the presence of the cations 136 and the anions 138 from the higher salt concentration. In contrast, in the more contracted state (C), at lower salt concentration, the positively charged functional groups 132 and the negatively charged functional groups 134 tend to associate in ion pairs that contribute to a relative contraction of the hydrogel 130.

The hydrogel of the sample monitoring beads is fluorescent, and accordingly is sometimes referred to herein as a fluorescently-labeled hydrogel or more simply as a fluorescent hydrogel, which terms are used equivalently in this disclosure. In addition to having one or more functionalities that contribute to size-change responsiveness, the sample monitoring beads of the present disclosure will typically include at least one fluorochrome in the hydrogel to impart fluorescent activity to the sample monitoring beads, with the fluorescent emission from the sample monitoring beads changing with changes in the size of the hydrogel. A sample monitoring bead may have only a single type of fluorochrome or may have multiple different types of fluorochromes that have different fluorescent emission wavelengths. The sample monitoring beads may be prepared to exhibit decreased fluorescent emission intensity as the hydrogel expands (increased fluorescent emission as the hydrogel contracts). Alternatively, the sample monitoring beads may be prepared to exhibit decreased fluorescent emission intensity as the hydrogel contracts (increased fluorescent emission intensity as the hydrogel expands), depending on the properties of the hydrogel and the nature of fluorochromes incorporated into the hydrogel.

Figure 9:
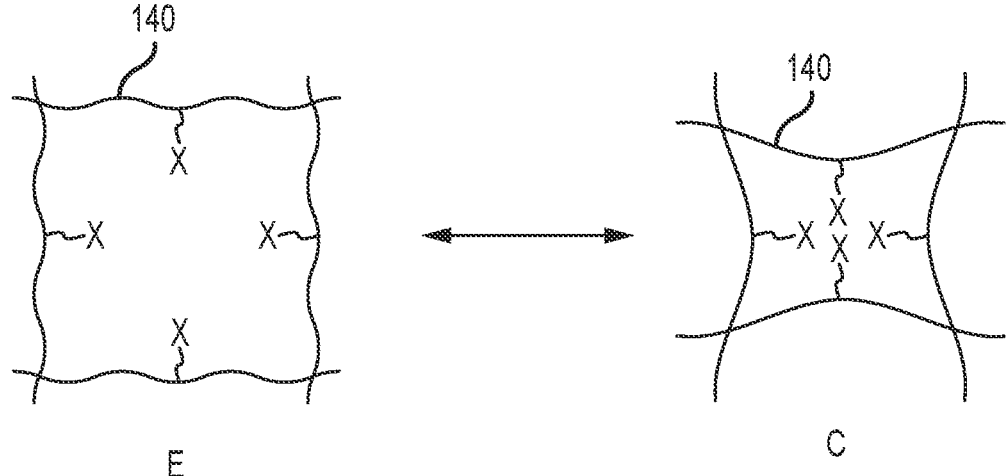
FIG. 9 is an illustration of a portion of an example size-responsive hydrogel including a fluorochrome moiety, shown both in a more contracted state and in a more expanded state as a consequence of changes in aqueous liquid environment.

FIG. 9 illustrates an example of a hydrogel 140 for which fluorescent emission intensity from the hydrogel 140 increases as the hydrogel 140 expands, and conversely the fluorescent emission intensity from the hydrogel 140 decreases as the hydrogel 140 contracts. As shown in FIG. 9, the hydrogel 140 includes a fluorochrome, represented as a fluorochrome moiety (X). The fluorochromes of the fluorochrome moieties (X) exhibit a fluorescent emission in response to a stimulation radiation. In the more contracted state, the average spacing between the fluorochrome moieties (X) is smaller (the fluorochrome moieties are closer together) than in the more expanded state (E). As a consequence of the closer spacing of the fluorochrome moieties in the more contracted state (C), more of the emission from the fluorochromes is consumed through quenching by other nearby fluorochromes, and the fluorescent emission intensity from the hydrogel 140 decreases due to fluorescent signal losses. In contrast, in the expanded state (E), the average spacing between the fluorochrome moieties (X) is larger (the fluorochrome moieties are farther apart) than in the contracted state (C), and as a consequence less fluorescent signal is lost to quenching and the detectable fluorescent emission intensity is larger in the expanded state (E) than in the contracted state (C).

Figure 10:
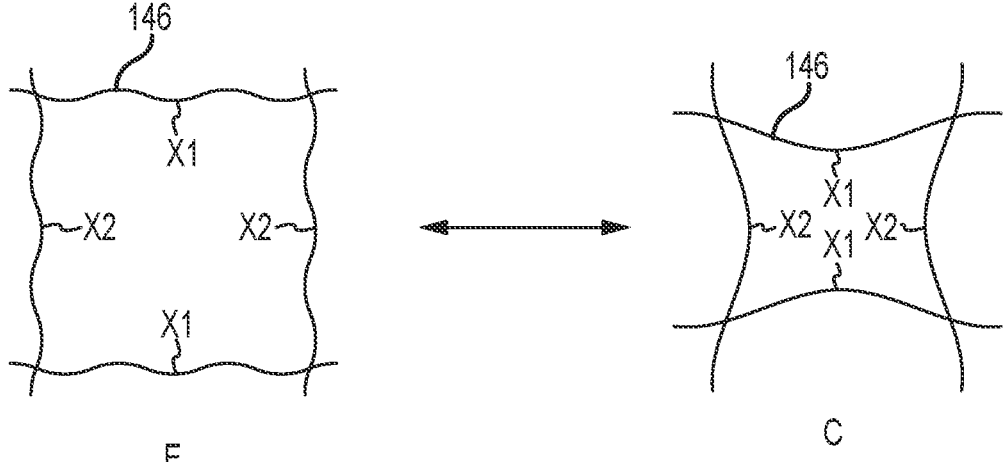
FIG. 10 is an illustration of a portion of an example size-responsive hydrogel including multiple different fluorochrome moieties having different fluorescent emission characteristics and providing a FRET fluorescence capability, shown both in a more contracted state and in a more expanded state as a consequence of changes in aqueous liquid environment.

FIG. 10 illustrates an example of a hydrogel 146 for which the fluorescent emission intensity from the hydrogel 146 decreases as the hydrogel 146 expands, and conversely the fluorescent emission intensity from the hydrogel 146 increases as the hydrogel 146 contracts, through incorporation of a Forster Resonance Energy Transfer (FRET) capability in the hydrogel 146. Forster Resonance Energy Transfer is also referred to as Fluorescent Resonance Energy Transfer. The hydrogel 146 includes fluorochromes of a first type, represented as first fluorochrome moieties (X1) and fluorochromes of a different, second type, represented as second fluorochrome moieties (X2). First fluorochromes of the first fluorochrome moieties (X1) have a first fluorescent emission from excitation radiation provided by a flow cytometer to the investigation zone during flow cytometry evaluation. Second fluorochromes of the second fluorochrome moieties (X2) excite at a different excitation wavelength than the fluorochromes of the first fluorochrome moieties (X1), such that the second fluorochromes are excited by the fluorescent emission from the first fluorochromes. The second fluorochrome moieties (X2) provide a second fluorescent emission that is different (at a different peak emission wavelength) than the first fluorescent emission of the first fluorochrome moieties (X1). The second fluorescent emission may be detected during flow cytometry evaluation to provide information on the properties of aqueous liquid medium of the fluid sample. As shown in FIG. 10, in the more expanded state (E) of the hydrogel 146, the average spacing between occurrences of the first fluorochrome moieties (X1) and the second fluorochrome moieties (X2) is larger than in the more contracted state (C) of the hydrogel 146. As a consequence, the first fluorescent emission from the first fluorochrome moieties (X1) becomes more attenuated before encountering and exciting a second fluorochrome moiety (X2) in the more expanded state (E) relative to the more contracted state (C), and as a consequence the second fluorescent emission from the hydrogel 146 will have a higher intensity in the more contracted state (C) than in the in the more expanded state (E).

As will be appreciated, the features of any of the hydrogels of any of FIGS. 6-8 that contribute to size-responsiveness may be combined with either of the fluorochrome configurations of FIG. 9 or 10. Also, the fluorochrome features of FIGS. 9 and 10 may be combined together in a hydrogel. For example, a hydrogel may be prepared to include a fluorochrome with a fluorescent emission response to be detected during flow cytometry, in which the intensity of the fluorescent emission decreases as the hydrogel contracts, and the hydrogel may also include a separate FRET pair of fluorochromes that provide a different fluorescent emission (with a different peak emission wavelength) with an intensity of the fluorescent emission that increases as the hydrogel contracts.

FIGS. 6-10 are illustrated with hydrogels including cross-linking, such as in the hydrogel material phase 104 in the example of FIG. 2 or the hydrogel material phase 104" in the example of FIG. 5. However, the features and concepts illustrated in FIGS. 6-10 are equally applicable to hydrogels not including cross-linking, such as in the hydrogel material phase 104' in the example of FIG. 4.

As will be appreciated, the properties of the beads will vary depending upon the conditions of the aqueous liquid medium to which the beads are subjected, as a consequence of changes in size of the hydrogel with changing properties of the aqueous liquid medium. However, for quality control and practical manufacture and testing purposes, properties of the beads may be described relative to a reference set of conditions for a representative aqueous liquid medium, and relative to changes in those reference-state properties as a consequence of a changes to the reference set of conditions to a modified set of conditions in a modified aqueous liquid medium. The presence of the beads in the aqueous liquid medium having the reference set of conditions may be referred to as a reference state for the beads and the properties of the beads in that reference state may be referred to as the reference-state properties. Likewise, the presence of the beads in the aqueous liquid medium having the modified set of conditions may be referred to as the modified state and the properties of the beads in the aqueous liquid medium having the modified set of conditions may be referred to as the modified-state properties. The conditions for the reference state and modified state may advantageously be identified relative to anticipated conditions in fluid sample monitoring situations for which any particular batch of beads may be designed for use. For example, a particular product batch of beads may be identified as having reference-state properties at conditions of an aqueous liquid medium representative of conditions at which fluid samples containing the beads are anticipated to be prepared for flow cytometry. The modified-state properties may then represent properties of the beads under some set of conditions modified to some degree from conditions of the reference state so that the modified-state properties provide a useful measure of the sensitivity of changes in properties of the beads, and in particular sensitivity of changes in size and relative fluorescence intensity, over a meaningful increment of change under which the beads are designed to operate to monitor changes in fluid sample properties. Some examples for sets of conditions for such a reference state and corresponding modified state, and reference-state properties and modified-state properties of the beads are presented in the example implementation combinations provided below and in the appended claims.

Many polymers are known for making hydrogels, any of which may be used for the hydrogel of the sample monitoring beads. The hydrogel of the sample monitoring beads typically will include one or more primary polymers that impart a desired structure to the hydrogel. Such a primary structural polymer for the hydrogel of the sample monitoring beads may be provided by any polymer, or combination of polymers, useful for preparing hydrogels. The hydrogel may include a single structural polymer for the hydrogel, or a combination of multiple structural polymers, and any such structural polymer may be a homopolymer or a copolymer.

Copolymers may include repeating units from two or more than two different monomers, and may be in any form, such as block or random copolymers. Structural polymers may include polymers in various forms and shapes, including in the form of polymer chains, branched polymers, star polymers and/or dendritic polymers. When the hydrogel includes a cross-linked polymer network, the network may include any suitable cross-linking chemistry for such structural polymer or polymers of the hydrogel. Such cross-linking may involve covalently bonded linking groups or other physical or chemical interactions, such as hydrogen bonds, ionic interactions, hydrophobic interactions or polymer chain entanglements. Preferred cross-linking includes covalently bonded linking groups. In addition to one or more such primary structural polymers, the hydrogel may include one or more secondary polymers or polymer segments, typically present in a minority proportion, to impart any desired property or functionality to the hydrogel. Polymers within the hydrogel may be functionalized with any combination of functional groups conducive to the use of the hydrogel as a size-sensitive particle with variable fluorescent intensity for monitoring integrity of flow cytometry fluid samples. Some example polymers that may be used in the hydrogel of the sample monitoring beads, as primary structural polymers or secondary polymers, include vinyl polymers (e.g., polyvinyl alcohol), polyglycols (e.g., polyethylene glycol), acrylate (acrylic) polymers, methacrylate (methacrylic) polymers, and various natural polymers (e.g., collagen, gelatin and fibrin). Some preferred monomers for preparation of the hydrogel include acrylic and methacrylic monomers (also referred to as acrylate and methacrylate monomers). Examples of some acrylic and methacrylic monomers for polymers that may be used to prepare the hydrogel of the sample monitoring beads, whether or not the sample monitoring beads have a core-shell structure with the hydrogel in a shell layer attached to the core, include the following:

glycidyl methacrylate;
(hydroxyethyl)methacrylate;
2-acrylamido-2-methylpropane sulfonic acid;
(2-(methacryloyloxy)ethyl)trimethylammonium chloride;
acrylic acid;
2-aminoethyl methacrylate hydrochloride;
2-(diethylamino)ethyl methacrylate;
2-(dimethylamino)ethyl methacrylate;
2-isocyanatoethyl methacrylate;
[3-(methacryloylamino)propyl]trimethylammonium chloride;
[2-(methacryloyloxy)ethyl]dimethyl-(3-sulfopropyl)ammonium hydroxide;
3-sulfopropyl methacrylate;
2-ethylacrylic acid; and
2-propylacrylic acid.

Some example monomers useful to impart ion exchange functionality include:
2-acrylamido-2-methylpropane sulfonic acid;
(2-(methacryloyloxy)ethyl)trimethylammonium chloride;
2-(diethylamino)ethyl methacrylate;
2-(dimethylamino)ethyl methacrylate;
[3-(methacryloylamino)propyl]trimethylammonium chloride;
[2-(methacryloyloxy)ethyl]dimethyl-(3-sulfopropyl)ammonium hydroxide; and
3-sulfopropyl methacrylate.

Some example monomers useful to impart pH sensitivity include:
acrylic acid;
2-ethylacrylic acid; and
2-propylacrylic.

Some example monomers useful to provide reactive sites for further functionalization include:
glycidyl methacrylate;
2-isocyanatoethyl methacrylate; and
(hydroxyethyl)methacrylate.

Any acrylate, methacrylate, acrylamide, methacrylamide or N-alkylacrylamide analog of any of the foregoing example monomers may also or alternatively be used as a monomer.

Monomers may be selected that include functional groups desired in the hydrogel for a desired size-responsiveness and/or polymers may be functionalized with desired functional groups following polymerization. Functionalization of the hydrogel with one or more fluorochromes is typically performed after polymerization has been completed to form the structure of the hydrogel.

When the sample monitoring beads are in the form of a core-shell structure, the core may be provided in the form of pre-prepared particle beads of a desired size, over which the hydrogel of the film layer is formed. The core may be prepared specially for use in the sample monitoring beads or may be provided by a variety of commercially available particle beads, including polystyrene beads, agarose beads, Sepharose® beads, cellulose beads and latex beads, and with preferred beads including or treated to include available hydroxyl groups or amine groups at the surface.

In one approach, polymers for the hydrogel of the shell layer may be pre-prepared and then attached to the core (a "grafting to" approach). Attachment may be through covalent linkage or may be through physisorption to "sticky" functionality on the surface of the core. Cross-linking, if desired in the hydrogel, may be performed before or after polymer attachment to the core. If cross-linking is performed prior to polymer attachment, pre-prepared cross-linked units of polymer network may be attached to the surface, and after attachment such units may be further cross-linked to each other to provide a fully cross-linked polymer network.

In another approach, polymers are prepared in situ on the core by direct polymerization from initiation sites on the core (a "grafting from" approach). Polymerization may be controlled or uncontrolled. Initiation sites can be provided by direct radiation, such as ultraviolet-visible spectrum (UV-Vis), e-beam (electron radiation) or gamma-irradiation. As an alternative approach, initiation sites can be provided by immobilization of chemical initiators at the surface of the core particle, for example for use with free radical polymerization, atom transfer radical polymerization (ATRP) or reversible addition-fragmentation chain transfer (RAFT) polymerization. Via the initiation approach and the polymerization reaction conditions, the polymer layer architecture can be tailored regarding the degree of cross-linking, the chain length and density as well as polymer composition (e.g., co-polymerization).

ATRP is a common polymerization technique, as is surface initiated ATRP (SI-ATRP), which refers to ATRP in which polymerization is initiated from the surface of a substrate to which the polymer is to be anchored. SI-ATPR is one preferred approach for a controlled polymerization technique capable of generating on core particles polymer chain lengths with a narrow length distribution and at a controlled density on the surface of the core particles. In general, SI-ATRP includes immobilization of an initiator on the substrate surface (the surface of the core particle in this case) to act as an anchor for the resulting polymer. The substrate with initiator is then contacted with a monomer in an organic liquid composition in the presence of a transition metal salt (often copper) as a catalyst, which is typically solubilized in the organic liquid with a ligand. The organic liquid may typically comprise an organic solvent in which the monomer and catalyst are solubilized, although bulk polymerization in liquid monomer is also possible. The ATRP approach tolerates many monomers and also enables copolymerization. The approach is, however, sensitive to oxygen, and accordingly is typically performed under a nitrogen atmosphere. By varying the initiator on the substrate surface, the polymer chain density can be controlled. Copolymerization using bifunctional monomers additionally enables formation of cross-linked polymer chains for the hydrogel.

With reference primarily to FIGS. 12-15, an example will now be presented for preparation of sample monitoring beads with core particles and a fluorescent hydrogel shell layer including poly(glycidyl methacrylate) as a structural polymer for the hydrogel formed using SI-ATRP, and with post polymerization modification of the poly(glycidyl methacrylate) to provide charged group and fluorochrome functionality for a size-responsiveness to changes in salt concentrations and osmolarity. The repeating unit of poly (glycidyl methacrylate) is shown in FIG. 11.

Figure 12:
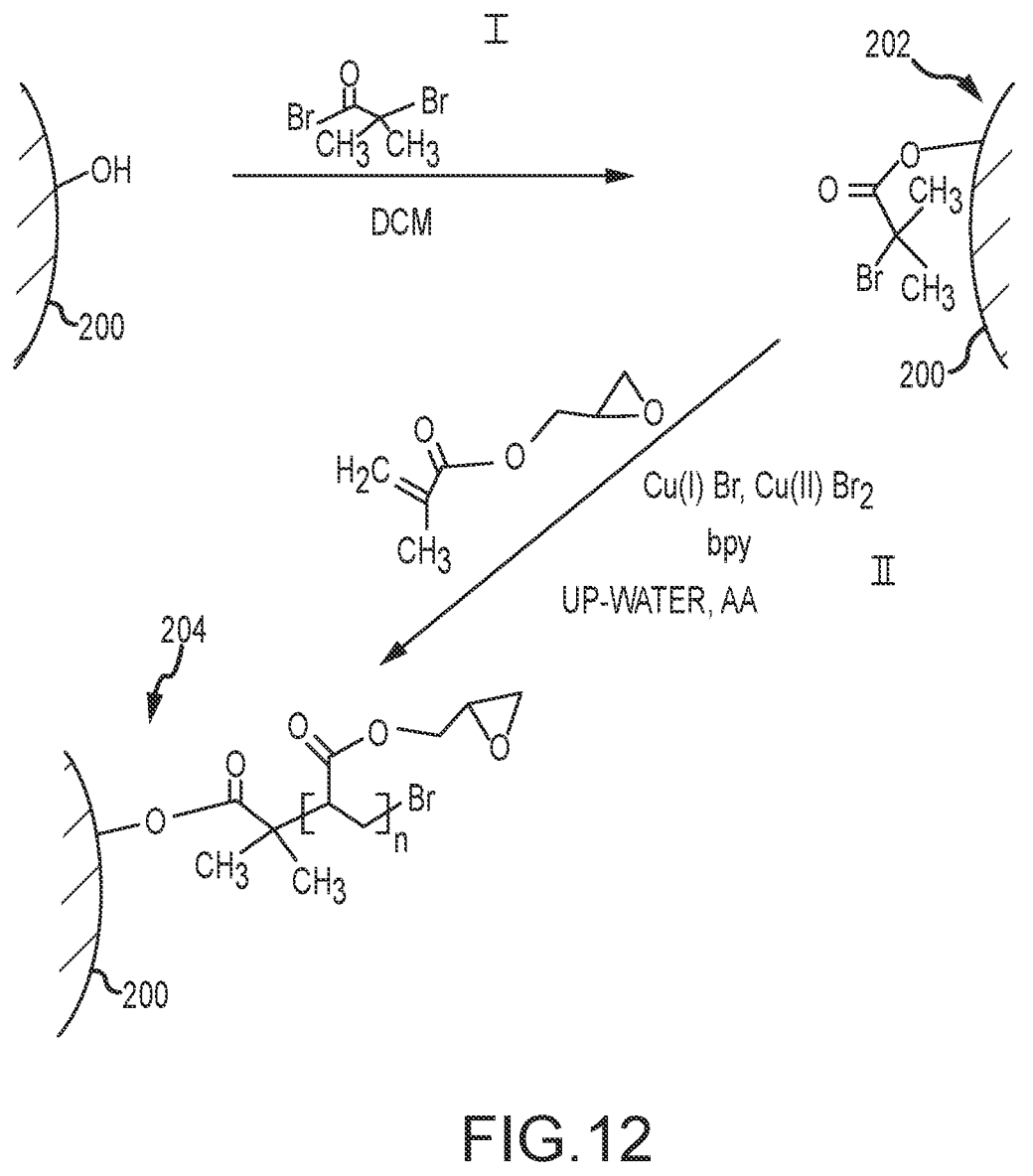

FIG. 12 shows a first step (I) of immobilizing an initiator group on the surface of a core particle 200 followed by a second step (II) of polymerization to prepare poly(glycidyl methacrylate). In step I, hydroxyl groups on the surface of the core particle 200 are reacted with α-bromoisobutyryl bromide to functionalize the surface of the core particle 200 with initiator groups to prepare modified particles 202 with the immobilized initiator groups, as shown in FIG. 12. In the example illustrated in FIG. 12, the reaction is performed with the core particles 200 suspended in an organic liquid medium and continuously stirred while the α-bromoisobutyryl bromide is added dropwise and the resulting suspension is stirred until the reaction is complete. In the example illustrated in FIG. 12, dichloromethane (DCM) is shown for the organic liquid medium, although any other suitable organic liquid medium could alternatively be used (e.g., tetrahydrofuran, acetonitrile, chloroform, acetone, carbon disulfide, carbon tetrachloride, dimethylformamide, or combinations of multiple organic liquid components). The organic liquid medium may be prepared from a mixture of organic solvent components, such as any of those identified in the preceding sentence. As shown in FIG. 12, the core particle 200 has been pre-prepared with surface hydroxyl groups. The core particle 200 may, for example, be made of any of the materials disclosed herein for a core of a sample monitoring bead with a core-shell structure, for example the core 106 illustrated in and described in relation to any of FIGS. 3-5 or as listed in the exemplary implementation combinations or claims provided below. A variety of small particles of varying size are commercially available pre-functionalized with hydroxyl groups to a desired extent. Alternatively, the particles of the core may be treated as part of the process to provide hydroxyl groups.

Following completion of the reaction of step I, the modified particles 202 with immobilized initiator groups are washed to remove reaction residue. For example, the modified particles 202 may be washed with a sequence of isopropanol, DCM, isopropanol and water. The modified particles 202 may be stored in water prior to processing in step II.

In step II shown in FIG. 12, glycidyl methacrylate monomer is polymerized to prepare poly(glycidyl methacrylate) covalently attached to the core particles 200 through the initiator groups immobilized on the surface of the modified particles 202. To a suspension of the modified particles 202 in ultrapure water (UP-water) are added copper (I) bromide, as a catalyst, 2,2'-bipyridine (bpy), as a chelating ligand to help solubilize the copper, ascorbic acid (AA) and glycidyl methacrylate, as monomer. The suspension is stirred until the polymerization reaction is completed, and the resulting modified beads 204 with poly(glycidyl methacrylate) covalently attached to the core 200 are washed to remove reaction residue. For example, the beads may be washed with a sequence of isopropanol, DCM, isopropanol and water.

Figure 13:
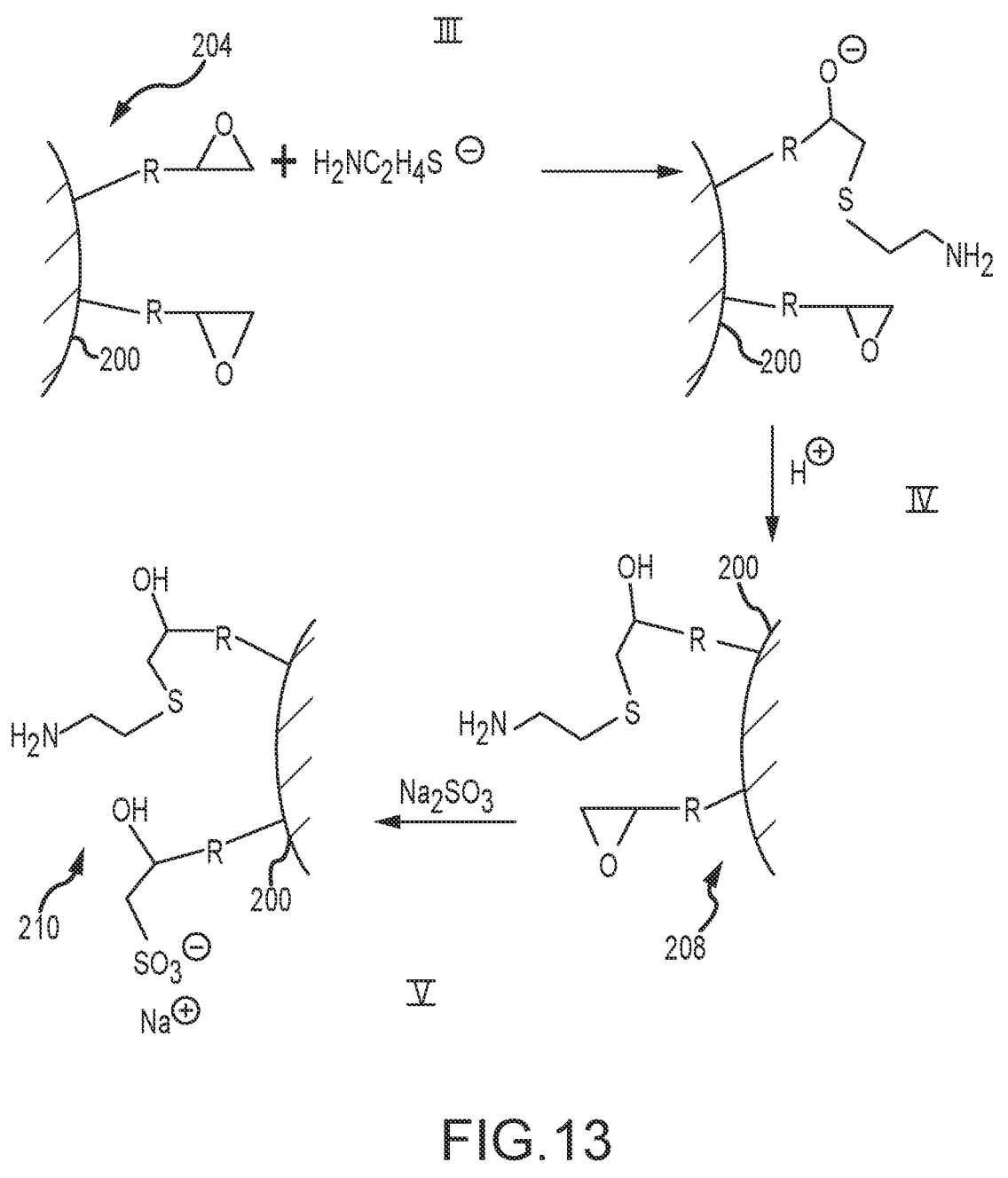

Reference is now made to FIG. 13 illustrating steps III-V of the example. In step III, the modified beads 204 resulting from step II are suspended in water and a defined amount of cysteamine is added to the suspension to provide a desired degree of conversion of epoxide functionality on the poly (glycidyl methacrylate) to amine functionality. The reaction mixture is maintained at a pH of from pH 7.5 to pH 8 to ensure a coupling reaction of thio-functionality provided by the cysteamine ($NH_2C_2H_4SH$) with epoxide groups. In solution, some of the cysteamine dissociates into a thiolate anion form ($NH_2C_2H_4S^-$), as shown in step III of FIG. 13, which reacts epoxide groups through nucleophilic attack on the least hindered carbon atom to form modified beads 206 including anionic groups with amine functionality, as illustrated in FIG. 13. In step IV illustrated in FIG. 13, the thio-containing anionic groups react with available protons in the reaction mixture to form the modified beads 208 with neutral groups containing the amine functionality. The resulting modified beads 208 are then washed with a sequence of isopropanol and water. For brevity in the illustration of FIG. 13, the epoxide functionality is shown connected to the core particle 200 through a general intermediate group (R) representing a portion of the hydrogel from which the epoxide functionality is pendent.

In step V illustrated in FIG. 13, the modified beads 208 are suspended in an aqueous solution containing sodium sulfite at about pH 8 and heated to about 85° C., to convert remaining epoxide groups to negatively charged sulfonate functionalities in the resulting modified beads 210, as shown in FIG. 13.

Figure 14:
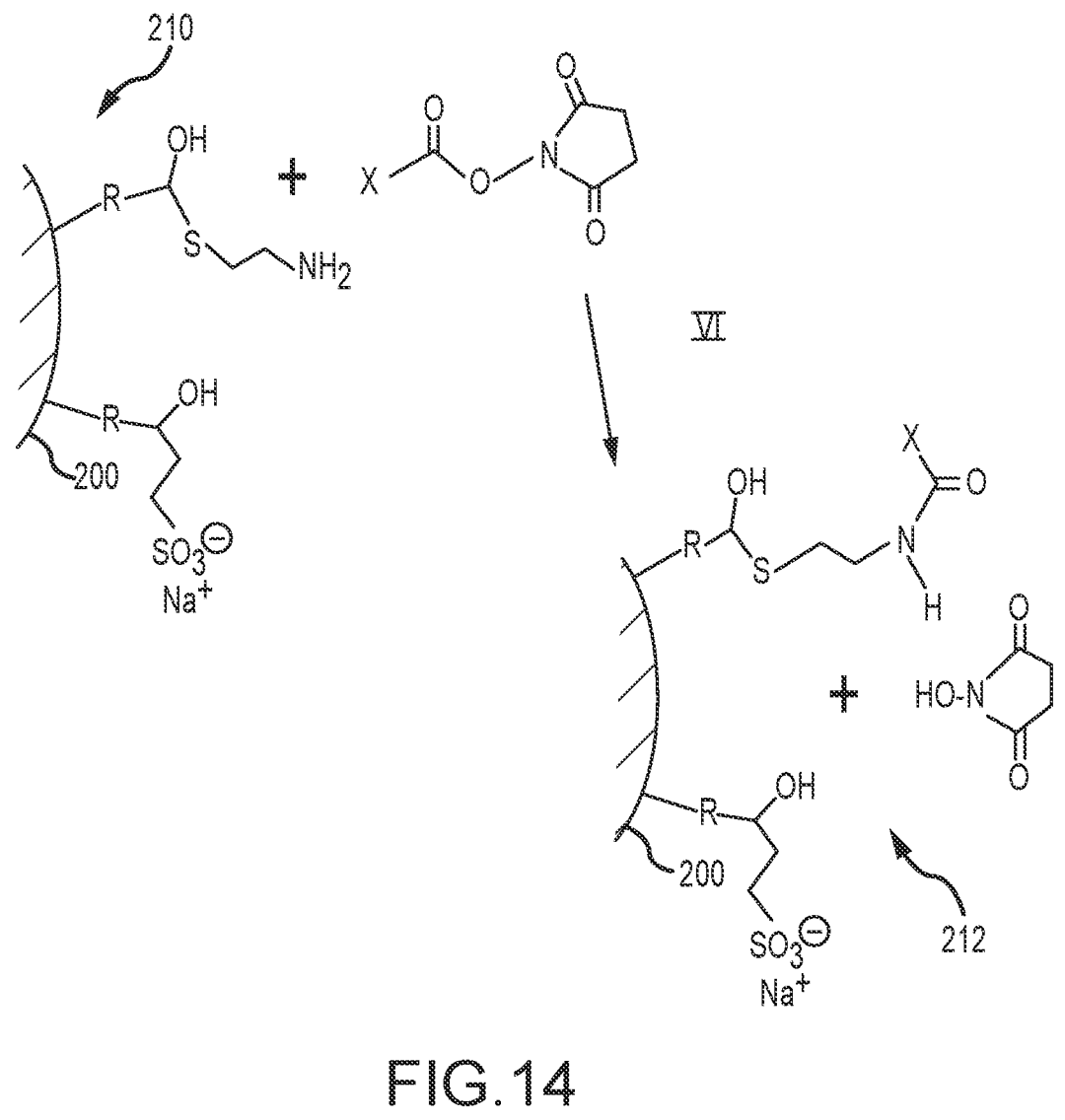

Reference is now made to FIG. 14, which shows step VI of the example, to fluorescently label the hydrogel of the modified beads 208 with fluorochrome groups, through reaction of the amine functionality of the modified particles 210 with a N-hydroxysuccinimide (NHS) ester having a desired fluorochrome group. In FIG. 14, a fluorochrome group is identified as "X". In step VI, the modified beads 210 are suspended in aqueous NaCl solution containing the NHS ester with the fluorochrome group (X) at a defined concentration for reaction with a desired number of the available amine groups, to provide a desired density of fluorochrome groups on the resulting sample monitoring beads 212. The reaction mixture is stirred until the coupling reaction to attach the fluorochrome group is complete, to prepare the desired sample monitoring beads with a size-sensitive, fluorescent hydrogel shell layer about the core particles 200.

The example of preparing sample monitoring beads illustrated in FIGS. 12-14 include a hydrogel as a shell layer attached to a core, and without cross-linking of hydrogel polymer chains other than through common attachment to the core. Cross-linking may be introduced into hydrogel by performing the initial polymerization in step I by including in the polymerization reaction mixture a multi-functional monomer to provide cross-links. Such multi-functional monomer may include multiple vinyl functionalities (multiple ethylenically unsaturated groups). A number of such multi-functional monomer cross-linking agents are commercially available. One example is N,N'-ethylenebis(acrylamide). Cross-linking may also be introduced following the polymerization of step I through allocation of some portion of the amine and/or epoxide functional groups of the modified particles 208 for cross-linking reactions.

The basic process illustrated in FIGS. 12-14 may be modified using similar reaction conditions adapted as appropriate to prepare a hydrogel with a structural polymer using monomers other than, or co-monomers in addition to, glycidyl methacrylate, with or without a multi-functional co-monomer to provide cross-linking. For example, there are a large number of available acrylic, methacrylic and other monomers with a vinyl group that could be used other than or in addition to glycidyl methacrylate, including any of the specific monomers listed above. As used herein, a vinyl group refers to any ethylenically unsaturated group, and includes for example acryloyl and methacryloyl groups. Moreover, as will be appreciated, post-polymerization modification may include modifications to incorporate functional groups into the hydrogel other than those shown in the example processing of FIGS. 12-14.

In one example, cationic functionality may be introduced into the hydrogel during initial polymerization by including an acrylic monomer with a quaternized nitrogen (e.g., ammonium or substituted ammonium functionality). One example of such a group containing quaternized nitrogen is a triethylammonium group, for example, as may be provided by inclusion of [2-(Methacryloyloxy)ethyl]trimethylammonium as a monomer, often in the form of a chloride salt. In one specific example [2-(Methacryloyloxy)ethyl]trimethylammonium and glycidyl methacrylate may be co-polymerized to provide hydrogel including cationic functionality from repeating units provided by the [2-(Methacryloyloxy) ethyl]trimethylammonium monomer and epoxide functionality provided by the glycidyl methacrylate monomer, and which epoxide functionality may be reacted to form amine functionality, in a manner as similar to that discussed above, which amine functionality may further reacted to fluorescently label the hydrogel with a fluorochrome group, for example through NHS ester labeling chemistry similar to that discussed above.

Monomers may also be included to provide zwitterionic functionality, with one example being through inclusion of [2-(Methacryloyloxy)ethyl]dimethyl-(3-sulfopropyl)ammonium hydroxide as a monomer, which includes a positively charged group with a quaternized nitrogen and negatively charged sulfonate group. In one specific example [2-(Methacryloyloxy)ethyl]dimethyl-(3-sulfopropyl)ammonium hydroxide and glycidyl methacrylate may be co-polymerized to provide hydrogel including zwitterionic functionality from repeating units provided by the [2-(Methacryloyloxy) ethyl]dimethyl-(3-sulfopropyl)ammonium hydroxide monomer and epoxide functionality provided by the glycidyl methacrylate monomer, and which epoxide functionality may be reacted to form amine functionality, in a manner as similar to that discussed above, which amine functionality may further reacted to fluorescently label the hydrogel with a fluorochrome group, for example through NHS ester labeling chemistry similar to that discussed above.

The hydrogel may be labeled with multiple different fluorochromes through procedures similar to those described above, for example, by reacting only a portion of available epoxide groups with a first NHS ester having a first fluorochrome group and reacting a remaining portion of the epoxide groups with a second NHS ester having a second fluorochrome group. Alternatively, multiple different NHS esters of different fluorochrome groups may be simultaneously reacted with available epoxide groups. Multiple different fluorochrome groups in the hydrogel may, for example, provide FRET functionality to the hydrogel. Multiple different fluorochrome groups in the hydrogel may, for example, provide multiple different fluorescent emission signatures for possible detection during a flow cytometry evaluation.

The same approaches may also be used to prepare sample monitoring beads that consist essentially of only hydrogel with desired functionality, and no core. For example, ATRP techniques similar to those described above may be used to polymerize acrylic monomers to prepare hydrogel particles of a desired size, which may be further modified post-polymerization as desired and to fluorescently label the hydrogels with one or more fluorochrome groups. Such hydrogel preparation will typically include a cross-linking agent is a co-monomer, for example, with multiple vinyl functionalities, similar to the discussion above.

Although preparation techniques have been exemplified by preparation of hydrogel through the use of ATRP techniques and primarily through the use of acrylic monomers, the sample monitoring beads of the present disclosure are not so limited. The hydrogel may be of any hydrogel composition functionalized with one or more fluorochrome groups and functionalized as desired to provide the desired level of size-responsiveness to changes in aqueous liquid medium of a flow cytometry fluid sample. Some example monomers that may be used to make hydrogels for the sample monitoring beads are disclosed, for example, the discussion above and in the following exemplary implementation combinations and/or the appended claims.

Figure 15:
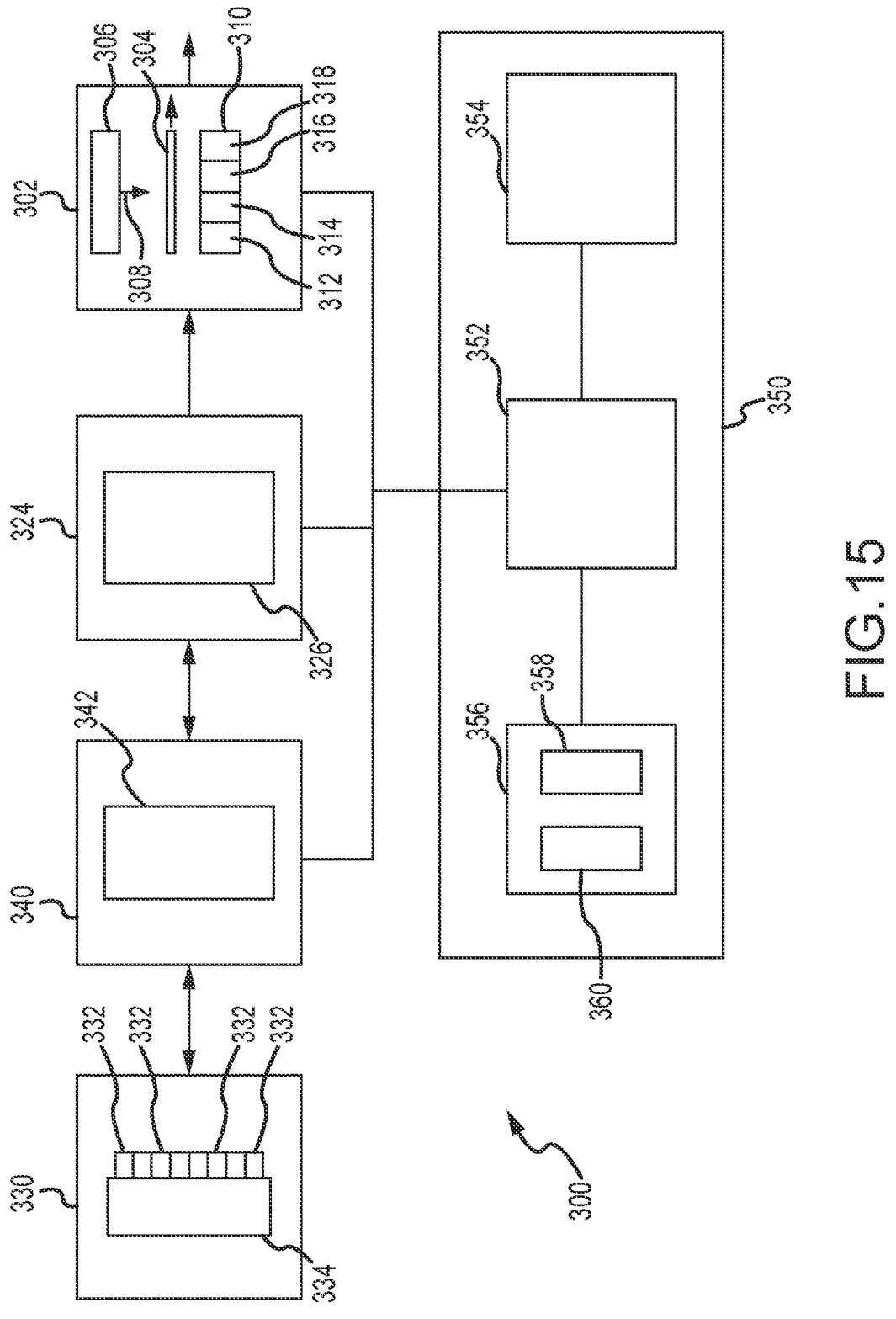
FIG. 15 is an illustration of an example flow cytometry system for use with sample monitoring beads to monitor fluid sample integrity during a high throughput, automated flow cytometry evaluation.

Reference is now made to FIG. 15, which illustrates an example of a high throughput, automated flow cytometry system 300 for use with the sample monitoring beads to evaluate fluid sample integrity during flow cytometry evaluation. The flow cytometry system 300 illustrated in FIG. 15 includes a flow cytometry investigation system 302 where fluid samples are subjected to investigations as part of a flow cytometry evaluation. The flow cytometry investigation system 302 includes an investigation zone 304 that provides a controlled flow conduction path for flow of fluid samples for investigation, a radiation delivery system 306 to provide stimulation radiation 308 to the investigation zone 304 for investigation of the fluid sample, and a radiation detection system 310 to detect response radiation from fluid samples passing through the investigation zone 304 that are subjected to the stimulation radiation 308 as part of a flow cytometry evaluation. The radiation delivery system 306 may include one or multiple radiation sources to provide one or multiple different beams of radiation to the investigation zone. Such different beams of radiation may have different properties (e.g., different wavelength bands of light) to investigate for different properties of particles in fluid samples flowing through the investigation zone 304. For example, the radiation delivery system 306 may include one or more lasers and/or other light sources such as LEDs, providing light about one or more particular wavelengths to stimulate one or more response radiations to be detected by the radiation detection system 310. When the radiation delivery system contains multiple different radiation sources, such radiation sources may be spaced along the investigation zone 304 and sufficiently shielded from one another to minimize interference between different radiation sources. The investigation zone 304 may be configured to receive a flow of fluid sample by itself or may be configured to receive a hydrodynamically focused flow of fluid sample encased by a sheath fluid. The investigation zone 304 may comprise a flow cell of a flow cytometer. The investigation zone 304 may be a continuous length of transparent conduit or may comprise discontinuous transparent portions of a longer conduit system. The radiation detection system 310 may include one or more different radiation detectors to detect different response radiation properties coming from the investigation zone. Such radiation detectors may, for example, be selected from a group of photo detection devices including photomultiplier tubes, silica photomultipliers, avalanche photodiodes and selection photodiodes, with photomultiplier tubes often being preferred when there is a desire to detect and process very weak signals. When multiple radiation detectors are included, the radiation detectors may detect for signals in different wavelength ranges or may be positioned to receive signals from different directions. The response radiation detected by the radiation detection system 310 will include a fluorescent signal from the fluorescent hydrogel of the sample monitoring beads and may also include one or more other fluorescent signals from fluorescent labels that may be used to stain fluid samples to fluorescently label target particles of interest and/or may also include light scatter, for example forward scatter light and/or side scatter light. In the example illustrated in FIG. 15, the radiation detection system 310 is shown including four radiation detectors, including a first detector 312 to detect for fluorescence from the fluorescent hydrogel of the sample monitoring beads, a second detector 314 to detect for fluorescence from a fluorescent label used to stain target particles of interest, a third detector 316 to detect for forward scatter light, and a fourth detector 318 to detect for side light scatter. As will be appreciated, the radiation detection system 310 may include fewer than or more than the four radiation detectors as illustrated in the example of FIG. 15, although the radiation detector would include at least a detector for detection of the fluorescent emission of the fluorescent hydrogel of the sample monitoring beads. The different radiation detectors may be appropriately oriented and spaced along the investigation zone 304 for effective detection of the desired response radiation.

The flow cytometry system 300 illustrated in FIG. 15 includes a sample delivery system 324 that interfaces with sample containers to withdraw fluid sample from sample containers and provide an evaluation volume of the fluid sample to the investigation zone 304 for investigation as part of a flow cytometry evaluation. Such a sample delivery system 324 may include a connector for manual connection of a sample container to a flow cytometer and a flow path within the flow cytometer to the investigation zone 304. The example sample delivery system 324 illustrated in FIG. 15, however, includes an autosampler 326 capable of processing a group of sample containers provided in a tray to sequentially withdraw the fluid samples from the different sample containers and provide the fluid samples to the flow cytometry investigation system 302 for evaluation in the desired sequence. The tray may be in the form of a multi-well plate with the fluid sample containers being wells of the plate. Such a multi-will plate may have any number of wells, and may be for example 96-well plate, a 384-well plate or a 1536-well plate. The tray may be in the form of a vial tray with a plurality of vials with fluid samples received in tray receptacles. Such a vial tray may include any number of vial receptacles and any number of vials received in the vial receptacles. The sample delivery system 324 includes a fluid path for transferring fluid sample from the autosampler 326 to the investigation zone 304. The autosampler 326 may be integral to a flow cytometer or may be a separate unit fluidly connected to a flow cytometer. As an example, the flow cytometry investigation system 302 and the sample delivery system 324 may be similar to the iQue® 3 flow cytometry system.

The flow cytometry system 300 illustrated in FIG. 15 includes a storage system 330 with multiple trays 332 stored in a storage structure 334. Each tray 332 includes a different group of sample containers with fluid samples for processing by the autosampler 326 for flow cytometry evaluation. The flow cytometry system 300 also includes a robotic transfer system 340 for automated robotic transfer of the trays 332 one at a time in a tray sequence to the autosampler 326 for processing by the autosampler 326. As shown in FIG. 15, the robotic transfer system 340 includes a robotic arm unit 342 with a robotic arm that is adjustable vertically, rotationally and radially to remove plates 332 one at a time from the storage structure 334 and transfer the plates in a sequence to the autosampler 326. As one example, the robotic arm unit 342 may be provided by the PlateCrane EX™ robotic arm microplate handler from Hudson Robotics, for which Hudson has developed a plugin for its SoftLinx™ laboratory automation scheduling software for the iQue® 3 flow cytometry system. As may be appreciated, the time duration for the flow cytometry system 300 to process all of the fluid sample in all of the trays 332 may last for several hours or even days, with the system operating automatically until all fluid samples have been evaluated by flow cytometry. The sample monitoring beads in the fluid samples provide a convenient technique for monitoring the integrity of the fluid samples over this long time duration and to identify detrimental chemical changes to fluid samples as the fluid samples are stored for long periods of time prior to being processed during a high throughput, automated flow cytometry evaluation.

The flow cytometry system 300 illustrated in FIG. 15 also includes a data evaluation and control system 350. The data evaluation and control system 350 includes a computer processor 352 and a computer memory 354, preferably non-volatile computer memory (e.g., disc drive, solid state drive, flash drive), with stored instructions executable by the computer processor 352 for operation the flow cytometry system 300 to perform flow cytometry evaluations. The stored instructions include instructions executable by the computer processor 352 to evaluate detected radiation information from the radiation detection system 310 and to evaluate and integrity of the fluid sample, including evaluating the detected response radiation from the sample monitoring beads in fluid samples investigated in the investigation zone 304. For example, when the flow cytometry system 300 includes the iQue® 3 flow cytometry system and the PlateCrane EX™ robotic arm microplate handler, the data evaluation and control system 350 may have stored in the computer memory 354, and executable by the computer processor 352, control and data evaluation software for the iQue® 3 flow cytometry system and the SoftLinx™ laboratory automation scheduling software with the plugin for the iQue® 3 flow cytometry system. The passage of a sample monitoring bead through the investigation zone 304 may be identified through detection by the detector 312 of a fluorescent emission from the fluorescent hydrogel of the sample monitoring beads and evaluation of the detected fluorescent emission by the data evaluation and control system 350. Identification of sample monitoring beads may also include correlation of detection of the fluorescent emission from the fluorescent hydrogel with identification of a particle through evaluation of light scatter detection from one of both of the detector 316 and detector 318. In such an implementation, identification of a particle though light scatter detection may serve as a gating function for then identifying sample monitoring beads from detected fluorescent emission from the fluorescent hydrogel. Alternatively, identification of sample monitoring beads may be based solely on detection of the fluorescent emission from the fluorescent hydrogel, and without a gating function provided by light scatter detection of a particle. As will be appreciated, the intensity of the fluorescent signal received by the detector 312 will vary depending on how expanded or contracted is the size of the sample monitoring bead, as a function of expansion and contraction of the fluorescent hydrogel. Based on the level of the intensity of the detected fluorescent signal from the sample monitoring beads, the properties of the liquid medium of the sample fluid may be evaluated and issues regarding sample integrity may accordingly be determined. For example, a detected fluorescence intensity indicating an undesirably low pH and/or an undesirably high salt concentration or osmolarity may indicate a fluid sample that lacks sufficient integrity to be relied upon as providing accurate flow cytometry results for target particles in the fluid sample. The detected fluorescence intensity may be compared to a reference intensity criterion (e.g., a standard reference intensity regardless of the fluid sample or a predetermined expected intensity for the particular fluid sample). The degree of departure of the detected fluorescence intensity relative to a reference intensity provides an indication of a degree of deviation of fluid sample properties from optimal or expected properties for the fluid sample, and an estimation of the properties of the fluid sample liquid medium (e.g., pH, salt concentration, and/or osmolarity) may be made through comparison of the detected fluorescence intensity to such a reference intensity. The data evaluation and control system 350 also includes a user interface 356 in communication connection with the computer processor 352. The user interface 356 as illustrated in FIG. 15 includes a video display 358 to display to a user information about the flow cytometry system 300 and/or operation of the flow cytometry system 300, including to visually display results of or status of a flow cytometry evaluation. The user interface 356 also includes a data input system 360 manipulable by a user to input data and provide instructions to the data evaluation and control system 350 to be processed by the computer processor 352 and/or stored in the computer memory 354. The data input system 360 may include, for example, a keyboard and/or a touchscreen. As will be appreciated, a touchscreen input device may be combined in a single unit with the video display 358. The video display 358 and/or data input system 360 may be in a separate unit or units (e.g., a laptop, notebook, tablet, desktop computer or remote server system) or may be integrated with other components of the flow cytometry system 300, for example with the flow cytometry investigation system 302, the sample delivery system 324 and/or the robotic transfer system 340.

As shown in FIG. 15, the data evaluation and control system 350 is in communication connection with the flow cytometry investigation system 302, the sample delivery system 324 and the robotic transfer system 340. A communication connection between the data evaluation and control system 350 and other portions of the flow cytometry system 300 may be through wired connections, wireless connections or a combination of wired and wireless connections. Communication connections between the data evaluation and control system 350 and the other portions of the flow cytometry system 300 may be provided entirely or in part through a cloud-based (internet) connection.

In general, performance of a flow cytometry evaluation using the flow cytometry system 300 of FIG. 15 includes preparing the trays 332 with prepared fluid samples in fluid containers of the trays 332. Typically, at least one, and preferably multiple, and even more preferably, all of the fluid samples in a tray 332 contain the sample monitoring beads. For example, the sample monitoring beads may be in a single fluid sample of a tray 332, with or without biological material for evaluation of target particles, in which case the fluid sample with the sample monitoring beads may serve as a sentinel for assessment of possible changes in properties of the fluid samples of the tray 332 between the time of sample preparation and the time that the tray 332 is processed by the autosampler 326. A tray 332 could include multiple such sentinel fluid samples spaced as desired at different points in a flow cytometry sequence. In some preferred implementations, each fluid sample in a tray 332, and more preferably in all the trays 332, includes the sample monitoring beads, so that each fluid sample may be independently assessed for sample integrity by the data evaluation and control system 350. After the trays 332 are prepared with fluid samples and loaded into the storage structure 334 of the storage system 330, then a user may direct the data evaluation and control system 350 to perform a flow cytometry evaluation. The data evaluation and control system 350 then directs control of the robotic transfer system 340, sample delivery system 324 and flow cytometry investigation system 302 to perform the flow cytometry evaluation. During the flow cytometry evaluation, the trays 332 are removed from the storage structure 334 one at a time by the robotic arm unit 342 and transferred to the autosampler 326 for processing by the autosampler 326 to remove fluid samples from the different sample containers of the tray 332 for delivery to the investigation zone 304 to be subjected to the stimulation radiation 308, with response radiation being detected by the detectors of the radiation detection system 310. After completion of processing of all fluid samples of a tray 332 by the autosampler 326, the robotic arm unit 342 may return the processed tray 332 to the storage unit 334 (or to another location) and may remove from the storage unit 334 the next tray 332 in a sequence and deliver that next tray 332 to the autosampler 326 for processing. The sequence may be continued until all desired trays 332 have been processed. The data evaluation and control system 350 receives detected response radiation information from the radiation detection system 310 for processing by the computer processor 352 and for storage with flow cytometry results for the different fluid samples in the computer memory 354. Progress of a flow cytometry evaluation may be displayed to a user in real time or near real-time on the video display 358. In one implementation, when the data evaluation and control system 350 determines that a fluid sample has an integrity issue based on evaluation of detected response radiation from the sample monitoring beads, the computer processor 352 may direct generation of an integrity warning notification to alert the user of a possible problem with fluid sample integrity. Such a sample integrity warning may be saved with flow cytometry data recorded in the computer memory 354 and/or may be indicated to a user in real-time or near real-time through the user interface 356, for example, by displaying the integrity warning notification on the video display 358 and/or providing an audible warning signal to the user. The content of the integrity warning may vary depending on the identified severity of a deficiency in fluid sample integrity for one or more monitored fluid samples.

In some implementations, the data evaluation and control system 350 may determine that monitored fluid sample integrity is deficient to such a high degree that one or more fluid samples should be removed from a planned sequence of flow cytometry evaluation in the processing of the fluid samples originally loaded into the storage system 330 and/or being processed by the autosampler 326. For example, the data evaluation and control system 350 may determine that a set of fluid samples contained in one or more of the trays 332 is so deficient in sample integrity that the computer processor 352 instructs the autosampler 326 to discontinue processing one or more of the remaining fluid samples in a tray 332 being processed by the autosampler. As another example, if the data evaluation and control system 350 determines that multiple samples across multiple trays 332 have exhibited a high degree of deficiency in sample integrity, the data evaluation and control system 350 may instruct a complete discontinuance of processing of any further fluid samples in the planned sequence for all of the trays 332.

Figure 16:
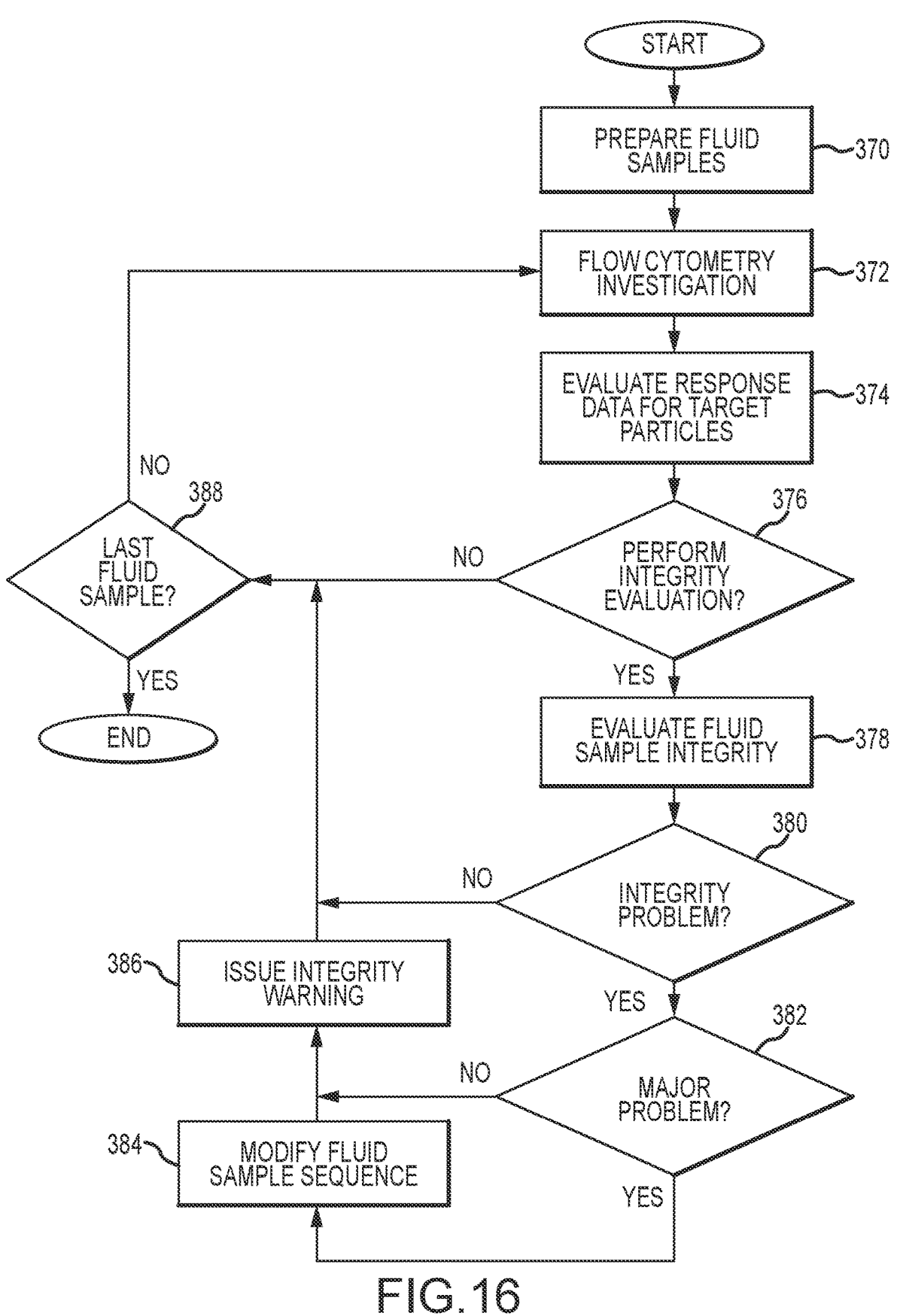
FIG. 16 is an illustration of an example method of flow cytometry evaluation and error handling using sample monitoring beads to monitor fluid sample integrity during a high throughput, automated flow cytometry evaluation.

FIG. 16 includes a process flow diagram illustrating processing of an example method of flow cytometry evaluation of a plurality of fluid samples for target particles of interest and using the sample monitoring beads for evaluation of fluid sample integrity. The method illustrated in FIG. 16 may, for example, be performed using the high throughput, automated flow cytometry system 300 of FIG. 15.

The illustrated method of FIG. 16 starts with preparation of fluid samples 370 to be subjected in a sequence to flow cytometry for evaluation for the presence of the target particles. One or more, or all, of the fluid samples may be prepared to include the sample monitoring beads. Such prepared fluid samples may, for example, be disposed in sample containers of trays 332 and loaded into the storage structure 334 of FIG. 15. The prepared fluid samples are then subjected one at a time in a sequence to an operation 372 of flow cytometry investigation, which may include subjecting a flow of the fluid sample in an investigation zone to stimulation radiation and detecting for response radiation from the investigation zone. When using the flow cytometry system 300 of FIG. 15, at the direction of the data evaluation and control system 350, trays 332 of fluid samples may be transferred in a sequence from the storage structure 334 by the robotic arm unit 342 to the autosampler 326, which then sequentially withdraws and delivers an evaluation volume of each fluid sample to the flow cytometry investigation system 302 for investigation in the investigation zone 304. In the processing of FIG. 16, after the flow cytometry investigation 372 of a fluid sample, there is operation 374 to evaluate the response data for the presence of a target particle, which may be performed, for example, by the data evaluation and control system 350 of FIG. 15, optionally with flow cytometry results being stored in the computer memory 354 and/or with real-time or near real-time results and status information being displayed on the video display 358.

Next, the method of FIG. 16 includes a decision 376 of whether or not to perform an operation 378 to evaluate fluid sample integrity. The evaluation of fluid sample integrity or operation 378 may be performed periodically on selected fluid samples, for example, at the direction of and by the data evaluation and control system 350 of FIG. 15. When processing a sequence of trays of fluid samples (e.g., trays 332 of FIG. 15), it is preferred that at least one fluid sample in each processed tray include sample monitoring beads and be subjected to the operation 378. More preferably a plurality of fluid samples in each processed tray, and most preferably all fluid samples processed, include sample monitoring beads and are subjected to the evaluation of the operation 378. During an evaluation of fluid sample integrity of operation 378, a detected response radiation from the sample monitoring beads is evaluated relative to reference criteria to determine whether, and optionally also to what degree, there is a deficiency in fluid sample integrity, which could call into question the validity of flow cytometry results for that fluid sample. The results for each fluid sample subjected to the operation 378 are subjected to a selection 380 to determine whether the fluid sample has an integrity problem. If the determination of the selection 380 is "yes", then processing proceeds to another selection 382 to determine whether the sample integrity problem is or is not a major problem. If the determination of the selection 382 is "yes", that the sample integrity problem is a major problem, then the processing proceeds to an operation 384 to modify the fluid sample sequence, where one or more of the remaining fluid samples are removed from the flow cytometry sequence. The determination as to whether there is a major problem may include evaluation of the sample integrity of the current fluid sample in combination with fluid sample integrity evaluations performed on prior fluid samples, indicating, for example, a continuing degradation over time of the integrity of a number of fluid samples. For example, remaining fluid samples in a tray (e.g., a tray 332 of FIG. 15) may be removed from the sequence. For a particularly severe integrity problem over a number of fluid samples, the sequence may be discontinued entirely at that point, in which case the current fluid sample could be the last fluid sample subjected to the flow cytometry evaluation of the terminated sequence. Also as shown in FIG. 16, when a problem is identified for a fluid sample, whether or not the integrity deficiency is determined to be a major problem, the processing includes issuing an integrity warning 386. Such an integrity warning 386 may be displayed on a video display (e.g., video display 358 of FIG. 15) and/or may be saved with flow results (e.g., in computer memory 354 of FIG. 15).

Regardless of determinations during the selection 376, selection 380 or selection 382, processing proceeds eventually to a selection 388 to determine whether the processed fluid sample was the last fluid sample to be processed. If the determination in selection 388 is "yes", either because the full sequence of fluid samples has been completed or because the sequence has been terminated as a consequence of the operation 384, then the processing ends. If the determination of selection 388 is no, then the processing continues to flow cytometry evaluation of the next fluid sample in the sequence, as the sequence may have been modified by the modification of the operation 384.

As will be appreciated, when the flow cytometry system 300 of FIG. 15 is used in connection with the method illustrated in FIG. 16, steps 374, 376, 378, 380, 382, 384, 386 and 388 may be performed by the data evaluation and control system 350 of FIG. 15, and operation of the sample delivery system 324, robotic transfer system 340 and flow cytometry investigation system 302 may be at the direction and control of the data evaluation and control system 350, for example, as directed by the computer processor 352 executing instructions stored in the computer memory 354 and/or executing instructions input by a user through the data input system 360.

Figure 17:
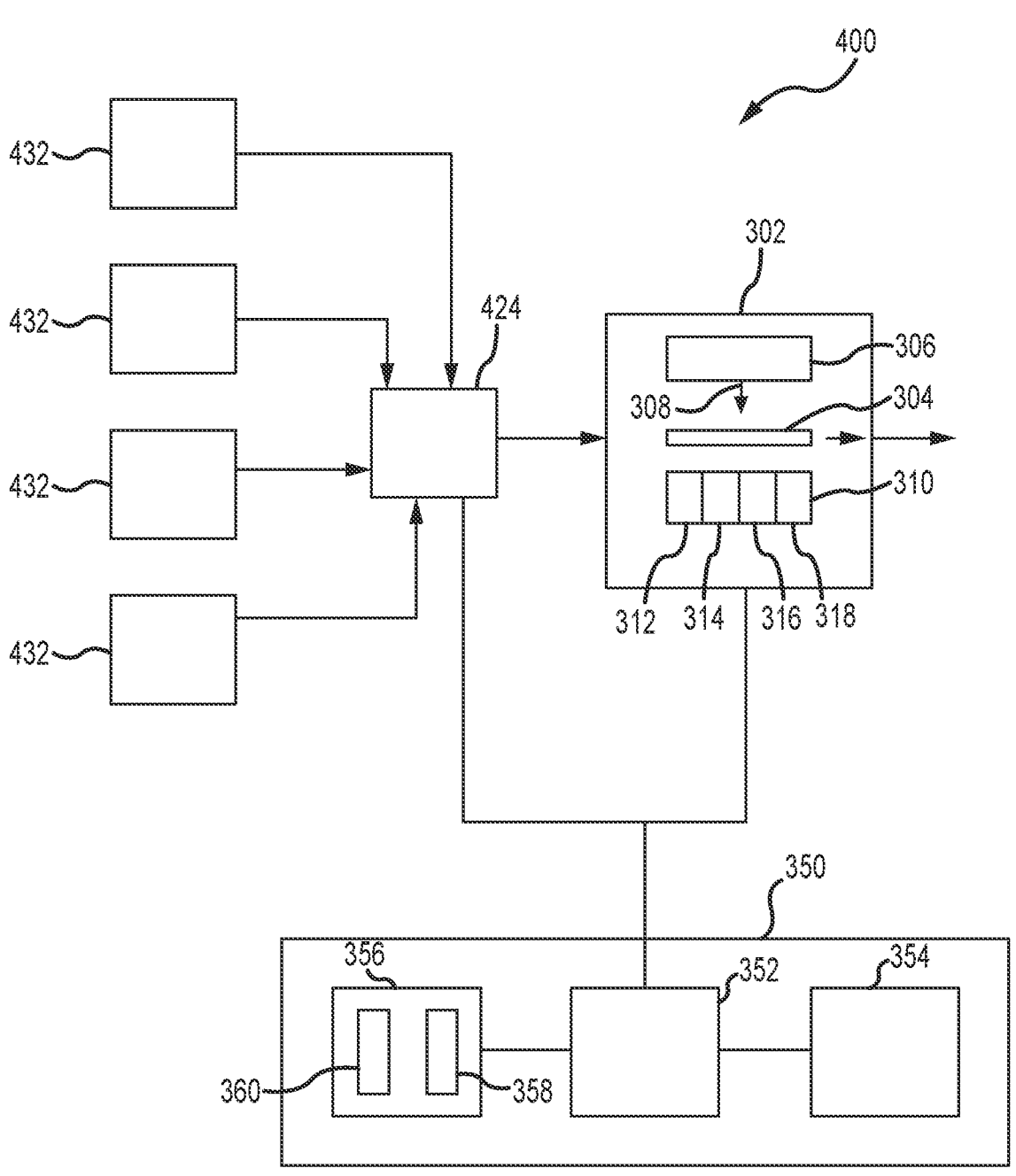
FIG. 17 is an illustration of another example flow cytometry system for use with the sample monitoring beads to monitor fluid sample integrity.

Reference is now made to FIG. 17, which illustrates an example flow cytometry evaluation system 400 configured to automatically periodically sample and subject to flow cytometry fluid samples of bioreactor media from a plurality of bioreactors 432. In the example of FIG. 17, the flow cytometry evaluation system 400 includes the same flow cytometry investigation system 302 and data evaluation and control system 350 as illustrated in and described in relation to FIG. 15. However, as shown in FIG. 17, the flow cytometry evaluation system 400 includes the bioreactors 432 with bioreactor media containing sample monitoring beads, and which bioreactor media are periodically sampled from each of the bioreactors in a sequence to periodically provide fluid samples of the bioreactor media for evaluation by the flow cytometry investigation system 302. The flow cytometry system 400 includes a sample delivery system 424 that interfaces with the bioreactors 432. As directed by the data evaluation and control system 350, the sample delivery system 424 automatically periodically withdraws a fluid sample of bioreactor medium from a bioreactor 432 and directs the fluid sample to the flow cytometry investigation system 302 for flow cytometry evaluation. The components and operation of the data evaluation and control system 350 are the same as described previously with reference to FIG. 15. In the implementation of FIG. 17, the computer memory 354 includes instructions accessible and executable by the computer processor 352 for operation the flow cytometry system 400 to direct operation of the sample delivery system and to perform flow cytometry evaluations in the flow cytometry investigation system 302. As with the discussion in relation to FIG. 15, the user interface 356 permits a user to input data and provide instructions to the data evaluation and control system 350 to be processed by the computer processor 352 and/or stored in the computer memory 354. The user interface 356 also permits a user to display and review results of or status of a flow cytometry evaluation. In one implementation example, the bioreactors 432 may be used for parallel testing of multiple different process conditions for bioreactor operation. For example, the bioreactors 432 may be part of a system such as an Ambr® system (Sartorius) for high throughput, automated testing of different process conditions for accelerated process development.

Although the sample monitoring structures, including in the form of the sample monitoring beads, are described herein primarily for use to monitor fluid samples during flow cytometry, uses of the sample monitoring structures, including the sample monitoring beads, are not so limited and may be used with other fluid samples in other analytical systems including radiation detection capability to detect fluorescent emissions from the sample monitoring structures, provided that the presence of the sample monitoring structure is not detrimental to operation of the analytical technique. One example of such other analytical system in which the sample monitoring beads, or other form of the sample monitoring structure, may be used are so-called live cell imaging and analysis systems, in which individual cells are imaged and analyzed, often directly in a cell culture, and typically over an extended period and with time-lapse imaging of cell culture development over time. Additionally, some systems are designed to accommodate and analyze a plurality of different cell cultures simultaneously operated in parallel and contained in a common incubator for an extended time, to compare performance of different cell culture conditions. Effective monitoring of culture media conditions in a plurality of culture containers over an extended period, and correlation with time-lapse images, are significant issues. The Incucyte® live cell imaging and analysis system is an example of such systems. Sample monitoring beads may be included in culture medium and analyzed in-place in the culture medium as the analyzed fluid sample to provide information on the properties of the culture medium, for example to monitor changes in the culture medium over time during a cell expansion operation or to identify development of undesirable culture medium properties which are not desired for optimum cell expansion. Another example of such other analytical systems in which the sample monitoring beads, or another form of the sample monitoring structure, may be used are systems in which trap and analyze single particles, such as so-called "optical tweezer" techniques (also sometimes called single-beam gradient force trap techniques) in which individual particles are trapped and held by optical forces for individual-particle analysis, for example by spectroscopic imaging (e.g., Raman spectroscopy) and may also be examined for fluorescent properties. Yet another example of such other analytical systems in which the sample monitoring beads may be used are systems that implement dynamic light scattering and related techniques that analyze properties associated with Brownian motion of particles. One such technique is nanoparticle tracking analysis and another such technique is fluorescence correlated spectroscopy. Yet another example of such other analytical systems in which the sample monitoring beads, or another form of the sample monitoring structure, may be used are parallel bioreactor systems, which include a plurality of bioreactors, typically of a small, laboratory scale in size, operated in parallel to simultaneously test a plurality of different bioreaction operating conditions for a biological production process, for example for cell culture or fermentation processing. Such systems may include from several to hundreds of bioreactors operated in parallel to simultaneously test a variety of processing conditions. Effective monitoring of conditions inside of the different bioreactors, including conditions of the growth medium in each bioreactor, is a significant issue. Some example parallel bioreactor systems are the Ambr® parallel bioreactor systems (Sartorius). Any of these other example analytical systems may include the sample monitoring beads in the respective fluid samples, and which may be subjected to stimulation radiation to test for a fluorescent emission response from the sample monitoring beads. In any of these other example analytical techniques, the sample monitoring beads may be included in a fluid sample and subjected to analysis of fluorescence emission response to applied radiation stimulus to monitor properties of the fluid sample and identify issues with fluid sample integrity. Similarly, in such other analytical systems it is not required that the sample monitoring structure be in a particulate form, the sample monitoring structure can be in a different form (e.g., monolithic structure or surface layer on an immobilized substrate) to contact the aqueous liquid medium to be monitored. However, as noted above, use of the sample monitoring structure in the form of the sample monitoring beads may still be preferred to benefit from the intimate contact between liquid medium when the beads are dispersed in the liquid medium and to benefit from a fast hydrogel response as a consequence of high surface area in the bead form.

Figure 18:
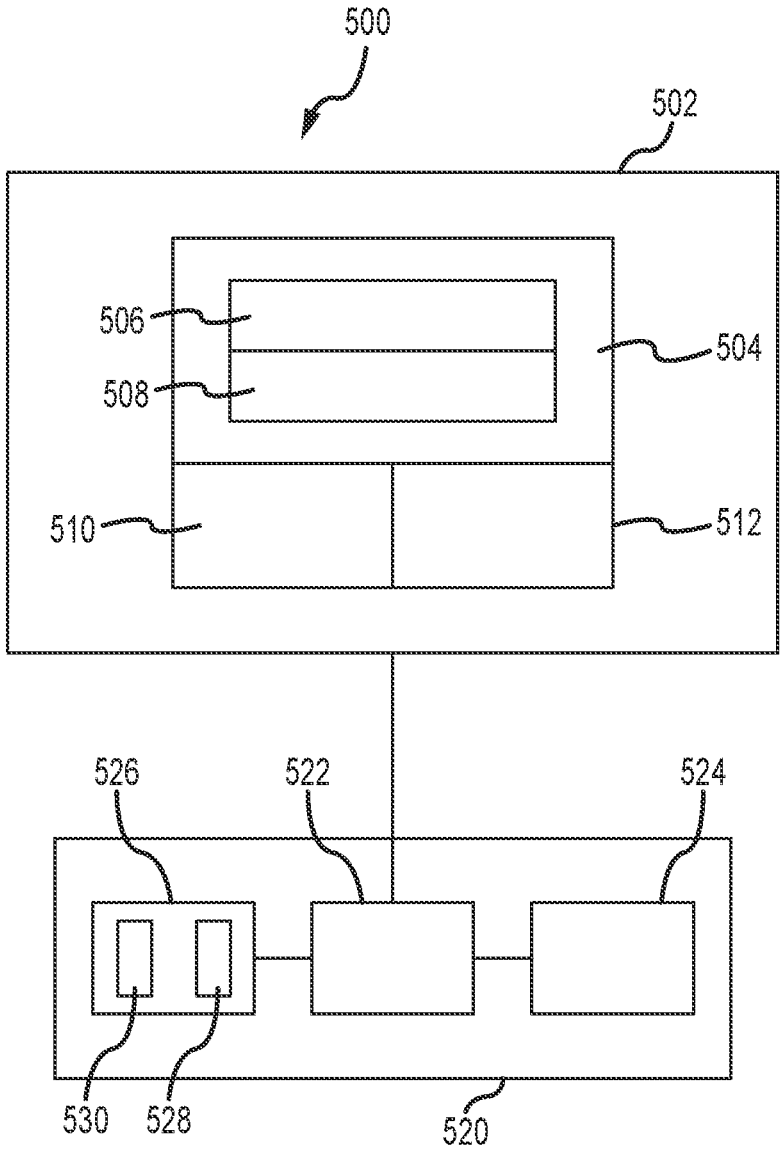
FIG. 18 is an illustration of a general example of an analytical evaluation system including the sample monitoring structure.

Reference is now made to FIG. 18, including an illustration of an exemplary embodiment of an analytical system 500 with general elements illustrated in block form. As shown in FIG. 18, the analytical system 500 includes an analytical investigation system 502. The analytical investigation system 502 includes an investigation zone 504 in which is disposed an aqueous liquid medium 506 for analytical investigation and a sample monitoring structure 508 in contact with the aqueous liquid medium 506. The sample monitoring structure 508 may be in the form of the sample monitoring beads, which may or may not be dispersed in the aqueous liquid medium 506, and alternatively the sample monitoring structure 508 may be in a different form. The sample monitoring structure 508 includes a fluorescently-labeled hydrogel to monitor one or more properties of the aqueous liquid medium 506 in the investigation zone 504.

The investigation system 502 further includes a radiation delivery system 510 to provide stimulation radiation to the investigation zone 504 to generate a fluorescent emission response from the sample monitoring structure 508. The investigation system 502 also includes a radiation detection system 512 with detection capability to detect at least the fluorescent emission from the sample monitoring structure 508. The analytical system 500 also includes a data evaluation and control system 520 in communication connection with the investigation system 502 to receive information from the investigation system 502 and to provide operational control instructions to the investigation system 502. The data evaluation and control system 520 includes a computer processor 522, a computer memory 524 (preferably non-transitory memory) and a user interface 526. The computer memory 524 has stored therein instructions executable by the computer processor 522 to evaluate detected radiation information from the radiation detection system 512 and to evaluate properties of the aqueous liquid medium 506 in the investigation zone 504, optionally including evaluation of the integrity of the aqueous liquid medium relative to reference criteria. The user interface 526 includes a data input system 530 and a video display 528. The data evaluation and control system 520 and components thereof may be similar to and operate in a manner as described with respect to the data evaluation and control system 350 illustrated in and described in relation to FIG. 15, with the data evaluation and control system configured to operate with the investigation system 502 through appropriately programmed computer instructions stored in the computer memory 524. As will be appreciated, the radiation delivery system 510 may be configured with a single radiation source (e.g., a single laser) or with multiple different radiation sources (e.g., multiple different lasers or a phase contrast lamp in addition to one or more lasers). Likewise, the radiation detection system 512 may be configured to detect for radiation signals other than the fluorescent emission from the sample monitoring structure 508. For example, the radiation detection system 512 may detect other fluorescent emission signatures besides the fluorescent emission of the sample monitoring structure, may detect for light scatter, or may detect for phase contrast.

Figure 19:
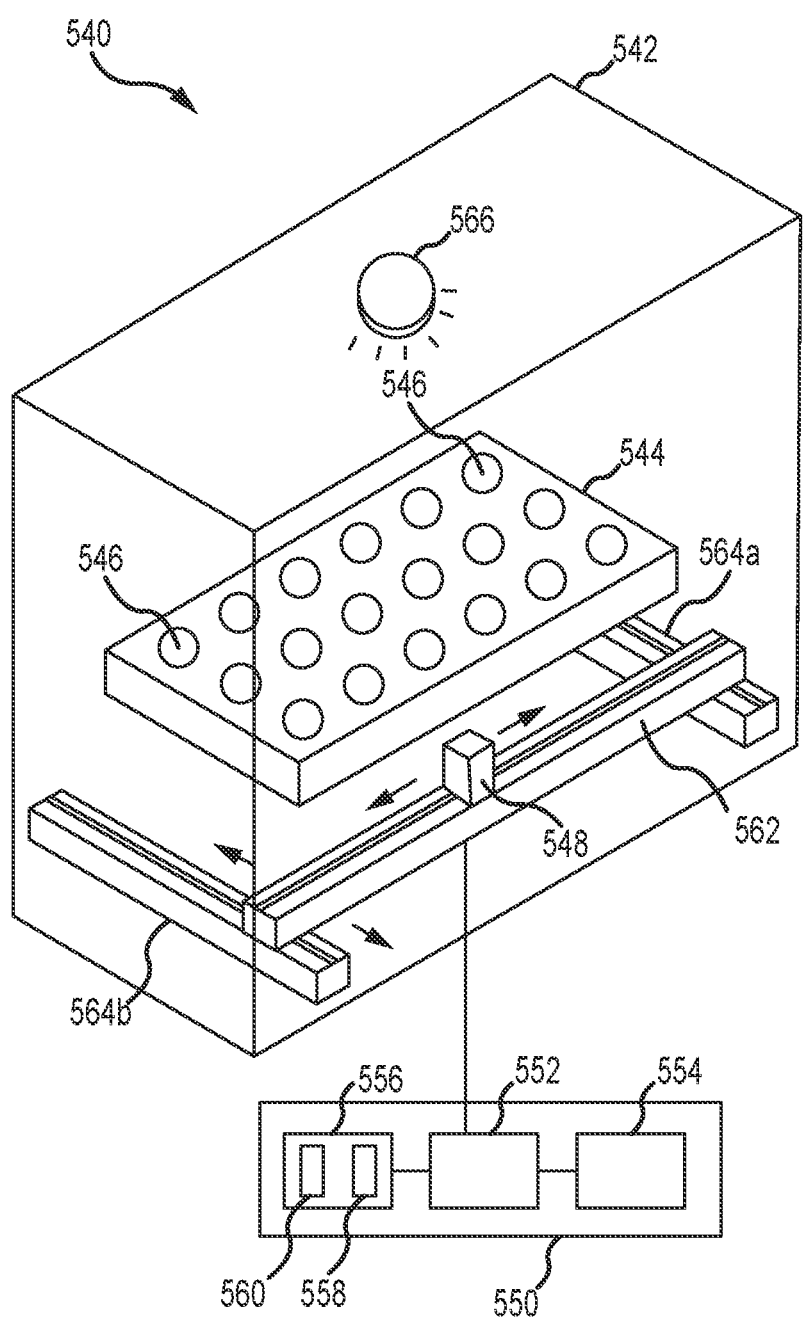
FIG. 19 is an illustration of an example of a live cell imaging and analysis system for use with the sample monitoring structure.

Reference is now made to FIG. 19, illustrating features of an analytical system in the form of an example live cell imaging and analysis system 540. As shown in FIG. 19, the live cell imaging and analysis system 540 includes an environmentally-controlled incubator 542 (e.g., with temperature, humidity and/or atmospheric composition control) in which is disposed a plate 544 including a plurality of bioreaction containers in the form of sample wells 546 in which are disposed cell cultures to be tested for cell culture performance. A sample monitoring structure 508 of this disclosure, including the fluorescently-labeled hydrogel, is also disposed in each of the sample wells 546 in contact with the culture medium in each sample well 546. The sample monitoring structure may be in the form of the sample monitoring beads, which may be retained in a fixed position within each sample well (e.g., in a sensor spot located in a fixed position on an inside surface of each sample well 546) or may be dispersed throughout the culture media. Alternatively, or additionally, each sample well 546 may include a sample monitoring structure not in the form of the sample monitoring beads. The cell cultures in the sample wells include cells and culture media to support growth of the cells. The live cell imaging and analysis system 540 includes a movable sensor module 548 with investigatory componentry for analysis of conditions within the sample wells 546. The sensor module 548 is translatable along a rail member 562, and the rail member 562 is supported by and translatable along the lengths of two other rail members 564a,b. Thus, the sensor module 548 can be horizontally positioned below each of the sample wells 546 to perform an analysis of properties within each sample well 546. Also, the sensor module 548 can be mounted with vertical adjustment capability, to permit the sensor module to be moved closer to or farther from a sample well 546 during an analytical evaluation or during movement between different sample wells 546 between analytical evaluations. The sensor module 548 can be robotically repositioned between different sample wells 546 at the direction and control of a data evaluation and control system 550, which also receives and processes analytical information received from the sensor module 548 resulting from analytical evaluations of the sample wells 546. As shown in FIG. 19, the data evaluation and control system 550 includes a computer processor 552, a computer memory 554 with instructions executable by the computer processor 552, and a user interface 556 including a data input system 560 and video display 558. The data evaluation and control system 550 and components thereof may be similar to and operate as described for the data evaluation and control system 520 of FIG. 18 and or the data evaluation and control system 350 of FIG. 15, but programmed with instructions stored in the memory 554 for operation and control of the sensor module 548 and for evaluation of analytical information received from the sensor module 548 from analytical evaluations performed on the sample wells 546. As will be appreciated, within the context of the general example analytical system of FIG. 18, each sample well 546 includes its own investigation zone within the containment volume of the sample well 546.

With continued reference to FIG. 19, the live cell imaging and analysis system 540 can provide significant capabilities to investigate different properties within the sample wells 546. In the example embodiment illustrated in FIG. 19, the sensor module 548 includes investigation componentry including one or more radiation emitters to direct radiation (e.g., light) to inside of a sample well 546 under investigation to investigate properties of contents within the sample well 546. Such investigation componentry will include at least componentry with capability to provide the stimulation radiation to elicit the fluorescent response from the sample monitoring structure in the sample wells 546, but may also include capabilities to provide one or more other stimuli for one or more other investigatory purposes. The investigation componentry in the sensor module 548 also includes one or more radiation detectors to detect radiation (e.g., light) coming from the sample well 546 under investigation. The detected radiation may be in response to stimulation radiation emitted from the sensor module 548 or from stimulus provided by different source than the sensor module 548. The example live cell imaging and analysis system 540 of FIG. 19 also includes a phase lamp 566 to illuminate contents of the sample wells 546 inside of the incubator 542, to permit the sensor module 548 to acquire phase contrast image data as desired. The investigation componentry of the sensor module 548 includes at least componentry to acquire for analysis fluorescent emission signals from the sample monitoring structure in the sample wells 546.

The actual radiation sources for radiation emitted from the sensor module 548 and/or the actual radiation detectors for radiation signals acquired through the sensor module 548 may be located on the sensor module 548 itself or may be located remote to the sensor module 548, with radiation signals transmitted between the sensor module 548 and the actual radiation sources and/or radiation detectors by appropriate radiation signal conductors (e.g., optical fibers).

The data evaluation and control system 550 may be programmed to perform an investigation of the sample monitoring structure in the sample wells 546 and any other investigation to be performed on a sample well 546 contemporaneously or at a different time than an investigation of the sample monitoring structure in a sample well 546. The data evaluation and control system 550 may be programmed to permit the user to instruct an ad hoc investigation be performed on a particular sample well 546. Alternatively or additionally, the data evaluation and control system 550 may be programmed to receive instructions to investigate a plurality of the sample wells 546 identified by a user to be automatically robotically investigated by the sensor module 546 in an identified sequence of investigation. The sequence may include performing an investigation of the sample monitoring structure of each investigated sample well 546 and may include also performing one or more other investigations while the sensor module 548 is positioned at a sample well 546 during the sequence, to contemporaneously perform a sequence of one or more other investigations. The data evaluation and control system 550 may perform such sequences periodically, which may include time-lapse images of cells or portions thereof, and the data evaluation and control system 550 may correlate (e.g., time correlation) different investigations performed in such contemporaneously performed sequences. For example, results of investigations for the fluorescent emission of the sample monitoring structure and evaluation of a condition of the culture media may be correlated with different time-lapse images.

In the illustration of the live cell imaging and analysis system 540 shown in FIG. 19, the data evaluation and control system 550 is shown connected to the sensor module 548 through the track member 562. As will be appreciated, the data evaluation and control system 550 can also be connected with other controllable features, for example the phase lamp 566 and/or environmental control elements (e.g., heaters, coolers, humidifiers, carbon dioxide gas supply).

Figure 20:
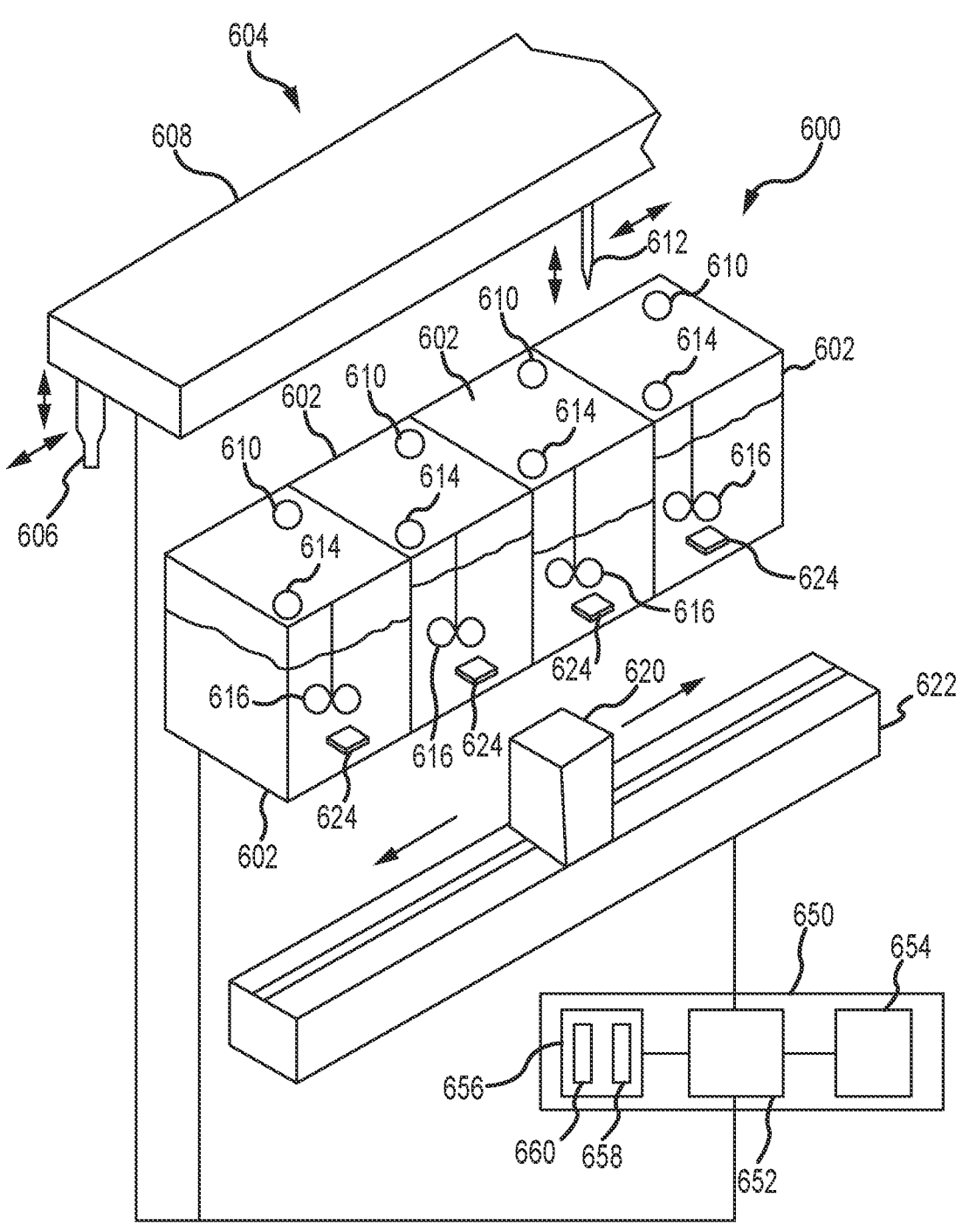
FIG. 20 is an illustration of an example of a parallel bioreactor system for use with the sample monitoring structure.

Reference is now made to FIG. 20, illustrating features of an analytical system in the form of an example parallel bioreactor system 600. As shown in FIG. 20, the parallel bioreactor system 600 includes a plurality of bioreaction containers in the form of bioreactors 602 configured to be operated in parallel at the direction and control of a data evaluation and control system 650. The parallel reactor system 600 also includes an automated liquid handler 604 which is part of an automated liquid handling system to robotically make liquid additions to the bioreactors 602 at the direction and control of the data evaluation and control system 650. The liquid handler 604 includes a fluid dispensation tip 606 that is translatable longitudinally along a track member 608, and additionally the dispensation tip 606 is mounted on a vertical adjustment mechanism configured to raise and lower the elevation of the dispensation tip 606 to permit the dispensation tip 606 to be lowered to extend into a fluid inlet port 610 to make liquid additions to a bioreactor 602 and to be raised out of the fluid inlet port 610 after completion of such a liquid addition. The dispensation tip 606 may be a single-use piece that may be discarded after each use and replaced with a new dispensation tip 606 to be used for the next liquid addition. The automated liquid handling system of the parallel bioreactor system 600 may also include reagent stations where the dispensation tip 606 may be manipulated to mix liquid formulations or addition to a bioreactor 602, for example to prepare growth media additions containing desired growth nutrients for addition to a bioreactor 602. The automated liquid handling system may also include cleaning stations to permit cleaning fluid to be flushed through liquid lines as needed.

With continued reference to FIG. 20, the liquid handler 604 also includes a liquid withdrawal needle 612 that may be translated longitudinally along the track member 608 independent of the dispensation tip 606. The liquid withdrawal needle 612 may, for example, be translated along the length of the track member 608 in a separate, different translation track within the track member 608 than a track in which the dispensation tip 606 is translated. The liquid withdrawal needle 612 is also mounted on a vertical adjustment mechanism configured to raise and lower the elevation of the liquid withdrawal needle 612. As with operation of the dispensation tip 606, the liquid withdrawal needle 612 may be manipulated at the direction of the data evaluation and control system 650. The liquid withdrawal needle 612 can be moved and positioned to correspond with locations of liquid withdrawal ports 614 of the bioreactors 602, and may be lowered through a liquid withdrawal port 614 into liquid within the corresponding bioreactor 602 to suction some or even substantially all of the liquid from the bioreactor 602. For example, the liquid withdrawal needle 612 can be operated to obtain a sample of cell culture or fermentation mixture for analysis, or to remove cell culture or fermentation mixture to permit liquid additions to modify conditions or to renew conditions for further cell culture or fermentation processing. The bioreactors 602 also include internal mixing impellers 616 which may be operated continuously or intermittently at the direction and control of the data evaluation and control system 650.

In some variations of the parallel bioreactor system 600 of FIG. 20, the parallel bioreactor system may include an automated fluid handling system, the operation and control of which is at the direction of the data evaluation and control system 650. The automated liquid handler 604 may be a part of such an automated fluid handling system. Such an automated fluid handling system may be configured to operate, at the direction of the data evaluation and control system 650, to automatically make liquid additions to one or more of the bioreactors 602 other than through use of the dispensation tip 606 of the automated liquid handler. For example, such an automated fluid handling system could include one or more pumps, or a pressurized liquid delivery system, fluidly connected with the interior containment volume of a bioreactor 602 to make a liquid addition by pumping or by conveyance through such a pressurized liquid delivery system. Such an automated fluid handling system could be configured, for example, with one or more compressors and/or a pressurized gas delivery system fluidly connected to the interior containment volume of a bioreactor 602, to introduce gas into the bioreactor. Such gas delivery to a bioreactor 602 could be for example gas addition to a gas headspace in a bioreactor 602 and/or by sparging gas into the growth medium in the bioreactor 602. Such a gas could, for example, be or include carbon dioxide to support growth of biological material. Such an automated fluid handling system could be configured to make both such liquid additions and gas additions separately from the automated liquid handler 604. Such an automated fluid handling system could be configured to provide a multi-phase fluid addition including both liquid and gas together. The parallel bioreactor system 600 also includes a sensor module 620 that is translatable along a rail member 622 to position the sensor module 620 relative to each of the bioreactors 602 to perform an analysis of properties within each of the bioreactors 602. The sensor module 620 may be mounted with vertical adjustment capability, to permit the sensor module 620 to be raised and lowered relative to the bioreactors 602 for better vertical positioning relative to the bioreactors 602 to perform an analysis and/or to facilitate movement between bioreactors 602. In the example illustrated in FIG. 20, each of the bioreactors 602 has inside the containment volume a sensor spot 624. Various sensor elements may be investigated by the sensor module 620 to provide readings on various properties of the growth medium within a bioreactor 602. The sensor spot 624 can include an immobilized form of the sample monitoring structure with a fluorescently-labeled hydrogel, which can be in the form of sample monitoring beads or other form. Additionally, or alternatively, sample monitoring beads may be dispersed in the growth medium within the bioreactors 602 and may be analyzed separately from the sensor spot 624, for example by positioning the sensor module 620 adjacent to the bottom of the bioreactor 602 but not opposite the sensor spot 624. Accordingly, the sensor module 620 may be robotically repositioned as desired between different bioreactors 602 at the direction and control of the data evaluation and control system 650, which also receives and processes analytical information received from the sensor module 620 resulting from analytical evaluations of the bioreactors 602. As shown in FIG. 20, the data evaluation and control system 650 includes a computer processor 652, a computer memory 654 with instructions executable by the computer processor 652, and a user interface 656 including a data input system 660 and a video display 658. The data evaluation and control system 650 and components thereof may be similar to and operate as described for the data evaluation and control system 550 of FIG. 19, the data evaluation and control system 520 of FIG. 18 or the data evaluation and control system 350 of FIG. 15, but programmed with instructions stored in the memory 654 for operation and control of the sensor module 620 and for evaluation of analytical information received from the sensor module 620 from analytical evaluations performed on the bioreactors 602. As will be appreciated, within the context of the general example analytical system of FIG. 18, each bioreactor 602 includes its own investigation zone within the containment volume of the bioreactor 602.

The parallel bioreactor system 600 can provide significant capabilities to investigate different properties within the bioreactors 602. In the example embodiment illustrated in FIG. 20, the sensor module 620 includes investigation componentry including one or more radiation emitters to direct radiation (e.g., light or electronic signals) to inside the bioreactor 602 to take analytical readings. Such analytical readings may be taken of sensor elements on the sensor spot 624 or may be positioned to take an analytical reading directly on the growth media, for example to investigate for florescent emission sample monitoring beads dispersed in growth medium within the bioreactor 602. In the example parallel bioreactor system 600 of FIG. 20, the sensor module 620 includes at least investigation componentry to provide the stimulation radiation to elicit the florescent emission response from the sample monitoring structure and to acquire for analysis the resulting florescent emission response. The actual radiation source for radiation emitted from the sensor module 620 and/or the actual radiation detectors for radiation signals acquired through the sensor module 620 may be located on board the sensor module 620 or may be located remote to the sensor module 620, with radiation signals transmitted between the sensor module 548 and the actual radiation sources and/or radiation detectors by appropriate radiation signal conductors (e.g., optical fibers).

The data evaluation and control system 650 may be programmed to perform an investigation of the sample monitoring structure in a bioreactor 602 and any other investigation to be performed on a bioreactor 602 contemporaneously with, or at a different time than, investigation of the sample monitoring structure in the bioreactor 602. The data evaluation and control system 650 may be programmed to permit the user to instruct an ad hoc investigation be performed on a particular bioreactor 602. Alternatively or additionally, the data evaluation and system 650 may be programmed to receive instructions to investigate a plurality of the bioreactor 602 identified by the user to be automatically robotically investigated by the sensor module 620 in an identified sequence of investigation. The sequence may include performing an investigation of the sample monitoring structure of each investigated bioreactor 602 and may include also performing one or more other investigations while the sensor module 620 is positioned at a bioreactor 602 during the sequence, to contemporaneously perform a sequence of one or more other investigations. The data evaluation and control system 650 may perform such evaluation sequences on a periodic basis to monitor conditions over time in the bioreactors 602.

Example Implementation Combinations

Some other contemplated embodiments of implementation combinations for various aspects of this disclosure, with or without additional features as disclosed above or elsewhere herein, are summarized in the numbered paragraphs presented below, and in the appended claims:

1. A method for flow cytometry evaluation of an aqueous fluid sample, comprising:
    subjecting an aqueous fluid sample to flow cytometry evaluation, wherein:
        the fluid sample comprises a plurality of beads disposed in an aqueous liquid medium, the beads comprising a fluorescently-labeled hydrogel that changes in size in response to a change in at least one property of the fluid sample, and in response to stimulation radiation, the beads have a fluorescent emission that changes in intensity with changes in the size of the fluorescently-labeled hydrogel; and
    the flow cytometry evaluation comprises detecting the intensity of the fluorescent emission from the beads;
    and optionally, the flow cytometry evaluation comprises flowing the fluid sample through an investigation zone and in the investigation zone subjecting a flow of the fluid sample to stimulation radiation and detecting for response radiation from the investigation zone and further optionally the flowing comprises passing at least 100 of the beads through the investigation zone in the fluid sample.

2. The method of paragraph 1, wherein the beads comprise a fluorochrome and the fluorescent emission as detected during the detecting is at a relative fluorescence intensity of at least 25 molecules of equivalent soluble fluorochrome (MESF), preferably at least 50 MESF, more preferably at least 75 MESF, even more preferably at least 100 MESF and still more preferably at least 200 MESF.

3. The method of either one of paragraph 1 or paragraph 2, wherein the beads comprise a fluorochrome and the fluorescent emission as detected during the detecting is at a relative fluorescence intensity of not larger than 1,000,000 MESF, and often not larger than 500,000 MESF, or even not larger than 100,000 MESF. Many flow cytometers designed for analysis of cells, which often have a size in a range of from about 2 microns to about 20 microns, and similarly-sized particles, are often designed to operate down to a lower limit sometimes as low as 100 MESF, often not lower than 200 MESF or even not lower than 500 MESF or an even larger number. Some flow cytometers designed for analysis of virus-size particles such as exosomes, viruses, virus-like particles, bacteria, fungus, algae, and mycoplasma, which may have a size in a range of from about 25 nanometers to about one micron, may be designed to operate at lower MESF values that may sometimes have a lower limit selected from the group consisting of 25 MESF, 50 MESF and 75 MESF, and although the flow cytometers may be able to detect much larger fluorescence intensities, the fluorescence detected from such small particles is often not larger than 1,000 MESF.

4. The method of any one of paragraphs 1-3, wherein the fluid sample as subjected to the flow cytometry evaluation has a pH in a range of from pH 5.0 to pH 8.2.

5. The method of any one of paragraphs 1-4, wherein the fluid sample as subjected to the flow cytometry evaluation has a concentration of sodium chloride in a range of from 100 millimoles per liter to 800 millimoles per liter.

6. The method of any one of paragraphs 1-5, wherein the fluid sample as subjected to the flow cytometry evaluation has an osmolarity in a range of from 200 milliosmoles per liter to 1600 milliosmoles per liter, and preferably in a range of from 250 milliosmoles per liter to 500 milliosmoles per liter, and particularly when evaluating also for cells as target particles.

7. The method of any one of paragraphs 1-6, comprising:
prior to the flow cytometry evaluation, preparing the fluid sample with prepared properties, and optionally the fluid sample as prepared during the preparing is the fluid sample of any one of paragraphs 58-64; and
evaluating the detected response radiation from the beads detected during the detecting to identify changes in properties of the fluid sample as investigated in the investigation zone relative to the prepared properties, and optionally the evaluating the detected response radiation is part of the evaluating by the data evaluation and control system as recited in paragraph 9.

8. The method of paragraph 7, wherein the prepared properties comprise a pH in a range of from pH 5.5 to pH 8.2, optionally a sodium chloride concentration in a range of from 100 millimoles per liter to 800 millimoles per liter and preferably from 100 to 150 millimoles per liter, and further optionally an osmolarity in a range of from 200 milliosmoles per liter and 1600 milliosmoles per liter and preferably in a range of from 260 to 320 milliosmoles per liter. In some situations, it is preferred to prepare the fluid sample at a pH near physiological pH of about pH 7.4 (e.g. at pH 7.2 to pH 7.5). However, some cells (e.g., some insect cells) are sometimes prepared for flow cytometry at a pH as low as about pH 6.2 and some viral particles (e.g., some non-enveloped virions and virus-like particles) are prepared at a lower pH that may be as low as about pH 5.5).

9. The method of any one of paragraphs 1-8, wherein the detecting is performed by a radiation detection system and the flow cytometry system includes a data evaluation and control system in communication with the radiation detection system, the data evaluation and control system comprising a computer processor and computer memory with stored instructions executable by the computer processor, and the flow cytometry evaluation comprises:
evaluating by the data evaluation and control system executing the evaluation instructions an integrity of the fluid sample, comprising evaluating the detected response radiation from the beads in the fluid sample, and optionally including comparing a detected intensity of the fluorescent emission from the fluid sample to a reference criteria.

10. The method of paragraph 9, wherein the flow cytometry evaluation comprises generating by the computer processor, as a consequence of the evaluating by the data evaluation and control system identifying an integrity deficiency for the fluid sample, a sample integrity warning notification, and optionally storing the sample integrity warning notification in the computer memory.

11. The method of any one of paragraphs 1-10, wherein the detecting comprises detecting light scatter from the beads and correlating occurrences of detection of the light scatter with occurrences of detection of the fluorescent emission to identify occurrences of the beads.

12. The method of paragraph 11, wherein the correlating is performed by the data evaluation and control system of either one of paragraph 9 or paragraph 10 by the computer processor executing the evaluation instructions.

13. The method of any one of paragraphs 1-12, wherein the flow cytometry evaluation comprises detecting properties of the response radiation indicative of passage through the investigation zone of other particles, other than the beads, to evaluate the other particles for the presence of target particles.

14. The method of paragraph 13, wherein the other particles comprise particles of biological material.

15. The method of either one of paragraph 13 or paragraph 14, wherein the fluid sample comprises a sample of biological material with the other particles to be evaluated for the presence of the target particles.

16. The method of any one of paragraphs 13-15, wherein the target particles comprise particles selected from the group consisting of cells, blood components, extracellular vesicles including exosomes, viruses, virus-like particles, bacteria, fungus, algae, and mycoplasma.

17. The method of any one of paragraphs 13-16, wherein the fluid sample is stained with a fluorescent stain for fluorescent labeling of the target particles, wherein the fluorescent stain on labeled said target particles provides a second fluorescent emission response at a different peak wavelength than the fluorescent emission of the beads; and
the detecting comprises detecting for the second fluorescent emission response to identify occurrences of passage through the investigation zone of the target particles labeled with the fluorescent stain.

18. The method of paragraph 17, wherein the fluorescent stain comprises a fluorescent antibody stain with a fluorochrome conjugated to an antibody specific for binding with the target particles.

19. The method of any one of paragraphs 1-18, wherein the detecting comprises detecting light scatter from target particles, other than the beads, and optionally the method comprises correlating detected light scatter from the target particles with detection of the second fluorescent response of any one of either one of paragraphs 15 or 16 and correlating occurrences of detection of light scatter with occurrences of detection of the second fluorescent emission to identify occurrences of the target particles.

20. The method of any one of paragraphs 1-19, comprising subjecting a plurality of the fluid samples, each comprising the beads, to the flow cytometry evaluation in a sequence, and wherein:

different said fluid samples are evaluated for the same or different target particles, other than the beads; and optionally, the fluid samples are all pre-prepared prior to commencement of the flow cytometry evaluation on a first said fluid sample in the sequence.

21. The method of paragraph 20, comprising evaluating the fluorescent emissions from the beads detected for each of the fluid samples relative to a reference criteria to determine a sample integrity rating of the sample relative to sample integrity criteria, optionally by the data control and analysis system of either one or paragraph 9 or paragraph 10.

22. The method of paragraph 21, comprising providing a sample integrity warning to an operator of the flow cytometry evaluation for a fluid sample failing to meet the sample integrity criteria, optionally at the direction of the computer processor of the data evaluation and control system of either one of paragraph 9 or paragraph 10.

23. The method of either one of any one of paragraphs 20-22, following failure of one or more said fluid samples to satisfy the sample integrity criteria, removing one or more remaining said fluid samples from the sequence.

24. The method of paragraph 23, wherein the removing comprises discontinuing the sequence prior to completion of the flow cytometry evaluation of all of the plurality of the fluid samples.

25. The method of any one of paragraphs 20-24, wherein the plurality of the fluid samples comprises a group of said fluid samples in separate sample containers retained in a tray, and the method comprises withdrawing by an autosampler an evaluation volume of the fluid samples in the sequence for the flow cytometry evaluation.

26. The method of paragraph 25, wherein the plurality of the fluid samples comprises multiple said groups of fluid samples with each said group retained in a separate said tray and the method comprises sequential processing of the trays for the flow cytometry evaluation.

27. The method of paragraph 26, comprising loading the trays for the sequential processing into a robotically-accessible storage structure; and wherein the sequential processing of the trays comprises automated robotic transferring of the trays in a tray sequence from the storage structure to the autosampler for performing the withdrawing of fluid samples from each of the trays.

28. The method of any one of paragraphs 20-27, wherein a time period for performing the sequence of the flow cytometry is at least one hour.

29. The method of any one of paragraphs 20-28, wherein a time period for performing the sequence of the flow cytometry is up to 72 hours.

30. The method of any one of paragraphs 1-29, wherein;

the flow cytometry evaluation is performed using a flow cytometry system, the flow cytometry system comprising:

the investigation zone;

a radiation delivery system configured to provide the stimulation radiation to the investigation zone;

a radiation detection system configured to perform the detecting for response radiation from the investigation zone; and a sample delivery system configured to withdraw from a sample container and conduct to the investigation zone an evaluation volume of the fluid sample; and the fluid sample comprises other particles disposed in the aqueous liquid medium for flow cytometry evaluation, the other particles being other than the beads, and prior to the flow cytometer evaluation the fluid sample is contained in a sample container from which an evaluation volume of the fluid sample is withdrawn for the flow cytometry evaluation.

31. A flow cytometry system for flow cytometry evaluation of a fluid sample, comprising:

a flow cytometry investigation system, comprising:

an investigation zone configured to receive during a flow cytometry evaluation a flow of a fluid sample comprising a plurality of beads disposed in an aqueous liquid medium;

a radiation delivery system configured to provide stimulation radiation to the investigation zone for investigation of the fluid sample in the investigation zone; and a radiation detection system configured to detect response radiation from the fluid sample in the investigation zone in response to the stimulation radiation;

a sample delivery system configured to interface with a sample container containing the fluid sample and to withdraw from the sample container and transfer to the investigation zone an evaluation volume of the fluid sample for the flow cytometry evaluation;

a data evaluation and control system in communication with the radiation detection system, the data evaluation and control system comprising a computer processor and computer memory with stored instructions executable by the computer processor to evaluate detected radiation information from the radiation detection system during the flow cytometry evaluation;

and wherein:

the beads comprise a fluorescently-labeled hydrogel that changes in size in response to a change in at least one property of the fluid sample;

an intensity of a fluorescent emission from each said bead in the fluid sample in response to the stimulation radiation changes with changes in the size of the fluorescently-labeled hydrogel;

the radiation detection system is configured to detect a range of fluorescent emission intensities corresponding to a range of sizes of the beads in the fluid sample; and the data evaluation and control system is configured to evaluate an integrity of the fluid sample, including evaluating the detected response radiation from the beads in the fluid sample.

32. The system of paragraph 31, wherein the evaluation of the integrity of the fluid sample comprises evaluating the detected response radiation from the beads in the fluid sample relative to a reference criteria, and optionally including comparing a detected intensity of the fluorescent emission from the fluid sample to a reference intensity criteria.

33. The system of either one of paragraph 31 or paragraph 32, wherein the data evaluation and control system is configured to generate, by the computer processor as a consequence of a said evaluation of integrity of the fluid sample, a sample integrity warning notification when the data evaluation and control system identifies an integrity deficiency for the fluid sample.

34. The system of paragraph 33, wherein the data evaluation and control system is configured to store, at the direction of the computer processor, the sample integrity warning notification in the computer memory.

35. The system of any one of paragraphs 31-34, comprising a said sample container containing the fluid sample, the said sample container being interfaced with the sample delivery system.

36. A flow cytometry system, comprising:

a flow cytometry investigation system;

a sample container;

an aqueous fluid sample contained in the sample container; and a sample delivery system configured to interface with the sample container and to withdraw from the sample container and transfer to the flow cytometry investigation system an evaluation volume of the fluid sample for flow cytometry evaluation;

and wherein:

the fluid sample comprises a plurality of beads disposed in an aqueous liquid medium;

each said bead comprises a fluorescently-labeled hydrogel that changes in size in response to a change in at least one property of the fluid sample; and in response to stimulation radiation, an intensity of a fluorescent emission from a said bead changes with changes in the size of the fluorescently-labeled hydrogel;

and optionally the flow cytometry investigation system may include:

an investigation zone to receive the flow of the fluid sample during the flow cytometry evaluation;

a radiation delivery system configured to provide stimulation radiation to the investigation zone for investigation of the fluid sample in the investigation zone; and a radiation detection system configured to detect a response radiation from the fluid sample in the investigation zone in response to the stimulation radiation.

37. The system of paragraph 36, wherein the flow cytometry system includes a data evaluation and control system in communication with the radiation detection system, the data evaluation and control system comprising a computer processor and computer memory with stored instructions executable by the computer processor to evaluate the detected response radiation from the radiation detection system.

38. The system of paragraph 37, wherein the data evaluation and control system is configured to perform evaluation of integrity of the fluid sample, including evaluating the detected response radiation from the beads in the fluid sample relative to a reference criteria.

39. The system of paragraph 38, wherein the evaluation of integrity of the fluid sample comprises comparing a detected intensity of the fluorescent emission from the fluid sample to a reference intensity criteria.

40. The system of either one of paragraph 38 or paragraph 39, wherein the data evaluation and control system is configured to generate, by the computer processor as a consequence of a said evaluation of integrity of the fluid sample, a sample integrity warning notification and to store the sample integrity warning notification in the computer memory.

41. The method or system of any one of paragraphs 30-40, wherein the radiation detection system is configured to detect light scatter.

42. The method or system of paragraph 41, wherein the flow cytometry system comprises the data evaluation and control system of any one of paragraphs 31-35 and 37-40 and the data evaluation and control system is configured to correlate occurrences of detection of light scatter with occurrences of detection of the fluorescent emission to identify occurrences of the beads.

43. The method or system of any one of paragraphs 30-42, wherein the radiation detection system is configured to perform detecting properties of the response radiation indicative of passage through the investigation zone of other particles, other than the beads, to evaluate the other particles for the presence of target particles, optionally by the data evaluation and control system of any one of paragraphs 31-35 and 37-40.

44. The method or system of paragraph 43, wherein the fluid sample comprises the other particles, and optionally the other particles are particles of biological material.

45. The method or system of either one of paragraph 43 or 44, wherein the fluid sample comprises the target particles, and optionally the flow cytometry system is fluidly connected to a bioreactor and the fluid sample comprises bioreactor medium from the bioreactor.

46. The method or system of any one of paragraphs 43-45, wherein the target particles comprise particles selected from the group consisting of cells, blood components, extracellular vesicles including exosomes, viruses, virus-like particles, bacteria, fungus, algae, and mycoplasma.

47. The method or system of any one of paragraphs 43-46, wherein the fluid sample is stained with a fluorescent stain for fluorescent labeling of the target particles, wherein the fluorescent stain on labeled said target particles provides a second fluorescent emission response at a different peak wavelength than the fluorescent emission of the beads; and the radiation detection system is configured to detect for the second fluorescent emission response to identify passage through the investigation zone of the target particles labeled with the fluorescent stain.

48. The method or system of paragraph 47, wherein the fluorescent stain comprises a fluorescent antibody stain with a fluorochrome conjugated to an antibody specific for binding with the target particles.

49. The method or system of any one of paragraphs 30-48, wherein;

the flow cytometry system comprises a plurality of the fluid samples, each said fluid sample being contained in a separate said sample container and comprising the beads and other particles, other than the beads, for flow cytometry evaluation for target particles, and optionally the target particles may be the same for different ones of the fluid samples; and the flow cytometry system is configured to deliver each of the fluid samples to the investigation zone for flow cytometry evaluation in a sequence;

and optionally each said sample container comprises a bioreactor.

50. The method or system of paragraph 49, comprising the data evaluation and control system of any one of paragraphs 31-35 and 37-40, and wherein:

the data evaluation and control system is configured to evaluate the fluorescent emissions from the beads detected by the radiation detection system for each of the fluid samples relative to a reference criteria to determine a sample integrity rating of the sample relative to a sample integrity criteria.

51. The method or system of paragraph 50, wherein the data evaluation and control system is configured to provide a sample integrity warning for a fluid sample failing to meet the sample integrity criteria.

52. The method or system of either one of paragraph 50 or paragraph 51, wherein the flow cytometry system is configured to perform removing one or more of the fluid samples from the sequence, and optionally the removing comprises discontinuing the sequence as a consequence of failure of one or more said fluid samples to satisfy the sample integrity criteria, and optionally the removing is performed at the direction of the computer processor of the data evaluation and control system of any one of paragraphs 31-35 and 37-40.

53. The method or system of any one of paragraphs 50-52, wherein the plurality of the fluid samples comprises a group of said fluid samples in separate sample containers retained in a tray, and the flow cytometry system is configured to perform withdrawing by an autosampler an evaluation volume of the fluid samples in the sequence for the flow cytometry evaluation.

54. The method or system of paragraph 53, wherein the plurality of the fluid samples comprises multiple said groups of fluid samples with each said group retained in a separate said tray and the flow cytometry system is configured to perform sequential processing of the trays for the flow cytometry evaluation.

55. The method or system of any one of paragraph 54, wherein the sequential processing of the trays comprises automated robotic transferring of the trays in a tray sequence from a storage structure to the autosampler for performing the withdrawing on fluid samples of each of the trays in the tray sequence.

56. The method or system of any one of paragraphs 49-55, wherein the flow cytometry system is configured to perform the sequence of the flow cytometry over a time period of at least one hour.

57. The method or system of any one of paragraphs 49-56, wherein the flow cytometry system is configured to perform the sequence of the flow cytometry over a time period of up to 72 hours.

58. An aqueous fluid sample for flow cytometry evaluation, the fluid sample comprising:

an aqueous liquid medium, including a plurality of beads and other particles dispersed therein for flow cytometry evaluation for a presence of target particles, the other particles being different than the beads;

the beads comprising a fluorescently-labeled hydrogel, wherein the beads have a fluorescent emission when subjected to a stimulation radiation, and the fluorescently-labeled hydrogel changes in size in response to a change in at least one property of the fluid sample; and in response to the stimulation radiation, the beads have a fluorescent emission that changes in intensity with changes in the size of the fluorescently-labeled hydrogel.

59. The method, system or fluid sample of any one of paragraphs 30-58, wherein the beads comprise a fluorochrome and the beads in the fluid sample provide a relative fluorescence intensity in response to the stimulation radiation of at least 25 molecules of equivalent soluble fluorochrome (MESF), preferably at least 50 MESF, more preferably at least 75 MESF, even more preferably at least 100 MESF and still more preferably at least 200 MESF and in many cased most preferably at least 300 MESF.

60. The method, system or fluid sample of any one of paragraphs 30-59, wherein the beads comprise a fluorochrome and the beads in the fluid sample provide a relative fluorescence intensity in response to the stimulation radiation of not larger than 1,000,000 MESF, often not larger than 500,000 MESF, or even not larger than 100,000 MESF, and for operation with many flow cytometers with very small beads, on the order of the size of virus particles (e.g., 25 nanometers to on micron), the beads in the fluid sample may provide a relative fluorescence intensity in response to the stimulation radiation of often not larger than 5,000 MESF.

61. The method, system or fluid sample of any one of paragraphs 30-60, wherein the fluid sample has a pH in a range of from pH 5.0 to pH8.2.

62. The method, system or fluid sample of any one of paragraphs 30-61, wherein the fluid sample has a concentration of sodium chloride in a range of from 100 millimoles per liter to 800 millimoles per liter, and optionally in a range of from 100 millimoles per liter to 200 millimoles per liter.

63. The method, system or fluid sample of any one of paragraphs 30-62, wherein the fluid sample has an osmolarity in a range of from 200 milliosmoles per liter to 1600 milliosmoles per liter, and optionally in a range of from 260 milliosmoles per liter to 320 milliosmoles per liter.

64. The method, system or fluid sample of any one of paragraphs 1-63, wherein the fluid sample has a number concentration of the beads of at least 100 of the beads per milliliter, preferably at least 1,000 of the beads per milliliter and more preferably at least 10,000 of the beads per milliliter, and optionally the fluid sample has a number concentration of the beads not greater than $1 \times 10^7$ of the beads per milliliter, preferably not greater than $1 \times 10^6$ of the beads per milliliter and more preferably not greater than 100,000 of the beads per milliliter.

65. A product for use in monitoring an aqueous fluid sample during flow cytometry evaluation of the fluid sample, the product comprising:

a plurality of beads for inclusion in an aqueous liquid medium of an aqueous fluid sample to monitor the fluid sample during flow cytometry evaluation, the beads having a fluorescent emission when subjected to a stimulation radiation during flow cytometry, and each said bead comprising:

a non-hydrogel core and a shell layer of fluorescently-labeled hydrogel surrounding the core;

wherein the fluorescently-labeled hydrogel changes in size in response to a change in at least one property of the aqueous fluid sample; and wherein an intensity of the fluorescent emission from the bead changes with changes in the size of the fluorescently-labeled hydrogel.

66. A product for use in monitoring an aqueous fluid sample during flow cytometry evaluation of the fluid sample, the product comprising:

a plurality of beads for inclusion in an aqueous liquid medium of an aqueous fluid sample to monitor the fluid sample during flow cytometry evaluation, the beads having a fluorescent emission when subjected to a stimulation radiation during flow cytometry;

each said bead comprising a fluorescently-labeled hydrogel that is size-responsive in the aqueous liquid medium, wherein an intensity of the fluorescent emission from the bead changes with changes in the size of the fluorescently-labeled hydrogel; and the beads having reference-state properties in a reference-state aqueous composition, wherein the reference-state aqueous composition comprises the beads dispersed in the aqueous liquid medium and the reference-state properties comprise a reference-state particle size of the beads in a range of from 2 microns to 25 microns, and preferably in a range of from 3 microns to 15 microns.

67. A product for use in monitoring an aqueous fluid sample during flow cytometry evaluation of the fluid sample, the product comprising:

a plurality of beads in an aqueous liquid medium of an aqueous fluid sample to monitor the fluid sample during flow cytometry evaluation, the beads having a fluorescent emission when subjected to a stimulation radiation during flow cytometry;

each said bead comprising a fluorescently-labeled hydrogel that is size-responsive in the aqueous liquid medium, wherein an intensity of the fluorescent emission from the bead changes with changes in the size of the fluorescently-labeled hydrogel;

the fluorescently-labeled hydrogel comprises a plurality of a first fluorochrome moieties and a plurality of a second fluorochrome moieties;

the first fluorochrome moiety has a first fluorescent emission in response to the stimulation radiation and the second fluorochrome moiety has a second fluorescent emission, different than the first fluorescent emission, in response to stimulation by the first fluorescent emission; and the fluorescent emission of the beads comprises the second fluorescent emission, and the second fluorescent emission decreases as the size of the hydrogel increases with a corresponding increase in spacing between occurrences of the first fluorochrome moiety and occurrences of the second fluorochrome moiety.

68. The product of any one of paragraphs 65-67, wherein the product comprises a mixture comprising the fluorescent beads disposed in an aqueous storage liquid.

69. The product of paragraph 68, wherein the mixture is contained in a sealed container.

70. The product of either one of paragraph 68 or paragraph 69, wherein the mixture is in the absence of other particles, other than the beads.

71. The product of any one of paragraphs 68-70, wherein the aqueous storage liquid has a pH in a range of from pH 7.2 to pH 7.6.

72. The product of any one of paragraphs 68-71, wherein the aqueous storage liquid has a concentration of sodium chloride in a range of from 100 millimoles per liter to 200 millimoles per liter.

73. The product of any one of paragraphs 68-72, wherein the aqueous storage liquid has an osmolarity in a range of from 200 milliosmoles per liter to 400 milliosmoles per liter.

74. The product of any one of paragraphs 68-73, wherein the mixture comprises a number concentration of the beads of at least an amount selected from the group consisting of 10,000 of the beads per milliliter, 100,000 of the beads per milliliter and 1,000,000 of the beads per milliliter;

and optionally the mixture comprises a number concentration of the beads not greater than an amount selected from the group consisting of $1\times10^9$ of the beads per milliliter, $1\times10^8$ of the beads per milliliter and $1\times10^7$ of the beads per milliliter.

75. The method, system, fluid sample or product of any one of paragraphs 1-64 and 66-74, wherein the beads comprise a core-shell structure with a non-hydrogel core and a shell layer of fluorescently-labeled hydrogel surrounding the core.

76. The method, system, fluid sample or product of either one of paragraph 65 or paragraph 75, wherein the core has a size in a range having an lower limit selected from the group consisting of 1 micron, 1.5 microns and 2 microns and an upper limit selected from the group consisting of 20 microns, 15 microns and 10 microns, and with one preferred range being from 2 microns to 10 microns.

77. The method, system, fluid sample or product of any one of paragraphs 65, 75 and 76, wherein the core comprises a material of construction selected from the group consisting of an organic material and an inorganic material;

when the material of construction comprises an organic material, the organic material may optionally comprise a polymeric material;

when the material of construction comprises an inorganic material, the inorganic material may optionally comprise a metal oxide or a ceramic material, with one preferred metal oxide being silica;

when the material of construction comprises a metallic material, the metallic material may optionally be a single-metal composition, an intermetallic compound or a metal alloy, and optionally the metallic material may comprise a metal selected from the group consisting of platinum, silver, gold and palladium.

78. The method, system, fluid sample or product of any one of paragraphs 65 and 75-77, wherein the core is:

comprised of a polymeric material comprising a member selected from the group consisting of polystyrene, polyethylene, polypropylene, agarose, Sepharose® and cellulose.

79. The method, system, fluid sample or product of any one of paragraphs 65 and 75-78, wherein the core has a density in a range of from 0.5 grams per cubic centimeter to 5 grams per cubic centimeter.

80. The method, system, fluid sample or product of any one of paragraphs 65 and 75-79, wherein the core has a refractive index of at least 1.1, and optionally the refractive index is at least 1.4;

and in either case optionally the refractive index is up to 1.8.

81. The method, system, fluid sample or product of any one of paragraphs 65 and 75-80, wherein the hydrogel is immobilized about the core by physisorption to the core.

82. The method, system, fluid sample or product of any one of paragraphs 65 and 75-80, wherein the hydrogel is immobilized about the core through covalent attachment to the core.

83. The method, system, fluid sample or product of paragraph 82, wherein the covalent attachment is through a covalent linkage selected from the group consisting of ester linkages, ether linkages, amide linkages, carbon-carbon single bonds, and carbon-carbon multiple bonds.

84. The method, system, fluid sample or product of any one of paragraphs 65 and 75-83, wherein the shell layer of the fluorescently-labeled hydrogel has a maximum expansion thickness selected from the group consisting of at least 10 nanometers, at least 25 nanometers, at least 100 nanometers and at least 1 micron, and in any case may optionally have a maximum expansion thickness selected from the group consisting of up to 20 microns, up to 10 microns or up to 5 microns, with one preferred range being from 100 nanometers to 10 microns.

85. The method, system, fluid sample or product of any one of paragraphs 65 and 75-84, wherein the fluorescently-labeled hydrogel has a minimum contraction thickness of at least an amount selected from the group consisting of at least 1 nanometer and 10 nanometers and 100 nanometers, and optionally the minimum contraction thickness is not greater than an amount selected from the group consisting of 2 microns and 1 micron, with one preferred range being from 1 nanometer to 1 micron. As may be appreciated, minimum contraction thickness may sometimes be on the order of 95% smaller than the maximum expansion thickness for some hydrogels.

86. The method, system, fluid sample or product of any one of paragraphs 1-85, wherein the beads comprise a core-shell structure with a non-hydrogel core and a shell layer of fluorescently-labeled hydrogel surrounding the core.

87. The method, system, fluid sample or product of paragraph 86, wherein the fluorescently-labeled hydrogel consists essentially of polymeric material that is not cross-linked other than through attachment to the core.

88. The method, system, fluid sample or product of any one of paragraphs 1-64 and 66-74, wherein the beads consist essentially of only the fluorescently-labeled hydrogel.

89. The method, system or fluid sample of any one of paragraphs 1-64 and 88, wherein the beads have a size in a range of from 25 nanometers to 1.5 microns, with one preferred range being in a range of from 25 nanometers to 600 nanometers and another preferred range being from 50 nanometers to 300 nanometers. The combinations of this paragraph are particularly advantageous for applications involving flow cytometry of virus-size particles, for example any of such particles disclosed elsewhere herein (e.g., of a size in a range of from about 25 nanometers to about one micron).

90. The method, system or system of any one of paragraphs 1-65 and 67-89, wherein the beads have reference-state properties in a reference-state aqueous composition, wherein the reference-state aqueous composition comprises the beads dispersed in an aqueous liquid and the reference-state properties comprise a reference-state particle size of the beads in a range of from 2 microns to 25 microns, and preferably in a range of from 3 microns to 15 microns.

91. The method, system, fluid sample or product of either one of paragraph 66 or paragraph 90, wherein the beads comprise a fluorochrome and the reference-state properties comprise a reference-state relative fluorescence intensity in a range having a lower limit selected from the group consisting of 50 molecules of equivalent soluble fluorochrome (MESF), 100 MESF, 200 MESF, 300 MESF and 1,000 MESF and an upper limit selected from the group consisting of 1,000,000 MESF, 500,000 MESF, 100,0000 MESF, 10,000 MESF and 5,000 MESF, with one preferred range being from 1,000 MESF to 500,000 MESF. As will be appreciated, the reference-state relative fluorescence intensity will be dependent on the size of the beads and the number of fluorochrome groups included in the beads 92. The method, system, fluid sample or product of any one of paragraphs 66, 90 and 91, wherein the reference-state aqueous liquid composition is at a reference-state temperature of about 27° C.

93. The method, system, fluid sample or product of any one of paragraphs 66 and 90-92, wherein the reference-state properties comprise a reference-state pH in a range of from pH 7.2 to pH 7.6 and preferably at about pH 7.4.

94. The method, system, fluid sample or product of any one of paragraphs 66 and 90-93, wherein the reference-state properties comprise a reference-state concentration of sodium chloride in a range of 100 to 150 millimoles per liter.

95. The method, system, fluid sample or product of any one of paragraphs 66 and 90-94, wherein the reference-state properties comprise a reference-state osmolarity in a range of from 260 to 320 milliosmoles per liter.

96. The method, system, fluid sample or product of any one of paragraphs 66 and 90-95, wherein the reference-state aqueous liquid composition is pH buffered with a buffer reagent, preferably comprising a carbonate buffer reagent, and more preferably comprising sodium bicarbonate.

97. The method, system, fluid sample or product of paragraph 96, wherein the reference state aqueous liquid comprises, and preferably consists essentially of, a culture medium formulation selected from the group consisting of MEM (Minimum Essential Medium), DMEM (Dulbecco's Modified Eagle's Medium). IMDM (Iscove's Modified Dulbecco's Medium), RPMI-1640, Ham's F-10 and F-12, McCoy's 5$^a$, Medium 199, and preferably the reference state aqueous liquid comprises a high-glucose DMEM with glucose at a concentration of 4500 mg/L and preferably under a 5% carbon dioxide atmosphere, and one example preferred high-glucose DMEM formulation comprises, and preferably consists essentially of, the following solutes in water at the following concentrations*:

| Solute | Concentration mg/L |
|---|---|
| Glycine | 30 |
| L-Arginine hydrochloride | 84 |
| L-Cystine-2HCl | 63 |
| L-Glutamine | 584 |
| L-Histidine hydrochloride-H2O | 42 |
| L-Isoleucine | 105 |
| L-Leucine | 105 |
| L-Lysine hydrochloride | 146 |
| L-Methionine | 30 |
| L-Phenylalanine | 66 |
| L-Serine | 42 |
| L-Threonine | 95 |

-continued

| Solute | Concentration mg/L |
|---|---|
| L-Tryptophan | 16 |
| L-Tyrosine disodium salt dihydrate | 104 |
| L-Valine | 94 |
| Choline chloride | 4 |
| D-Calcium pantothenate | 4 |
| Folic acid | 4 |
| i-Inositol | 7.2 |
| Niacinamide | 4 |
| Pyridoxine hydrochloride | 4 |
| Riboflavin | 0.4 |
| Thiamine hydrochloride | 4 |
| Calcium chloride (CaCl2) (anhydrous) | 200 |
| Ferric nitrate (Fe(NO3)3—9H2O) | 0.1 |
| Magnesium sulfate (MgSO4) (anhydrous) | 97.67 |
| Potassium chloride (KCl) | 400 |
| Sodium bicarbonate (NaHCO3) | 3700 |
| Sodium chloride (NaCl) | 6400 |
| Sodium phosphate monobasic (NaH₂PO₄—H₂O) | 125 |
| D-Glucose (dextrose) | 4500 |
| Phenol red | 15 |

*Published formulation of 11965-DMEM, high glucose (Thermo Fisher Scientific) and optionally the high-glucose DMEM formulation has an osmolarity in a range of from 260 to 320 milliosmoles and more preferably in a range of from 300 to 320 milliosmoles.

98. The method, system, fluid sample or product of any one of paragraphs 66 and 90-97, wherein the reference-state aqueous liquid composition comprises the beads at a reference-state number concentration of at least 10,000, and preferably not more than 1000,000 of the beads per milliliter.

99. The method, system, fluid sample or product of any one of paragraphs 66 and 90-98, wherein the reference-state aqueous liquid composition comprises, and preferably consists essentially of, a phosphate buffered saline (PBS) and preferably under a 5% carbon dioxide atmosphere, and preferably the PBS comprises, and more preferably consists essentially of, the following solutes in water:

| Solute | Concentration |
|---|---|
| sodium chloride (NaCl) | 137 mM |
| potassium chloride (KCl) | 2.7 mM |
| di-sodium hydrogen phosphate (Na₂HPO₄) | 10 mM |
| di-potassium hydrogen phosphate (K₂HPO₄) | 1.8 mM |
| sodium azide | 0.09% w/v | and optionally the PBS has an osmolarity in a range of from 280 to 315 milliosmoles 100. The method, system, fluid sample or product of any one of paragraphs 66 and 90-99, wherein:
the beads have modified-state properties in a modified-state aqueous composition, wherein the modified-state aqueous composition has one or more modified composition properties relative to the reference-state aqueous composition; and
the modified-state properties comprise a modified-state relative fluorescence intensity in response to a stimulation radiation that is different than a reference-state relative fluorescence intensity of the reference-state properties by a relative intensity increment of at least 5%, preferably at least 10%, more preferably at least 15% and even more preferably at least 20%, relative to the reference-state relative fluorescence intensity in units of molecules of equivalent soluble fluorochrome (MESF);

and optionally the modified-state properties comprise a modified-state relative fluorescence intensity in response to a stimulation radiation that is different than a reference-state relative fluorescence intensity of the reference-state properties by a relative intensity increment of not greater than 90%, preferably not greater than 80%, more preferably not greater than 70% and even more preferably not greater than 60%, relative to the reference-state relative fluorescence intensity in units of molecules of equivalent soluble fluorochrome (MESF).

101. The method, system, fluid sample or product of paragraph 100, wherein the modified-state relative fluorescence intensity is smaller than the reference-state relative fluorescence intensity by the intensity increment.

102. The method, system, fluid sample or product of paragraph 100, wherein the modified-state relative fluorescence intensity is larger than the reference-state relative fluorescence intensity by the intensity increment.

103. The method, system, fluid sample or product of any one of paragraphs 100-102, wherein the modified-state properties comprise a modified-state particle size that is different from the reference-state particle size by a size increment of at least 10 nanometers, preferably at least 20 nanometers and more preferably at least 30 nanometers;
and optionally, the modified-state particle size is different from the reference-state particle size by an amount selected from the group consisting of at least 3% of the reference-state size, at least 5% of the reference-state size, at least 10% of the reference-state size and at least 25% of the reference-state size.

104. The method, system, fluid sample or product of paragraph 103, wherein the modified-state particle size is smaller than the reference-state particle size by the size increment, and optionally the modified-state particle size is smaller than the reference-state particle size by no more than 50% of the reference-state particle size.

105. The method, system, fluid sample or product of paragraph 103, wherein the modified-state particle size is larger than the reference-state particle size by the size increment; and optionally the modified-state particle size is larger than the reference-state particle size by no more than 100% of the reference-state particle size.

106. The method, system, fluid sample or product of any one of paragraphs 100-105, wherein the modified-state properties comprise a pH of 0.3 pH units different, optionally larger or alternatively optionally smaller, than a pH of the reference-state aqueous composition, and preferably 0.3 pH units smaller than the pH of the reference state aqueous composition, and preferably with the modified-state aqueous composition being prepared in the same manner as the reference-state aqueous composition except with adjustment of the pH to the modified-state pH with addition of hydrochloric acid for pH reduction or sodium hydroxide for pH increase.

107. The method, system, fluid sample or product of any one of paragraphs 100-106, wherein the modified-state properties comprise a sodium chloride concentration of 50 micromoles per liter different, optionally larger or alternatively optionally smaller, than a sodium chloride concentration of the reference-state aqueous composition, and preferably larger than the sodium chloride concentration of the reference state aqueous composition.

108. The method, system, fluid sample or product of any one of paragraphs 100-107, wherein the modified-state properties comprise an osmolarity of 100 milliosmoles per liter different, optionally smaller or alternatively optionally larger, than an osmolarity of the reference-state aqueous composition, and preferably larger than the reference state aqueous composition; and preferably with the modified-state aqueous composition being prepared in the same manner as the reference-state aqueous composition and with adjustment of the water content relative to solutes to provide the adjustment of the osmolarity to the modified-state osmolarity.

109. The method, system, fluid sample or product of any one of paragraphs 1-108, wherein the hydrogel comprises a plurality of charged functional groups.

110. The method, system, fluid sample or product of paragraph 109, wherein the charged functional groups comprise anionic functional groups.

111. The method, system, fluid sample or product of paragraph 110, wherein the anionic functional groups are selected from the group consisting of sulfonic acid groups, sulfate groups, carboxylic acid groups, phosphate groups, phenolic groups, and combinations thereof.

112. The method, system, fluid sample or product of any one of paragraphs 109-111, wherein the charged functional groups comprise cationic functional groups.

113. The method, system, fluid sample or product of paragraph 112, wherein the cationic functional groups are amine groups, optionally selected from the group consisting of primary amines, secondary amines, tertiary amines, quaternary amines, and combinations thereof 114. The method, system, fluid sample or product of any one of paragraphs 109-113, wherein the charged functional groups comprise anionic functional groups and cationic functional groups.

115. The method, system, fluid sample or product of any one of paragraphs 1-114, wherein the fluorescently-labeled hydrogel comprises a polymeric material.

116. The method, system, fluid sample or product of any one of paragraphs 1-115, wherein the fluorescently-labeled hydrogel comprises a cross-linked polymer network.

117. The method, system, fluid sample or product of any one of paragraphs 1-116, wherein the fluorescently-labeled hydrogel comprises a polymer selected from the group consisting of glycidyl methacrylate;

(hydroxyethyl)methacrylate;

2-acrylamido-2-methylpropane sulfonic acid;

(2-(methacryloyloxy)ethyl)trimethylammonium chloride;

acrylic acid;

2-aminoethyl methacrylate hydrochloride;

2-(diethylamino)ethyl methacrylate;

2-(dimethylamino)ethyl methacrylate;

2-isocyanatoethyl methacrylate;

[3-(methacryloylamino)propyl]trimethylammonium chloride;

[2-(methacryloyloxy)ethyl]dimethyl-(3-sulfopropyl)ammonium hydroxide;

3-sulfopropyl methacrylate;

2-ethylacrylic acid;

2-propylacrylic acid;

any acrylate, methacrylate, acrylamide, methacrylamide or N-alkylacrylamide analog of any of the foregoing; and combinations thereof.

118. The method, system, fluid sample or product of any one of paragraphs 1-117, wherein the intensity of the fluorescent emission of the beads increases with an increase in size of the fluorescently-labeled hydrogel.

119. The method, system, fluid sample or product of paragraph 118, wherein the fluorescently-labeled hydrogel comprises a plurality of fluorochrome moieties, and quenching of fluorescent emissions from the fluorochrome moieties decreases as the size of the hydrogel increases with a corresponding increase in spacing between occurrences of the fluorochrome moieties.

120. The method, system, fluid sample or product of any one of paragraphs 1-117, wherein the intensity of the fluorescent emission of the beads decreases with an increase in size of the fluorescently-labeled hydrogel; and optionally:

the fluorescently-labeled hydrogel comprises a plurality of first fluorochrome moieties and a plurality of second fluorochrome moieties;

the first fluorochrome moiety has a first fluorescent emission in response to the stimulation radiation and the second fluorochrome moiety has a second fluorescent emission, different than the first fluorescent emission, in response to stimulation by the first fluorescent emission; and the fluorescent emission of the beads comprises the second fluorescent emission, and the second fluorescent emission decreases as the size of the hydrogel increases with a corresponding increase in spacing between occurrences of the first fluorochrome moiety and occurrences of the second fluorochrome moiety.

121. The method, system, fluid sample or product of any one of paragraphs 1-120, wherein when the fluorescently-labeled hydrogel is in contact with aqueous liquid, the size of the fluorescently-labeled hydrogel changes with changes in at least one property of the aqueous liquid in contact with the fluorescently-labeled hydrogel.

122. The method, system, fluid sample or product of paragraph 121, wherein the size of the fluorescently-labeled hydrogel changes with a change in pH of the aqueous liquid in contact with the fluorescently-labeled hydrogel over some pH range, and preferably the size of the hydrogel increases with an increase in the pH of the aqueous liquid in contact with the fluorescently-labeled hydrogel.

123. The method, system, fluid sample or product of paragraph 122, wherein the pH range includes a range member selected from the group consisting of:

from pH 5.0 to pH 5.5, from pH 5.5 to pH 6.5, from pH 6.5 to pH 7.5, from pH 7.5 to pH 8.5, and combinations of any two or any three adjacent ones of the foregoing; and optionally, the pH range includes from pH 5.0 to pH 8.5.

124. The method, system, fluid sample or product of any one of paragraphs 121-123, wherein the size of the fluorescently-labeled hydrogel changes with a change in concentration of sodium chloride in the aqueous liquid in contact with the fluorescently-labeled hydrogel over some range of sodium chloride concentration, and preferably the size of the hydrogel decreases with an increase in the concentration of sodium chloride of the aqueous liquid in contact with the fluorescently-labeled hydrogel.

125. The method, system, fluid sample or product of paragraph 124, wherein the range of sodium chloride concentration includes a range member selected from the group consisting of from 100 millimoles per liter to 200 millimoles per liter, from 200 millimoles per liter to 300 millimoles per liter, from 300 millimoles per liter to 800 millimoles per liter, and combinations of any two or three adjacent ones of the foregoing; and in one option the range may include from 100 millimoles per liter to 800 millimoles per liter.

126. The method, system, fluid sample or product of any one of paragraphs 121-125, wherein the size of the fluorescently-labeled hydrogel changes with a change in osmolarity in the aqueous liquid in contact with the fluorescently-labeled hydrogel over some range of osmolarity, and preferably the size of the hydrogel decreases with an increase in the osmolarity of the aqueous liquid in contact with the fluorescently-labeled hydrogel.

127. The method, system, fluid sample or product of paragraph 126, wherein the range of osmolarity includes a range member selected from the group consisting of from 200 milliosmoles per liter to 400 milliosmoles per liter, from 400 milliosmoles per liter to 600 milliosmoles per liter, from 600 milliosmoles per liter to 1600 milliosmoles per liter, and combinations of any two or any three adjacent ones of the foregoing; and in one option the range may include from 200 milliosmoles per liter to 1600 milliosmoles per liter.

128. A method for analytical evaluation of an aqueous fluid sample, comprising:

subjecting an aqueous fluid sample to an analytical evaluation, optionally not flow cytometry evaluation, wherein:

the fluid sample comprises a plurality of beads disposed in an aqueous liquid medium, the beads comprising a fluorescently-labeled hydrogel that changes in size in response to a change in at least one property of the fluid sample, and in response to stimulation radiation, the beads have a fluorescent emission that changes in intensity with changes in the size of the fluorescently-labeled hydrogel; and the analytical evaluation comprises detecting the intensity of the fluorescent emission from the beads;

and optionally, the analytical evaluation comprises investigating the fluid sample in an investigation zone of an analytical system and in the investigation zone subjecting the fluid sample to stimulation radiation and detecting for response radiation from the investigation zone.

129. A method of paragraph 128, wherein the beads are or have the properties as described for beads, or features of beads, in any one of paragraphs 1-127.

130. A method of either one of paragraph 128 or paragraph 129, wherein the fluid sample is or has properties as described for a fluid sample in any one of paragraphs 1-127.

131. A method of any one of paragraphs 128-130, wherein the detecting is performed by a radiation detection system and the analytical system includes a data evaluation and control system in communication with the radiation detection system, the data evaluation and control system comprising a computer processor and computer memory with stored instructions executable by the computer processor, and the analytical evaluation comprises:

evaluating by the data evaluation and control system executing the evaluation instructions an integrity of the fluid sample, comprising evaluating the detected response radiation from the beads in the fluid sample, and optionally including comparing a detected intensity of the fluorescent emission from the fluid sample to a reference criteria.

132. A method of paragraph 131, wherein the data evaluation and control system is or has the properties as described for a data evaluation and control system in any one of paragraphs 9-10 and 31-35.

133. A method of any one of paragraphs 128-132, wherein the analytical system is selected from the group consisting of:

a live cell imaging and analysis system;

an optical tweezer analysis system; and an analytical system comprises analysis properties of particles based on Brownian motion of the particles, optionally a dynamic light scattering analysis system, a nanoparticle tracking system or a fluorescence correlated spectroscopy system.

General Method

1A. A method for evaluation of at least one property of an aqueous liquid medium, the method comprising analytical evaluation of an aqueous liquid medium, wherein the analytical evaluation comprises:

contacting the liquid medium in an investigation zone with a sample monitoring structure comprising a fluorescently-labeled hydrogel that changes in size in response to a change in at least one property of the liquid medium, and in response to a stimulation radiation the sample monitoring structure has a fluorescent emission that changes in intensity with changes in the size of the fluorescently-labeled hydrogel, and optionally the fluorescently-labeled hydrogel is according to or has properties as provided in any of paragraphs 109-127; and with the liquid medium in the investigation zone in contact with the fluorescent hydrogel, subjecting the fluorescent hydrogel to the stimulation radiation and detecting the intensity of the fluorescent emission from the sample monitoring structure; and optionally the method is according to any one of paragraphs 128-133.

2A. The method of paragraph TA, wherein the intensity of the fluorescent emission of the sample monitoring structure increases with an increase in size of the fluorescently-labeled hydrogel.

3A. The method of any one of either one of paragraph TA or paragraph 2A, wherein the intensity of the fluorescent emission of the sample monitoring structure decreases with an increase in size of the fluorescently-labeled hydrogel.

4A. The method of any one of paragraphs 1A-3A, wherein the size of the fluorescently-labeled hydrogel changes with a change in pH of the liquid medium in contact with the fluorescently-labeled hydrogel over some pH range.

5A. The method of any one of paragraphs 1A-4A, wherein the size of the fluorescently-labeled hydrogel changes with a change in osmolarity in the liquid medium in contact with the fluorescently-labeled hydrogel over some range of osmolarity.

6A. The method of any one of paragraphs 1A-5A, comprising:

prior to the analytical evaluation, preparing the liquid medium with prepared properties; and evaluating a detected response radiation from the sample monitoring structure detected during the detecting to identify changes in properties of the liquid medium relative to the prepared properties.

7A. The method of any one of paragraphs 1A-6A, wherein the detecting is performed by a radiation detection system in communication with a data evaluation and control system comprising a computer processor and computer memory with stored instructions executable by the computer processor, and the analytical evaluation comprises:

evaluating by the data evaluation and control system executing the evaluation instructions an integrity of the liquid medium, comprising evaluating a detected response radiation from the sample monitoring structure; and generating by the computer processor, as a consequence of the evaluating by the data evaluation and control system identifying an integrity deficiency for the liquid medium, a sample integrity warning notification.

8A. The method of any one of paragraphs 1A-7A, comprising evaluating the investigation zone for the presence of target biological material in the investigation zone with the liquid medium.

9A. The method of paragraph 8A, wherein the evaluating the investigation zone for the presence of the target biological material comprises detecting for a second fluorescent emission from the investigation zone indicative of the presence of the target biological material, wherein the second fluorescent emission is different than the fluorescent emission of the sample monitoring structure.

10A. The method of paragraphs 9A, wherein second fluorescent emission is in response to the same stimulation radiation as the fluorescent emission of the sample monitoring structure.

11A. The method of paragraph 9A, comprising subjecting the investigation zone to a second stimulation radiation that is different than the stimulation radiation for the fluorescent emission response from the sample monitoring structure, and wherein the second fluorescent emission is in response to the second stimulation radiation.

12A. The method of paragraph 11A, wherein the investigation zone is not simultaneously subjected to both the second stimulation radiation and the stimulation radiation for the fluorescent emission response from the sample monitoring structure.

13A. The method of any one of paragraphs 1A-12A, wherein the sample monitoring structure comprises sample monitoring beads in contact with the liquid medium, the beads comprising the fluorescently-labeled hydrogel and the fluorescent emission of the beads changes in intensity with changes in the size of the fluorescently-labeled hydrogel; and optionally, the sample monitoring beads are according to or have properties as recited in any of paragraphs 2-3, 59-60, 75-108 and 118.

14A. The method of paragraph 13A, wherein the beads comprise a core-shell structure with a non-hydrogel core and a shell layer of fluorescently-labeled hydrogel surrounding the core.

15A. The method of paragraph 13A, wherein the beads consist essentially of only the fluorescently-labeled hydrogel.

16A. The method of any one of paragraphs 13A-15A, comprising the liquid medium and the beads in the investigation zone with the beads dispersed in the liquid medium.

17A. The method of any one of paragraphs 13A-15A, wherein the beads are in a fixed location accessible by the liquid medium to contact the beads, optionally with the fixed position in the investigation zone.

Flow Cytometry

18A. The method of any one of paragraphs 1A-16A, wherein:

the sample monitoring structure comprises sample monitoring beads comprising the fluorescently-labeled hydrogel and the fluorescent emission of the beads changes in intensity with changes in the size of the fluorescently-labeled hydrogel;

the analytical evaluation comprises flow cytometry evaluation of a fluid sample comprising a plurality of the sample monitoring beads dispersed in the liquid medium, the flow cytometry evaluation comprising flowing the fluid sample through the investigation zone and in the investigation zone subjecting the fluid sample to the stimulation radiation; and detecting the intensity of the fluorescent emission from the beads in response to the stimulation radiation; and optionally, the method is according to or has any features recited in any of paragraphs 1-30, 41-57, 59-64 and 75-127.

19A. The method of paragraph 18A, wherein the flow cytometry evaluation comprises detecting light scatter from the beads and correlating occurrences of detection of the light scatter with occurrences of detection of the fluorescent emission to identify occurrences of the beads.

20A. The method of either one of paragraph 18A or paragraph 19A, wherein the flow cytometry comprises evaluating the fluid sample for the presence of target particles, other than the beads, in the fluid sample passing through the investigation zone.

21A. The method of paragraph 20A, wherein the fluid sample comprises the target particles.

22A. The method of any one of paragraphs 18A-21A, comprising subjecting a plurality of the fluid samples, each comprising the beads, to the flow cytometry evaluation in a sequence, and wherein:

different said fluid samples are evaluated for the same or different target particles, other than the beads; and the method comprises evaluating the fluorescent emissions from the beads detected for each of the fluid samples relative to a reference criteria to determine a sample integrity rating of the sample relative to sample integrity criteria.

Growth Medium Monitoring

23A. The method of any one of paragraphs 1A-17A, wherein:

the analytical evaluation comprises evaluation of a growth medium to support growth of a population of cells or microorganisms, the growth medium comprising the liquid medium; and the contacting comprises contacting the growth medium, optionally in the presence of the cells or microorganisms, with the sample monitoring structure.

24A. The method of paragraph 23A, wherein:

the investigation zone is in a bioreaction container; and during the contacting, the growth medium and the sample monitoring support structure are contained in the bioreaction container during bioreaction processing, optionally to grow the cells or microorganisms, and the analytical evaluation is performed on the growth medium while the growth medium and the sample monitoring support structure are contained in the bioreaction container.

25A. The method of 24A, comprising subjecting a said growth medium in each of a plurality of said bioreaction containers to the analytical evaluation in a sequence controlled by a data evaluation and control system, and optionally saving results of each said analytical evaluation of the sequence in memory of the data evaluation and control system.

26A. The method of paragraph 25A, comprising performing a plurality of said sequences periodically spaced from each other and analyzing with the data evaluation and analysis system changes in the growth medium in each said bioreaction container between different said sequences.

27A. The method of either one of paragraph 25 or paragraph 26A, wherein each said analytical evaluation in the sequence comprises positioning investigation componentry relative to a corresponding said bioreaction container to perform the analytical evaluation on the growth medium in the corresponding said bioreaction container, and the method comprises:

robotically repositioning, at the direction of the data evaluation and control system, relative positions of the investigation componentry and the bioreaction containers between each said analytical evaluation of the sequence to position relative to each other the investigation componentry and a said bioreaction container for a next said analytical evaluation in the sequence.

28A. The method of paragraph 27/a, wherein the robotically repositioning comprises a member selected from the group consisting of:

retaining the bioreaction containers stationary and moving the investigation componentry to reposition the investigation componentry relative to the stationary bioreaction containers;

retaining the investigation componentry stationary and moving the bioreaction containers; and moving both the investigation componentry and one or more of the bioreaction containers.

29A. The method of either one of paragraph 27A or paragraph 28A, wherein the investigation componentry comprises a radiation emitter to provide the stimulation radiation for each said analytical evaluation.

30A. The method of paragraph 29A wherein the investigation componentry comprises a radiation receiver to receive response radiation from the investigation zone for analysis for the fluorescent emission.

31A. The method of any one of paragraphs 27A-30A, wherein different ones of the bioreaction containers contain different bioreaction conditions to simultaneously compare the performances of the different bioreaction conditions to prepare a target biological product, and optionally the target biological product comprises a member selected from the group consisting of cells, expression products and combinations thereof.

Live Cell Imaging and Analysis

32A. The method of any one of paragraphs 25A-31A, wherein during the sequence, the bioreaction containers are contained in an environmentally-controlled incubator of a live cell imaging and analysis system and the bioreaction containers contain cells, and the growth medium is formulated to support growth of the cells.

33A. The method of paragraph 32A, comprising sequentially live cell imaging of the cells in the bioreaction containers.

34A. The method of paragraph 33A, comprising for each said bioreaction container correlating, by the data evaluation and control system, live cell imaging data from the live cell imaging with growth medium data from the analytical evaluation.

35A. The method of paragraph 32A-34A, comprising at least a number of the bioreaction containers selected from the group consisting of 6, 12, 24, 96 and 384, and optionally comprising 6, 12, 24, 96 or 384 of the bioreaction containers.

35.1A The method of any one of paragraphs 32A-35A, wherein each said bioreaction container has a fluid containment volume with a footprint area in the incubator in a range of from 2 to 150 square centimeters.

35.2A. The method of any one of paragraphs 32A-35.1A, wherein the bioreaction containers comprise wells in a multi-well plate, optionally the plate comprises 6, 12, 24, 96 or 384 wells.

35.3A The method of any one of paragraphs 32A-35.1, wherein the bioreaction containers comprise members selected from the group consisting of flasks and dishes.

Parallel Bioreactor System

36A. The method of any one of paragraphs 25A-31A, wherein the bioreaction containers comprise bioreactor vessels in a parallel bioreactor system comprising an automated fluid handling system configured to automatically make fluid additions to the bioreactor vessels, at the direction of a data evaluation and control system.

36.1A. The method of paragraph 36A, wherein the automated fluid handling system comprises an automated liquid handler configured to robotically make liquid additions to the bioreactor vessels, at the direction of the data evaluation and control system, for the bioreaction processing.

37A. The method of either one of paragraph 36A or paragraph 36.1A, comprising;

operating the automated fluid handling system, at the direction of the data evaluation and control system, to perform an automated fluid addition cycle to make a fluid addition to one or more of the bioreactor vessels to make a change to the growth medium in the one or more of the bioreactor vessels to modify bioreaction conditions;

performing a first said sequence of the analytical evaluations before the fluid addition cycle;

performing a second said sequence of the analytical evaluations after the fluid addition cycle; and monitoring, with the data evaluation and control system, changes in the growth medium in each of the one or more bioreactor vessels between the first and second said sequences of the analytical evaluations.

37.1A The method of paragraph 37A, wherein the fluid addition comprises adding to the bioreactor vessel fluid selected from the group consisting of liquid, gas and combinations of liquid and gas.

38A. The method of any one of paragraphs 36A-37.1A, wherein each said bioreactor vessel comprises an internal mixer mixing contents in the bioreactor vessel during the bioreaction processing.

39A. The method of any one of paragraphs 36A-38A, wherein the growth medium is selected from the group consisting of cell culture medium and fermentation medium.

40A. The method of any one of paragraphs 36A-39A, wherein the bioreactor vessels are single-use experimental vessels.

Analytical System

41A. An analytical system for analytical evaluation of at least one property of an aqueous liquid medium, the analytical system comprising:

a sample monitoring structure comprising a fluorescently-labeled hydrogel that changes in size in response to a change in at least one property of an aqueous liquid medium in contact with the fluorescently-labeled hydrogel, and in response to stimulation radiation the sample monitoring structure has a fluorescent emission that changes in intensity with changes in the size of the fluorescently-labeled hydrogel, and optionally the fluorescently-labeled hydrogel is according to or has properties as provided in any of paragraphs 109-127;

an investigation zone configured to receive the liquid medium in contact with the sample monitoring structure for analytical evaluation of the liquid medium;

a radiation delivery system configured to provide the stimulation radiation to impinge on the sample monitoring structure for investigation of the liquid medium in the investigation zone; and a radiation detection system configured to detect response radiation for the fluorescent emission from the sample monitoring structure.

42A. The analytical system of paragraph 41A, comprising a data evaluation and control system in communication with the radiation detection system, the data evaluation and control system comprising a computer processor and computer memory with stored instructions executable by the computer processor to evaluate detected radiation information from the radiation detection system during the analytical evaluation.

43A. The analytical system of either one of paragraph 41A or paragraph 42A, comprising a plurality of containers, each comprising a sample of the liquid medium, and the analytical system is configured to investigate each said liquid medium with the radiation delivery system and the radiation detection system.

44A. The analytical system of paragraph 43A, wherein each said container comprises a said sample monitoring structure in contact with a said sample of the liquid medium, optionally with the sample monitoring structure retained at a fixed location in the container in contact with a said sample of the liquid medium in the container.

45A. The analytical system of paragraph 44A, wherein:

the radiation delivery system comprises investigation componentry configured to provide the stimulation radiation to the sample monitoring structure for performance of a said analytical evaluation, and the analytical system is configured to alter relative positioning of each said sample of the liquid medium of each said container and the investigation componentry to perform a said analytical evaluation on each said sample of liquid medium.

46A. The analytical system of paragraph 45A, wherein each said container comprises a said investigation zone, and the analytical system is configured to perform robotically repositioning of relative positions of the investigation componentry and the containers between performance of the analytical evaluations on the aqueous liquid samples of the different ones of the containers.

47A. The analytical system of paragraph 46A, wherein the robotically repositioning comprises a member selected from the group consisting of retaining the bioreaction containers stationary and moving the investigation componentry to reposition the investigation componentry relative to the stationary bioreaction containers;

retaining the investigation componentry stationary and moving the bioreaction containers; and moving both the investigation componentry and one or more of the bioreaction containers.

48A. The analytical system of paragraph 45A, wherein the investigation zone is not in a said container, and the analytical system is configured to remove from each said container and transfer to the investigation zone an evaluation volume of a said sample of the liquid medium and a corresponding said sample monitoring structure.

49A. The analytical system of any one of paragraphs 44A-48A, wherein the sample monitoring structure comprises sample monitoring beads in contact with the liquid medium in each said container, the beads comprising the fluorescently-labeled hydrogel and the fluorescent emission of the beads changes in intensity with changes in the size of the fluorescently-labeled hydrogel; and optionally, the sample monitoring beads are according to or have properties as recited in any of paragraphs 2-3, 59-60, 75-108 and 118.

50A. The analytical system of paragraph 49A, comprising the liquid medium and the beads in a fluid sample comprising the beads dispersed in the liquid medium.

51A. The analytical system of either one of paragraph 49A or paragraph 50A, wherein the beads comprise a core-shell structure with a non-hydrogel core and a shell layer of fluorescently-labeled hydrogel surrounding the core.

52A. The analytical system of any one of paragraphs 49A-51A, wherein the beads consist essentially of only the fluorescently-labeled hydrogel.

53A. The analytical system of any one of paragraphs 41A-52A, wherein the intensity of the fluorescent emission of the beads increases with an increase in size of the fluorescently-labeled hydrogel.

54A. The analytical system of any one of paragraphs 41A-53A, wherein the intensity of the fluorescent emission of the beads decreases with an increase in size of the fluorescently-labeled hydrogel.

55A. The analytical system of any one of paragraphs 41A-54A, wherein the size of the fluorescently-labeled hydrogel changes with a change in pH of the aqueous liquid in contact with the fluorescently-labeled hydrogel over some pH range.

56A. The analytical system of any one of paragraphs 41A-55A, wherein the size of the fluorescently-labeled hydrogel changes with a change in osmolarity in the aqueous liquid in contact with the fluorescently-labeled hydrogel over some range of osmolarity.

Flow Cytometry System

57A. The analytical system of any one of any one of paragraphs 41A-56A, wherein:

the sample monitoring structure comprises sample monitoring beads comprising the fluorescently-labeled hydrogel and the fluorescent emission of the beads changes in intensity with changes in the size of the fluorescently-labeled hydrogel;

the container is a sample container containing a fluid sample comprising a plurality of the beads dispersed in the liquid medium;

the analytical system comprises a flow cytometry system for flow cytometry evaluation of a fluid sample, the flow cytometry system comprising:

a flow cytometry investigation system comprising the investigation zone and configured to receive during a flow cytometry evaluation in the investigation zone a flow of a said fluid sample; and a sample delivery system configured to interface with the sample container containing the fluid sample and to withdraw from the sample container and transfer to the flow cytometry investigation system an evaluation volume of the fluid sample for the flow cytometry evaluation; and optionally, the flow cytometry system is according to or has any features recited in any of paragraphs 31-57, 59-64 and 75-127.

58A. The analytical system of paragraph 57A, wherein;

the flow cytometry system comprises a plurality of the fluid samples, each said fluid sample being contained in a separate said sample container and comprising the beads and other particles, other than the beads, for flow cytometry evaluation for target particles; and the flow cytometry system is configured to deliver each of the fluid samples to the flow cytometry investigation system for flow cytometry evaluation in a sequence.

59A. The analytical system of paragraph 58A, wherein:

the plurality of the fluid samples comprises a group of said fluid samples in separate sample containers retained in a tray, and the flow cytometry system is configured to perform withdrawing by an autosampler an evaluation volume of the fluid samples in the sequence for the flow cytometry evaluation;

the plurality of the fluid samples comprises multiple said groups of fluid samples with each said group retained in a separate said tray and the flow cytometry system is configured to perform sequential processing of the trays for the flow cytometry evaluation;

the sequential processing of the trays comprises automated robotic transferring of the trays in a tray sequence from a storage structure to the autosampler for performing the withdrawing of fluid samples from each of the trays in the tray sequence.

59.1A The analytical system of either one of paragraph 58 or paragraph 59, wherein the sample containers comprise wells in a multi-well plate, optionally the plate comprising 96, 384 or 1536 wells.

60A. The analytical system of any one of paragraphs 57A-59.1A, comprising a data evaluation and control system in communication with the radiation detection system, the data evaluation and control system comprising a computer processor and computer memory with stored instructions executable by the computer processor to evaluate detected radiation information from the radiation detection system during the flow cytometry evaluation; and wherein the data evaluation and control system is configured to evaluate an integrity of the fluid sample, including evaluating the detected response radiation from the beads in the fluid sample.

Growth Media Systems

61A. The analytical system of any one of paragraphs 41A-56A, wherein the container is a bioreaction container, and the analytical system comprises a plurality of the bioreaction containers each comprising a said investigation zone and having contained therein a said sample monitoring structure and a growth medium formulated to support growth of the cells or microorganisms, wherein the growth medium comprises the liquid medium.

Live Cell Imaging and Analysis Systems

62A. The analytical system of paragraph 61A, comprising a live cell imaging and analysis system comprising an environmentally controlled incubator and a plurality of the bioreaction containers each containing cells and the growth medium formulated to support growth of the cells, and wherein:

the plurality of bioreaction containers are disposed in the environmentally controlled incubator; and the live cell imaging and analysis system is configured to perform, at the direction of a data evaluation and control system, the analytical evaluation separately on each said growth medium in each of the bioreaction containers in the environmentally controlled incubator.

63A. The analytical system of paragraph 62A, wherein the live cell imaging analysis system is configured to obtain time-lapse microscopy images of features of the cells in each of the bioreaction containers in the environmentally controlled incubator.

64A. The analytical system of paragraph 63A, wherein the data evaluation and control system is configured to time correlate one or more said time-lapse microscopy images of a said bioreaction container with results of a said analytical evaluation on growth medium in the same said bioreaction container.

65A. The method of any one of paragraphs 62A-34A, comprising at least a number of the bioreaction containers selected from the group consisting of 6, 12, 24, 96 and 384, and optionally comprising 6, 12, 24, 96 or 384 of the bioreaction containers.

65.1A The method of any one of paragraphs 62A-65A, wherein each said bioreaction container has a fluid containment volume with a footprint area in the incubator in a range of from 2 to 150 square centimeters.

65.2.A. The analytical system of any one of paragraphs 62A-65.1A, wherein the bioreaction containers comprise wells in a multi-well plate, optionally the plate comprises 6, 12, 24, 96 or 384 wells.

65.3A The method of any one of paragraphs 62A-65.1A, wherein the bioreaction containers comprise members selected from the group consisting of flasks and dishes.

Parallel Bioreactor Test Systems

66A. The analytical system of paragraph 61A, wherein the bioreaction container is an experimental bioreactor vessel and the analytical system comprises a parallel bioreactor system comprising:

a plurality of the bioreactor vessels; and an automated fluid handling system configured to make, at the direction of a data evaluation and control system, fluid additions to the bioreactor vessels for parallel bioreaction processing in the bioreactor vessels.

66.1A The analytical system of paragraph 66A, wherein the automated fluid handling system comprises an automated liquid handler configured to robotically make, at the direction of the data evaluation and control system, liquid additions to the bioreactor vessels.

66.2A The analytical system of either one of paragraph 66A or paragraph 66.1A, wherein the automated fluid handling system is configured to make fluid additions to the bioreactor vessels selected from the group consisting of liquid additions, gas additions and combinations of gas and liquid additions.

67A. The analytical system of paragraph 66A, wherein the parallel bioreactor system is configured for automated periodic performance, at the direction of the data evaluation and control system, of a said analytical evaluation on the growth medium in each of the bioreactor vessels to monitor changes over time to the growth medium in each of the bioreactor vessels.

68A. The method of either one of paragraph 66A or paragraph 67A, wherein each said bioreactor vessel comprises an internal mixer to mix, at the direction of the data evaluation and control system, contents in the bioreactor vessel during the bioreaction processing.

69A. The analytical system of any one of paragraphs 66A-68A, wherein the growth medium comprises a medium selected from the group consisting of cell culture medium and fermentation medium.

70A. The analytical system of any one of paragraphs 66A-69A, wherein the bioreactor vessels are single-use experimental vessels.

The terms "comprising", "containing", "including" and "having", and grammatical variations of those terms, are intended to be inclusive and nonlimiting in that the use of such terms indicates the presence of a stated condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or any appropriate grammatical variation of such narrower terms). For example, a statement that something "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term at "at least a portion" means all or a portion that is less than all. The term "at least a part" means all or a part that is less than all. The term "at least a majority" means all or a majority part that is less than all.

What is claimed is:

1. A method for evaluation of at least one property of an aqueous liquid medium, the method comprising analytical evaluation of an aqueous liquid medium, wherein the analytical evaluation comprises:

contacting the liquid medium with a sample monitoring structure comprising a fluorescently-labeled hydrogel that changes in size in response to a change in at least one property of the liquid medium, and in response to a stimulation radiation the sample monitoring structure has a fluorescent emission that changes in intensity with changes in the size of the fluorescently-labeled hydrogel; and subjecting the fluorescently-labeled hydrogel to the stimulation radiation and detecting the intensity of the fluorescent emission from the sample monitoring structure.

2. The method of claim 1, comprising:

prior to the analytical evaluation, preparing the liquid medium with prepared properties; and evaluating a detected response radiation from the sample monitoring structure detected during the detecting to identify changes in properties of the liquid medium relative to the prepared properties.

3. The method of claim 1, comprising evaluating an investigation zone for presence of target biological material in the investigation zone with the liquid medium; and wherein the evaluating the investigation zone for the presence of the target biological material comprises detecting for a second fluorescent emission from the investigation zone indicative of the presence of the target biological material, wherein the second fluorescent emission is different than the fluorescent emission of the sample monitoring structure.

4. The method of claim 1, wherein the sample monitoring structure comprises sample monitoring beads in contact with the liquid medium, the beads comprising the fluorescently-labeled hydrogel and the fluorescent emission of the beads changes in intensity with changes in the size of the fluorescently-labeled hydrogel.

5. The method of claim 4, wherein the beads comprise a core-shell structure with a non-hydrogel core and a shell layer of fluorescently-labeled hydrogel surrounding the core.

6. The method of claim 4, wherein the beads consist essentially of only the fluorescently-labeled hydrogel.

7. The method of claim 4, wherein the beads are dispersed in the liquid medium.

8. The method of claim 1, wherein:

the sample monitoring structure comprises sample monitoring beads comprising the fluorescently-labeled hydrogel and the fluorescent emission of the beads changes in intensity with changes in the size of the fluorescently-labeled hydrogel; and the analytical evaluation comprises flow cytometry evaluation of a fluid sample comprising a plurality of the sample monitoring beads dispersed in the liquid medium, the flow cytometry evaluation comprising:

flowing the fluid sample through an investigation zone and in the investigation zone subjecting the fluid sample to the stimulation radiation; and detecting the intensity of the fluorescent emission from the beads in response to the stimulation radiation.

9. The method of claim 1, wherein:

the analytical evaluation comprises evaluation of a growth medium to support growth of cells or microorganisms, the growth medium comprising the liquid medium; and the contacting comprises contacting the growth medium, in presence of the cells or microorganisms, with the sample monitoring structure.

10. The method of claim 9, wherein the analytical evaluation further comprises evaluation of the cells in a live cell imaging and analysis system.

11. The method of claim 9, wherein:

during the contacting, the growth medium and the sample monitoring structure are contained in a bioreaction container during bioreaction processing to grow the cells or microorganisms, and the analytical evaluation is performed on the growth medium while the growth medium and the sample monitoring structure are contained in the bioreaction container;

and the method further comprises:

subjecting a said growth medium in each of a plurality of the bioreaction containers to the analytical evaluation in a sequence controlled by a data evaluation and control system;

performing a plurality of the sequences periodically spaced from each other and analyzing with the data evaluation and control system changes in the growth medium in each said bioreaction container between different said sequences, and wherein each said analytical evaluation in the sequence comprises positioning investigation componentry relative to a corresponding said bioreaction container to perform the analytical evaluation on the growth medium in the corresponding said bioreaction container; and robotically repositioning, at direction of the data evaluation and control system, relative positions of the investigation componentry and the plurality of the bioreaction containers between different ones of the analytical evaluations of the sequence to position relative to each other the investigation componentry and a said bioreaction container for a next said analytical evaluation in the sequence.

12. The method of claim 11, wherein during the sequence, the plurality of the bioreaction containers are contained in an environmentally-controlled incubator of a live cell imaging and analysis system and the plurality of the bioreaction containers contain cells, and the growth medium is formulated to support growth of the cells; and the method further comprises sequentially live cell imaging of the cells in the plurality of the bioreaction containers.

13. The method of claim 11, wherein each said bioreaction container of the plurality of the bioreaction containers comprise a bioreactor vessels in a parallel bioreactor system comprising an automated fluid handling system configured to robotically make fluid additions to the bioreactor vessels, at direction of the data evaluation and control system, for the bioreaction processing.

14. An analytical system for analytical evaluation of at least one property of an aqueous liquid medium, the analytical system comprising:

a sample monitoring structure comprising a fluorescently-labeled hydrogel that changes in size in response to a change in at least one property of an aqueous liquid medium in contact with the fluorescently-labeled hydrogel, and in response to stimulation radiation the sample monitoring structure has a fluorescent emission that changes in intensity with changes in the size of the fluorescently-labeled hydrogel;

an investigation zone configured to receive the liquid medium in contact with the sample monitoring structure for analytical evaluation of the liquid medium;

a radiation delivery system configured to provide the stimulation radiation to impinge on the sample monitoring structure for investigation of the liquid medium in the investigation zone; and a radiation detection system configured to detect response radiation for the fluorescent emission from the sample monitoring structure.

15. The analytical system of claim 14, comprising a plurality of containers, each comprising a sample of aqueous liquid medium, and the analytical system is configured to investigate each said sample of aqueous liquid medium with the radiation delivery system and the radiation detection system; and wherein each said container comprises a said sample monitoring structure in contact with a said sample of aqueous liquid medium.

16. The analytical system of claim 15, wherein:

the radiation delivery system comprises investigation componentry configured to provide the stimulation radiation to the sample monitoring structure for performance of a said analytical evaluation, the analytical system is configured to alter relative positioning of each said sample of aqueous liquid medium of each said container and the investigation componentry to perform a said analytical evaluation on each said sample of aqueous liquid medium; and each said container comprises a said investigation zone, and the analytical system is configured to perform robotic repositioning of relative positions of the investigation componentry and the plurality of containers between performance of different ones of the analytical evaluations on the samples of aqueous liquid of different ones of the containers.

17. The analytical system of claim 15, wherein the sample monitoring structure comprises sample monitoring beads comprising the fluorescently-labeled hydrogel and the fluorescent emission of the beads changes in intensity with changes in the size of the fluorescently-labeled hydrogel; and wherein each said container comprises a plurality of the sample monitoring beads dispersed in a said sample of aqueous liquid medium.

18. The analytical system of claim 14, comprising a sample container, and wherein:

the sample monitoring structure comprises sample monitoring beads comprising the fluorescently-labeled hydrogel and the fluorescent emission of the beads changes in intensity with changes in the size of the fluorescently-labeled hydrogel;

the sample container contains a fluid sample comprising a plurality of the beads dispersed in the liquid medium; and the analytical system comprises a flow cytometry system for flow cytometry evaluation of the fluid sample, the flow cytometry system comprising:

a flow cytometry investigation system comprising the investigation zone and configured to receive during a flow cytometry evaluation in the investigation zone a flow of the fluid sample; and a sample delivery system configured to interface with the sample container containing the fluid sample and to withdraw from the sample container and transfer to the flow cytometry investigation system an evaluation volume of the fluid sample for the flow cytometry evaluation.

19. The analytical system of claim 18, wherein:

the flow cytometry system comprises a plurality of the fluid samples, each said fluid sample of the plurality of the fluid samples being contained in a separate said sample container and comprising a plurality of the beads and other particles, other than the beads, for flow cytometry evaluation for target particles;

the flow cytometry system is configured to deliver each of the plurality of the fluid samples to the flow cytometry investigation system for flow cytometry evaluation in a sequence;

the plurality of the fluid samples comprises a group of the fluid samples in separate sample containers retained in a tray, and the flow cytometry system is configured to perform withdrawing by an autosampler an evaluation volume of each of the group of the fluid samples in the sequence for the flow cytometry evaluation;

the plurality of the fluid samples comprises multiple said groups of the fluid samples with each said group of the fluid samples retained in a separate said tray and the flow cytometry system is configured to perform sequential processing of the trays for the flow cytometry evaluation;

the sequential processing of the trays comprises automated robotic transferring of the trays in a tray sequence from a storage structure to the autosampler for performing the withdrawing of fluid samples from each of the trays in the tray sequence;

the system further comprises a data evaluation and control system in communication with the radiation detection system, the data evaluation and control system comprising a computer processor and computer memory with stored instructions executable by the computer processor to evaluate detected radiation information from the radiation detection system during the flow cytometry evaluation; and the data evaluation and control system is configured to evaluate an integrity of the fluid sample, including evaluating the detected response radiation from the beads in the fluid sample.

20. The analytical system of claim 14, comprising a plurality of bioreaction containers each comprising a said investigation zone and having contained therein a said sample monitoring structure and a growth medium formulated to support growth of cells or microorganisms, wherein each said growth medium comprises aqueous liquid, and the analytical system further comprises:

a live cell imaging and analysis system comprising an environmentally controlled incubator having disposed therein the plurality of the bioreaction containers;

a data evaluation and control system in communication with the radiation detection system, the data evaluation and control system comprising a computer processor and computer memory with stored instructions executable by the computer processor to evaluate detected radiation information from the radiation detection system during the analytical evaluation; and the live cell imaging and analysis system being configured to perform, at the direction of the data evaluation and control system, the analytical evaluation separately on each said growth medium in each of the plurality of the bioreaction containers in the environmentally controlled incubator.

21. The analytical system of claim 14, wherein:

the analytical system comprises a plurality of bioreaction containers each comprising a said investigation zone and having contained therein a said sample monitoring structure and a growth medium formulated to support growth of cells or microorganisms, wherein each said growth medium comprises aqueous liquid;

the plurality of the bioreaction containers are a plurality of experimental bioreactor vessels and the analytical system comprises a parallel bioreactor experimentation system comprising:

the plurality of the bioreactor vessels;

a data evaluation and control system in communication with the radiation detection system, the data evaluation and control system comprising a computer processor and computer memory with stored instructions executable by the computer processor to evaluate detected radiation information from the radiation detection system during the analytical evaluation; and an automated fluid handling system configured to robotically make, at the direction of the data evaluation and control system, fluid additions to the bioreactor vessels for parallel bioreaction processing in the bioreactor vessels.

22. The method of claim 1, wherein the intensity of the fluorescent emission of the sample monitoring structure decreases with an increase in size of the fluorescently-labeled hydrogel.

23. A product for use in monitoring an aqueous fluid sample during flow cytometry evaluation of the fluid sample, the product comprising:

a plurality of beads for inclusion in an aqueous liquid medium of an aqueous fluid sample to monitor the fluid sample during flow cytometry evaluation, the beads having a fluorescent emission when subjected to a stimulation radiation during flow cytometry, and each said bead comprising:

a non-hydrogel core and a shell layer of fluorescently-labeled hydrogel surrounding the core;

wherein the fluorescently-labeled hydrogel changes in size in response to a change in at least one property of the aqueous fluid sample; and wherein an intensity of the fluorescent emission from the bead changes with changes in the size of the fluorescently-labeled hydrogel.

24. The method of claim 1, wherein:

the fluorescently-labeled hydrogel comprises a plurality of first fluorochrome moieties and a plurality of second fluorochrome moieties;

the first fluorochrome moiety has a first fluorescent emission in response to the stimulation radiation and the second fluorochrome moiety has a second fluorescent emission in response to stimulation by the first fluorescent emission, the second fluorescent emission being different than the first fluorescent emission; and the fluorescent emission of the sample monitoring structure comprises the second fluorescent emission, and the second fluorescent emission decreases as the size of the hydrogel increases with a corresponding increase in spacing between occurrences of the first fluorochrome moiety and occurrences of the second fluorochrome moiety.

* * * * *